US011857697B2

(12) United States Patent
Spence et al.

(10) Patent No.: US 11,857,697 B2
(45) Date of Patent: Jan. 2, 2024

(54) COMPOSITIONS AND METHODS FOR OBTAINING 3-DIMENSIONAL LUNG-LIKE EPITHELIUM AND RELATED USES THEREOF

(71) Applicant: THE REGENTS OF THE UNIVERSITY OF MICHIGAN, Ann Arbor, MI (US)

(72) Inventors: Jason Spence, Ann Arbor, MI (US); Alyssa Miller, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 427 days.

(21) Appl. No.: 15/994,749

(22) Filed: May 31, 2018

(65) Prior Publication Data
US 2018/0344901 A1 Dec. 6, 2018

Related U.S. Application Data

(60) Provisional application No. 62/513,191, filed on May 31, 2017.

(51) Int. Cl.
*C12N 5/071* (2010.01)
*C12N 5/00* (2006.01)
*A61K 35/42* (2015.01)
*A61L 27/38* (2006.01)
*C12N 5/074* (2010.01)
*C12N 5/0735* (2010.01)

(52) U.S. Cl.
CPC .......... *A61L 27/3895* (2013.01); *A61K 35/42* (2013.01); *A61L 27/3804* (2013.01); *A61L 27/3813* (2013.01); *A61L 27/3834* (2013.01); *A61L 27/3839* (2013.01); *A61L 27/3869* (2013.01); *C12N 5/0018* (2013.01); *C12N 5/0062* (2013.01); *C12N 5/0606* (2013.01); *C12N 5/0607* (2013.01); *C12N 5/0688* (2013.01); *C12N 5/0689* (2013.01); *A61L 2430/22* (2013.01); *C12N 2501/113* (2013.01); *C12N 2501/115* (2013.01); *C12N 2501/117* (2013.01); *C12N 2501/119* (2013.01); *C12N 2501/155* (2013.01); *C12N 2501/385* (2013.01); *C12N 2501/415* (2013.01); *C12N 2501/999* (2013.01); *C12N 2506/02* (2013.01); *C12N 2506/03* (2013.01); *C12N 2506/27* (2013.01); *C12N 2506/45* (2013.01); *C12N 2513/00* (2013.01)

(58) Field of Classification Search
CPC .................................................. C12N 5/0689
See application file for complete search history.

(56) References Cited

U.S. PATENT DOCUMENTS

2020/0093959 A1* 3/2020 Snoeck ............... A61L 27/3633

OTHER PUBLICATIONS

Chen et al., Nature Cell Biology, 2017 (epub Apr. 24, 2017), 19(5):542-549 (Supplemental Figs 1-5 and Suppl Table 1 included) (Year: 2017).*
Huang et al., Nature Protocols, 2015, 10(3):413-425. (Year: 2015).*
Huang et al., Nature Biotechnology, 2014, vol. 32, No. 1, p. 84-91 plus Supplemental info (Year: 2014).*
Abler, L.L., et al., 2009. Conditional gene inactivation reveals roles for Fgf10 and Fgfr2 in establishing a normal pattern of epithelial branching in the mouse lung. Dev. Dyn. 238, 1999-2013.
Bagai, S., et al., 2002. Fibroblast growth factor-10 is a mitogen for urothelial cells. J. Biol. Chem. 277, 23828-23837.
Bellusci, S., et al., 1997a. Involvement of Sonic hedgehog (Shh) in mouse embryonic lung growth and morphogenesis. Development 124, 53-63.
Bellusci, S., et al., 1997b. Fibroblast growth factor 10 (FGF10) and branching morphogenesis in the embryonic mouse lung. Development 124, 4867-4878.
Bellusci, S., et al., 1996. Evidence from normal expression and targeted misexpression that bone morphogenetic protein (Bmp-4) plays a role in mouse embryonic lung morphogenesis. Development 122, 1693-1702.
Branchfield, K., et al., 2016. A three-dimensional study of alveologenesis in mouse lung. Developmental Biology. 409(2): 429-441.
Cardoso, W.V., et al., 1997. FGF-1 and FGF-7 induce distinct patterns of growth and differentiation in embryonic lung epithelium. Dev. Dyn. 208, 398-405.
Chang, D.R., et al., 2013. Lung epithelial branching program antagonizes alveolar differentiation. Proceedings of the National Academy of Sciences. 2013, vol. 110, No. 45, pp. 18042-18051.
Chen, F., et al., 2010. A retinoic acid-dependent network in the foregut controls formation of the mouse lung primordium. J. Clin. Invest. 120, 2040-2048.
Cornett, B., et al., 2013. Wntless is required for peripheral lung differentiation and pulmonary vascular development. Developmental Biology 379, 38-52.
D'Amour, K.A., et al., 2005. Efficient differentiation of human embryonic stem cells to definitive endoderm. Nat Biotechnol 23, 1534-1541.
Del Moral, P.- M., Warburton, D., 2010. Explant culture of mouse embryonic whole lung, isolated epithelium, or mesenchyme under chemically defined conditions as a system to evaluate the molecular mechanism of branching morphogenesis and cellular differentiation. Methods Mol. Biol. 633, 71-79.

(Continued)

Primary Examiner — Allison M Fox
(74) Attorney, Agent, or Firm — Casimir Jones, S.C.; Robert A. Goetz

(57) ABSTRACT

The invention disclosed herein generally relates to methods and systems for growing, expanding and/or obtaining 3-dimensional lung-like epithelium comprising cells having SOX9 protein activity and SOX2+ protein activity. In particular, the invention disclosed herein relates to methods and systems for growing human cells having SOX9 protein activity and SOX2+ protein activity in vitro, and for promoting pluripotent stem cell derived ventral-anterior foregut spheroid tissue into 3-dimensional lung-like epithelium comprising cells having SOX9 protein activity and SOX2+ protein activity.

11 Claims, 42 Drawing Sheets

Specification includes a Sequence Listing.

(56) References Cited

OTHER PUBLICATIONS

Desai, T.J., et al., 2006. Distinct roles for retinoic acid receptors alpha and beta in early lung morphogenesis. Developmental Biology 291, 12-24.

Desai, T.J., et al. 2004. Retinoic acid selectively regulates Fgf10 expression and maintains cell identity in the prospective lung field of the developing foregut. Developmental Biology 273, 402-415.

Domyan, E.T., et al., 2011. Signaling through BMP receptors promotes respiratory identity in the foregut via repression of Sox2. Development 138, 971-981.

Domyan, E.T., Sun, X., 2010. Patterning and plasticity in development of the respiratory lineage. Dev. Dyn. 240, 477-485.

Dye, B.R., et al., 2016a. A bioengineered niche promotes in vivo engraftment and maturation of pluripotent stem cell derived human lung organoids. Elife 5, e19732, pp. 1-18.

Dye, B.R., et al., 2015. In vitro generation of human pluripotent stem cell derived lung organoids. Elife 4. e05098, pp. 1-25.

Dye, B.R., et al. 2016b. How to Grow a Lung: Applying Principles of Developmental Biology to Generate Lung Lineages from Human Pluripotent Stem Cells. Curr Pathobiol Rep 1-11, 4:47-57.

Elluru, R.G., Whitsett, J.A., 2004. Potential role of Sox9 in patterning tracheal cartilage ring formation in an embryonic mouse model. Arch. Otolaryngol. Head Neck Surg. 130, 732-736.

Firth, A.L., et al., 2014. Generation of multiciliated cells in functional airway epithelia from human induced pluripotent stem cells. Proceedings of the National Academy of Sciences 111, E1723-30.

Ghaedi, M., et al., 2013. Human iPS cell-derived alveolar epithelium repopulates lung extracellular matrix. J. Clin. Invest. 123, 4950-4962.

Gilpin, S.E., et al.., 2014. Enhanced lung epithelial specification of human induced pluripotent stem cells on decellularized lung matrix. Ann. Thorac. Surg. 98, 1721-9—discussion 1729.

Goss, A.M., et al., 2009. Wnt2/2b and β-Catenin Signaling are Necessary and Sufficient to Specify Lung Progenitors in the Foregut. Developmental Cell 17, 290-298.

Gotoh, S., et al., 2014. Generation of alveolar epithelial spheroids via isolated progenitor cells from human pluripotent stem cells. Stem Cell Reports 3, 394-403.

Green, M.D., et al., 2011. Generation of anterior foregut endoderm from human embryonic and induced pluripotent stem cells. Nat Biotechnol 1-7. vol. 29, No. 3, pp. 267-273.

Harris-Johnson, K.S., et al., 2009. beta-Catenin promotes respiratory progenitor identity in mouse foregut. Proceedings of the National Academy of Sciences 106, 16287-16292.

Hashimoto, S., et al., 2012. β-Catenin-SOX2 signaling regulates the fate of developing airway epithelium. Journal of Cell Science 125, 932-942.

Herriges, J.C., et al., 2015. FGF-Regulated ETV Transcription Factors Control FGF-SHH Feedback Loop in Lung Branching. Developmental Cell 35, 322-332.

Hines, E.A., Sun, X., 2014. Tissue crosstalk in lung development. J Cell Biochem 115, 1469-1477.

Huang, S.X.L., et al., 2014. Highly efficient generation of lung and airway epithelial cells from human pluripotent stem cells. Nat Biotechnol 32(1): 84-91.

Kaarteenaho, R., Lappi-Blanco, E., Lehtonen, S., 2010. Epithelial N-cadherin and nuclear β-catenin are up-regulated during early development of human lung. BMC Dev Biol 10, 113, pp. 1-14.

Kadzik, R.S., et al., 2014. Wnt ligand/Frizzled 2 receptor signaling regulates tube shape and branch-point formation in the lung through control of epithelial cell shape. Proceedings of the National Academy of Sciences 111, 12444-12449.

Kim, C.F.B., et al., 2005. Identification of bronchioalveolar stem cells in normal lung and lung cancer. Cell 121, 823-835.

Kim, H.Y., Nelson, C.M., 2012. Extracellular matrix and cytoskeletal dynamics during branching morphogenesis. Organogenesis 8, 56-64.

Konishi, S., et al., 2016. Directed Induction of Functional Multiciliated Cells in Proximal Airway Epithelial Spheroids from Human Pluripotent Stem Cells. Stem Cell Reports, vol. 6, 18-25.

Kopp, J.L., et al., 2011. Sox9+ ductal cells are multipotent progenitors throughout development but do not produce new endocrine cells in the normal or injured adult pancreas. Development 138, 653-665.

Lange, A.W., et al., 2015. Hippo/Yap signaling controls epithelial progenitor cell proliferation and differentiation in the embryonic and adult lung. Journal of Molecular Cell Biology 7, 35-47.

Lee, J.-H., et al. 2014. Lung Stem Cell Differentiation in Mice Directed by Endothelial Cells via a BMP4-NFATc1-Thrombospondin-1 Axis. Cell 156, 440-455.

Longmire, T.A., et al., 2012. Efficient derivation of purified lung and thyroid progenitors from embryonic stem cells. Cell Stem Cell 10, 398-411.

Lu, B.C., et al., 2009. Etv4 and Etv5 are required downstream of GDNF and Ret for kidney branching morphogenesis. Nat Genet 41, 1295-1302.

Mahoney, J.E., et al., 2014. The Hippo Pathway Effector Yap Controls Patterning and Differentiation of Airway Epithelial Progenitors. Dev. Cell 30, 137-150.

Makarenkova, H.P., et al., 2009. Differential interactions of FGFs with heparan sulfate control gradient formation and branching morphogenesis. Sci Signal 2, ra55-ra55, 21 pages.

Malpel, S., Mendelsohn, C., Cardoso, W.V., 2000. Regulation of retinoic acid signaling during lung morphogenesis. Development 127, 3057-3067.

Metzger, R.J., et al., 2008. The branching programme of mouse lung development. Nature 453 (7196), 745-750.

Miller A. J. et al. In Vitro Induction and In Vivo Engraftment of Lung Bud Tip Progenitor Cells Derived from Human Pluripotent Stem Cells. Stem Cell Reports, Jan. 2018, vol. 10, 101-119.

Min, H., et al., 1998. Fgf-10 is required for both limb and lung development and exhibits striking functional similarity to *Drosophila* branchless. Genes & Development 12, 3156-3161.

Moens, C.B., et al., 1992. A targeted mutation reveals a role for N-myc in branching morphogenesis in the embryonic mouse lung. Genes Dev. 6, 691-704.

Morrisey, E.E., et al., 2013. Molecular determinants of lung development. Ann Am Thorac Soc 10, S12-6.

Morrisey, E.E., Hogan, B.L.M., 2010. Preparing for the First Breath: Genetic and Cellular Mechanisms in Lung Development. Developmental Cell 18, 8-23.

Motoyama, J., et al., 1998. Essential function of Gli2 and Gli3 in the formation of lung, trachea and oesophagus. Nat Genet 20, 54-57.

Mou, H., et al., 2012. Generation of Multipotent Lung and Airway Progenitors from Mouse ESCs and Patient-Specific Cystic Fibrosis iPSCs. Cell Stem Cell 10, 385-397.

Mucenski, M.L., et al., 2005. β-Catenin regulates differentiation of respiratory epithelial cells in vivo. Am J Physiol Lung Cell Mol Physiol 289: L971-L979.

Mucenski, M.L., et al., 2003. beta-Catenin is required for specification of proximal/distal cell fate during lung morphogenesis. J. Biol. Chem. 278, 40231-40238.

Nyeng, P., et al., 2008. FGF10 maintains distal lung bud epithelium and excessive signaling leads to progenitor state arrest, distalization, and goblet cell metaplasia. BMC Dev Biol 8, 2, pp. 1-15.

Okubo, T., et al., 2005. Nmyc plays an essential role during lung development as a dosage-sensitive regulator of progenitor cell proliferation and differentiation. Development 132, 1363-1374.

Ornitz et al., 1996. Receptor specificity of the fibroblast growth factor family. J. Biol. Chem. 271, 15292-15297.

Ornitz, D.M., Yin, Y., 2012. Signaling Networks Regulating Development of the Lower Respiratory Tract. Cold Spring Harb Perspect Biol 4, a008318-a008318.

Perl, A.-K.T., et al., 2005. Normal lung development and function after Sox9 inactivation in the respiratory epithelium. genesis 41, 23-32.

Que, J., et al., 2007. Multiple dose-dependent roles for Sox2 in the patterning and differentiation of anterior foregut endoderm. Development 134, 2521-2531.

Rawlins, E.L., 2010. The building blocks of mammalian lung development. Dev. Dyn. 240, 463-476.

(56) References Cited

OTHER PUBLICATIONS

Rawlins, E.L., et al., 2009. The Id2+ distal tip lung epithelium contains individual multipotent embryonic progenitor cells. Development 136, 3741-3745.
Rock, J.R., Hogan, B.L.M., 2011. Epithelial Progenitor Cells in Lung Development, Maintenance, Repair, and Disease. Annu. Rev. Cell Dev. Biol. 27, 493-512.
Rockich, B.E., et al., 2013. Sox9 plays multiple roles in the lung epithelium during branching morphogenesis. Proceedings of the National Academy of Sciences, E4456-E4464.
Sekine, K., et al., 1999. Fgf10 is essential for limb and lung formation. Nat Genet 21, 138-141.
Shu, W., et al., 2005. Wnt/beta-catenin signaling acts upstream of N-myc, BMP4, and FGF signaling to regulate proximal-distal patterning in the lung. Dev Biol 283, 226-239.
Spence, J.R., et al., 2009. Sox17 Regulates Organ Lineage Segregation of Ventral Foregut Progenitor Cells. Developmental Cell 17, 62-74.
Spence, J.R. et al., 2011. Directed differentiation of human pluripotent stem cells into intestinal tissue in vitro. Nature 470, 105-109.
Tichelaar, J.W., Lu, W., Whitsett, J.A., 2000. Conditional expression of fibroblast growth factor-7 in the developing and mature lung. Journal of Biological Chemistry. vol. 275, No. 16, pp. 11858-11864.
Varner, V.D., Nelson, C.M., 2014. Cellular and physical mechanisms of branching morphogenesis. Development 141, 2750-2759.
Volckaert, T., et al., 2013. Localized Fgf10 expression is not required for lung branching morphogenesis but prevents differentiation of epithelial progenitors. Development 140, 3731-3742.

Weaver, M., et al., 2000. Bmp4 and Fgf10 play opposing roles during lung bud morphogenesis. Development 127, 2695-2704.
Weaver, M., et al., 1999. Bmp signaling regulates proximal-distal differentiation of endoderm in mouse lung development. Development 126, 4005-4015.
White, A.C., et al., 2006. FGF9 and SHH signaling coordinate lung growth and development through regulation of distinct mesenchymal domains. Development 133, 507-1517.
Wong, A.P., et al., 2012. Directed differentiation of human pluripotent stem cells into mature airway epithelia expressing functional CFTR protein. Nat Biotechnol. 30(9): 876-882.
Yin, Y., et al., 2011. Mesothelial- and epithelial-derived FGF9 have distinct functions in the regulation of lung development. Development 138, 3169-3177.
Yin, Y., et al., 2008. An FGF-WNT gene regulatory network controls lung mesenchyme development. Developmental Biology 319, 426-436.
Zhang, M., et al., 2010. Expression of SHH signaling pathway components in the developing human lung. Histochem. Cell Biol. 134, 327-335.
Zhang, X., et al., 2006. Receptor specificity of the fibroblast growth factor family. The complete mammalian FGF family. J. Biol. Chem. 281, 15694-15700.
Zhang, Y., et al., 2016. E3 ubiquitin ligase RFWD2 controls lung branching through protein-level regulation of ETV transcription factors. Proceedings of the National Academy of Sciences 2, vol. 113, No. 27, 7557-7562.
Zhao, R., et al., 2014. Yap tunes airway epithelial size and architecture by regulating the identity, maintenance, and self-renewal of stem cells. Developmental Cell 30, 151-165.

* cited by examiner

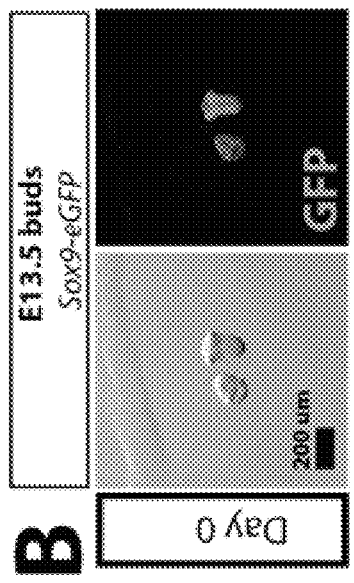
FIG. 1A
FIG. 1B
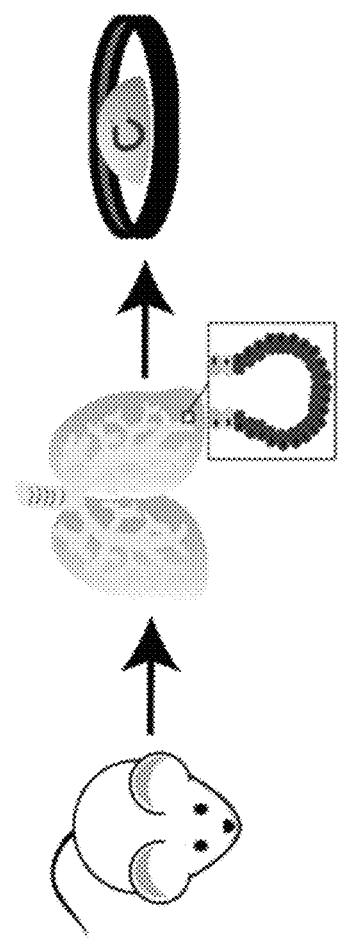
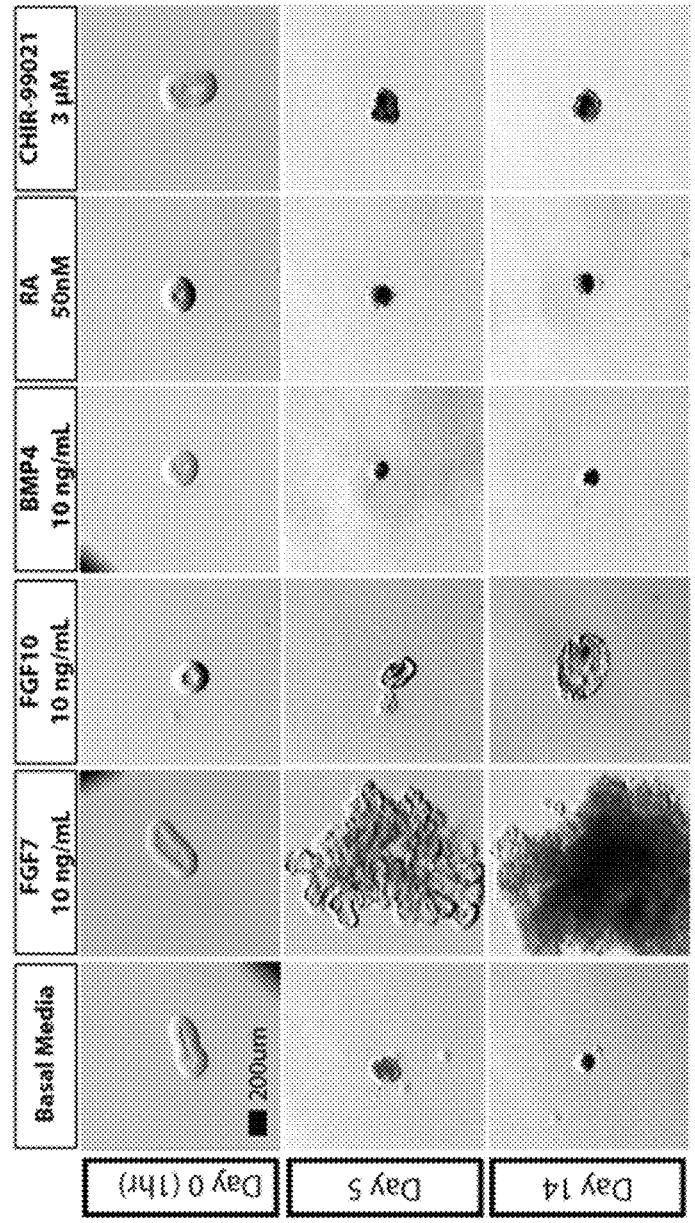
FIG. 1C

FIG. 10M
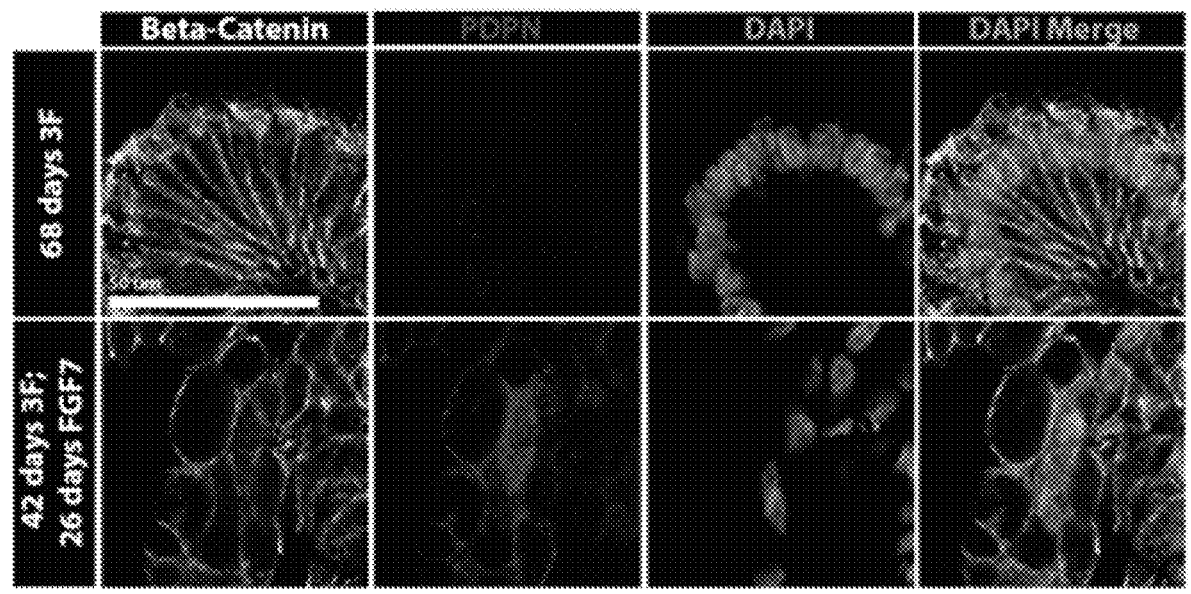
FIG. 10N
FIG. 10O
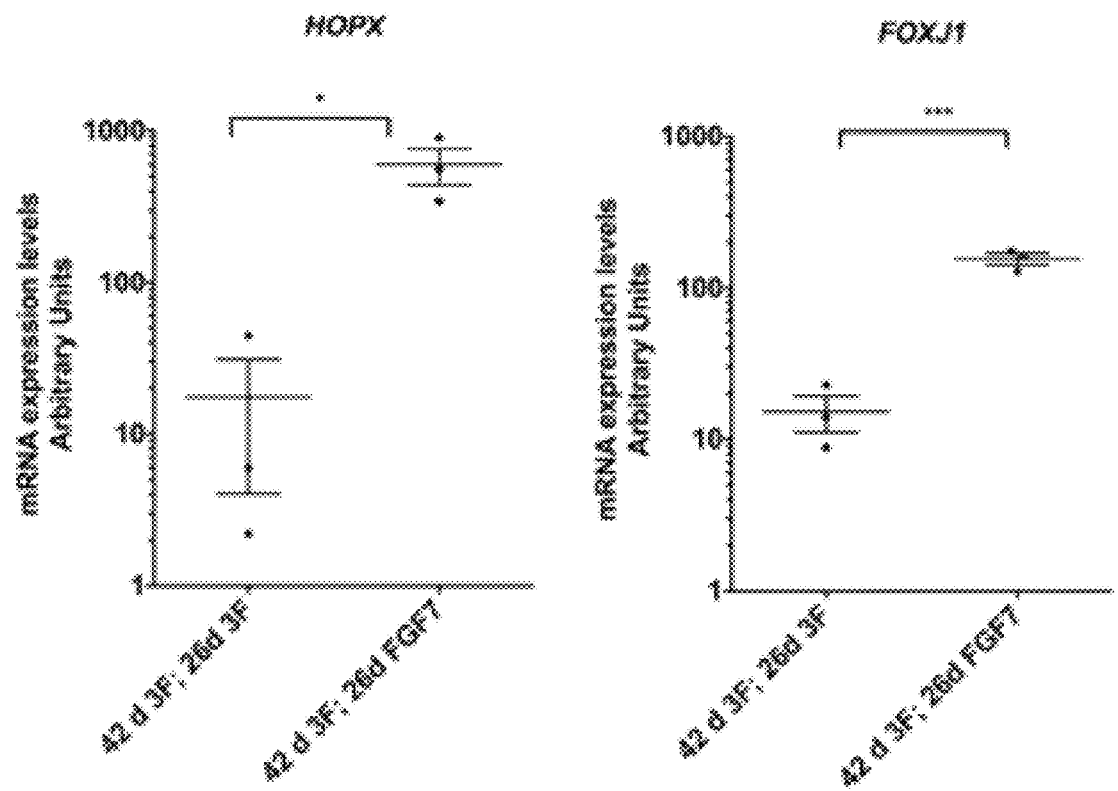

FIG. 11D
FIG. 11E
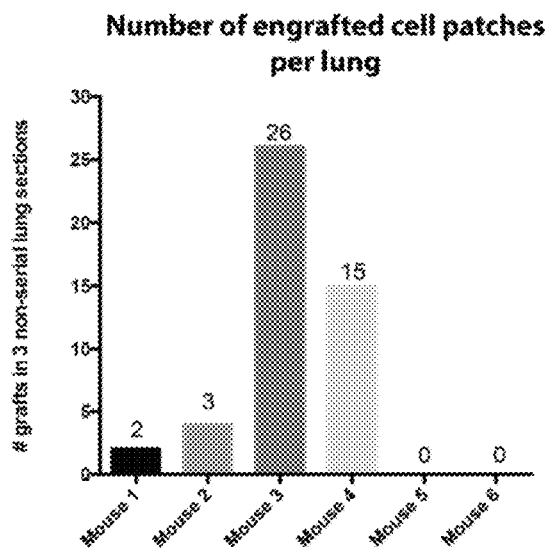
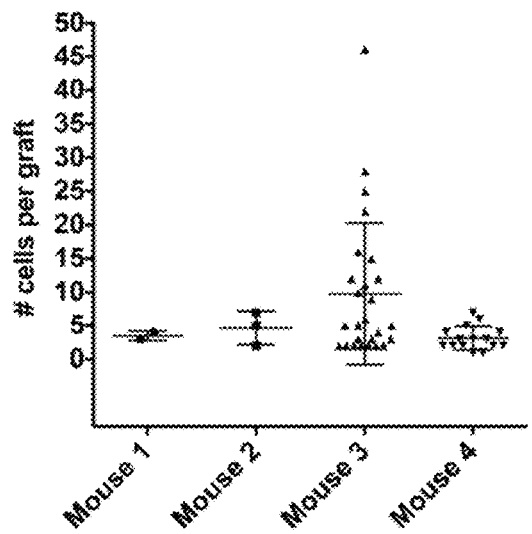
FIG. 11F
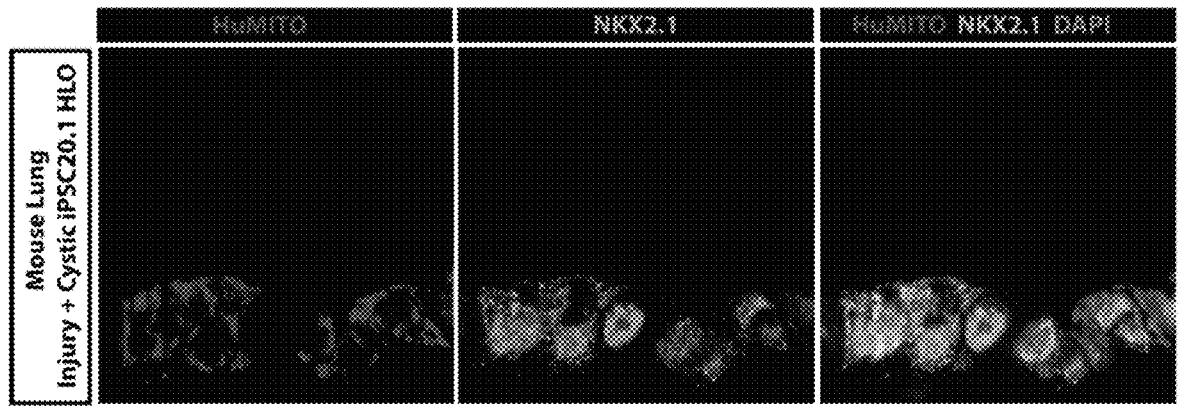

SEQUENCE LISTING

<160> NUMBER OF SEQ ID NOS: 46

<210> SEQ ID NO 1
<211> LENGTH: 20
<212> TYPE: PRT
<213> ORGANISM: Artificial Sequence
<220> FEATURE:

```
<223> OTHER INFORMATION: Synthetic

<400> SEQUENCE: 1

Thr Ala Gly Ala Ala Gly Ala Thr Gly Gly Cys Thr Cys Gly Gly Ala
1               5                   10                  15

Gly Cys Ala Gly
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic

<400> SEQUENCE: 2

Cys Thr Gly Gly Gly Ala Cys Cys Thr Gly Thr Gly Ala Gly Thr Gly
1               5                   10                  15

Gly Thr Gly

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Thr Gly Thr Thr Cys Ala Ala Gly Gly Ala Cys Ala Gly Gly Thr Thr
1               5                   10                  15

Gly Thr Gly Gly
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic

<400> SEQUENCE: 4

Gly Ala Thr Cys Ala Cys Thr Cys Thr Gly Thr Cys Gly Gly Cys Cys
1               5                   10                  15

Ala Thr Cys Thr
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Thr Gly Thr Cys Ala Gly Cys Ala Ala Thr Gly Cys Ala Thr Cys Cys
1               5                   10                  15

Thr Gly Cys Ala
            20

<210> SEQ ID NO 6
<211> LENGTH: 20
<212> TYPE: PRT
<213> ORGANISM: Artificial Sequence
<220> FEATURE:
```

<223> OTHER INFORMATION: Synthetic

<400> SEQUENCE: 6

Cys Cys Gly Thr Thr Cys Ala Gly Cys Thr Cys Thr Gly Gly Gly Ala
1               5                   10                  15

Thr Gly Ala Cys
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Ala Gly Ala Ala Ala Ala Gly Ala Ala Ala Ala Gly Thr Cys Cys
1               5                   10                  15

Cys Cys Ala Ala Ala Thr Gly
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Gly Thr Cys Cys Thr Thr Gly Cys Ala Gly Cys Ala Thr Cys Thr
1               5                   10                  15

Gly Ala Ala Thr
            20

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

Ala Gly Cys Ala Cys Cys Thr Cys Cys Gly Gly Ala Gly Ala Gly
1               5                   10                  15

Ala Thr Ala

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Thr Cys Thr Cys Thr Ala Cys Gly Gly Thr Gly Ala Cys Cys Ala Cys
1               5                   10                  15

Ala Thr Cys Gly
            20

<210> SEQ ID NO 11
<211> LENGTH: 20
<212> TYPE: PRT
<213> ORGANISM: Artificial Sequence
<220> FEATURE:

<223> OTHER INFORMATION: Synthetic

<400> SEQUENCE: 11

Ala Gly Cys Thr Thr Cys Thr Thr Cys Ala Gly Thr Thr Cys Gly Gly
1               5                   10                  15

Thr Gly Gly Ala
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Cys Cys Thr Cys Cys Ala Ala Cys Ala Cys Ala Gly Ala Thr Thr Ala
1               5                   10                  15

Cys Cys Cys Gly
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Ala Cys Thr Thr Gly Ala Ala Gly Ala Ala Thr Cys Cys Thr Cys Gly
1               5                   10                  15

Gly Gly Cys Ala
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Cys Ala Ala Ala Gly Cys Cys Thr Cys Cys Ala Ala Cys Cys Thr Cys
1               5                   10                  15

Thr Ala Cys Cys
            20

<210> SEQ ID NO 15
<211> LENGTH: 18
<212> TYPE: PRT
<213> ORGANISM: Artificial Sequence
<220> FEATURE:
<223> OTHER INFORMATION: Synthetic

<400> SEQUENCE: 15

Ala Cys Ala Gly Cys Cys Ala Gly Cys Ala Cys Ala Cys Cys Cys Thr
1               5                   10                  15

Thr Gly

<210> SEQ ID NO 16
<211> LENGTH: 20
<212> TYPE: PRT
<213> ORGANISM: Artificial Sequence
<220> FEATURE:

```
<223> OTHER INFORMATION: Synthetic

<400> SEQUENCE: 16

Thr Thr Cys Thr Cys Thr Gly Ala Gly Cys Ala Ala Cys Ala Gly Cys
1               5                   10                  15

Thr Cys Cys Cys
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic

<400> SEQUENCE: 17

Ala Ala Ala Gly Cys Gly Thr Thr Ala Thr Thr Thr Gly Gly Ala
1               5                   10                  15

Thr Gly Gly Gly
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic

<400> SEQUENCE: 18

Ala Cys Ala Ala Gly Ala Gly Ala Ala Thr Thr Gly Gly Gly Ala Gly
1               5                   10                  15

Gly Gly Gly Thr
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Thr Cys Cys Ala Cys Gly Ala Ala Gly Gly Thr Cys Thr Cys Thr
1               5                   10                  15

Thr Cys Thr Cys
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Ala Gly Gly Ala Ala Gly Cys Thr Gly Gly Cys Ala Gly Ala Cys Cys
1               5                   10                  15

Ala Gly Thr Ala
            20

<210> SEQ ID NO 21
<211> LENGTH: 20
<212> TYPE: PRT
<213> ORGANISM: Artificial Sequence
```

<220> FEATURE:
<223> OTHER INFORMATION: Synthetic

<400> SEQUENCE: 21

Cys Ala Ala Cys Thr Thr Cys Thr Gly Cys Thr Ala Cys Thr Thr Cys
1               5                   10                  15

Cys Gly Cys Cys
            20

<210> SEQ ID NO 22
<211> LENGTH: 19
<212> TYPE: PRT
<213> ORGANISM: Artificial Sequence
<220> FEATURE:
<223> OTHER INFORMATION: Synthetic

<400> SEQUENCE: 22

Cys Gly Ala Gly Gly Cys Ala Cys Thr Thr Thr Gly Ala Thr Gly Ala
1               5                   10                  15

Ala Gly Cys

<210> SEQ ID NO 23
<211> LENGTH: 20
<212> TYPE: PRT
<213> ORGANISM: Artificial Sequence
<220> FEATURE:
<223> OTHER INFORMATION: Synthetic

<400> SEQUENCE: 23

Ala Ala Thr Gly Ala Ala Gly Gly Gly Gly Thr Cys Ala Thr Thr Gly
1               5                   10                  15

Ala Thr Gly Gly
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Ala Ala Gly Gly Thr Gly Ala Ala Gly Gly Thr Cys Gly Gly Ala Gly
1               5                   10                  15

Thr Cys Ala Ala
            20

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Gly Cys Cys Thr Thr Thr Cys Cys Gly Ala Gly Gly Ala Gly Gly Ala
1               5                   10                  15

Gly Ala Cys

<210> SEQ ID NO 26
<211> LENGTH: 20
<212> TYPE: PRT
<213> ORGANISM: Artificial Sequence
<220> FEATURE:

<223> OTHER INFORMATION: Synthetic

<400> SEQUENCE: 26

Thr Cys Thr Gly Thr Gly Ala Cys Gly Gly Ala Thr Cys Thr Gly Cys
1               5                   10                  15

Ala Cys Thr Cys
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

Gly Ala Cys Ala Gly Cys Ala Ala Ala Gly Cys Ala Cys Thr Gly Thr
1               5                   10                  15

Gly Thr Gly Gly
            20

<210> SEQ ID NO 28
<211> LENGTH: 22
<212> TYPE: PRT
<213> ORGANISM: Artificial Sequence
<220> FEATURE:
<223> OTHER INFORMATION: Synthetic

<400> SEQUENCE: 28

Thr Cys Ala Gly Cys Ala Cys Thr Thr Ala Ala Ala Ala Gly Ala Thr
1               5                   10                  15

Thr Cys Cys Gly Thr Gly
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic

<400> SEQUENCE: 29

Gly Cys Ala Cys Cys Ala Ala Cys Gly Ala Cys Ala Gly Gly Ala Ala
1               5                   10                  15

Gly Gly Ala Thr Gly Ala Gly
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic

<400> SEQUENCE: 30

Cys Ala Cys Gly Thr Thr Cys Cys Ala Gly Ala Gly Cys Cys Gly Gly
1               5                   10                  15

Ala Cys Ala Thr
            20

<210> SEQ ID NO 31
<211> LENGTH: 18
<212> TYPE: PRT
<213> ORGANISM: Artificial Sequence

```
<220> FEATURE:
<223> OTHER INFORMATION: Synthetic

<400> SEQUENCE: 31

Cys Thr Cys Ala Thr Gly Thr Thr Cys Ala Thr Gly Cys Cys Gly Cys
1               5                   10                  15

Thr Cys

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Gly Ala Cys Ala Cys Cys Ala Thr Gly Ala Gly Ala Ala Cys Ala
1               5                   10                  15

Gly Cys Gly

<210> SEQ ID NO 33
<211> LENGTH: 20
<212> TYPE: PRT
<213> ORGANISM: Artificial Sequence
<220> FEATURE:
<223> OTHER INFORMATION: Synthetic

<400> SEQUENCE: 33

Cys Ala Cys Ala Gly Thr Gly Ala Cys Cys Ala Cys Gly Thr Cys Gly
1               5                   10                  15

Ala Thr Thr Thr
        20

<210> SEQ ID NO 34
<211> LENGTH: 20
<212> TYPE: PRT
<213> ORGANISM: Artificial Sequence
<220> FEATURE:
<223> OTHER INFORMATION: Synthetic

<400> SEQUENCE: 34

Cys Ala Cys Ala Ala Gly Gly Cys Cys Cys Thr Cys Ala Gly Thr Ala
1               5                   10                  15

Cys Cys Thr Cys
        20

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Cys Cys Ala Cys Ala Gly Thr Ala Cys Ala Cys Gly Ala Ala Cys Cys
1               5                   10                  15

Thr Gly Gly Gly
        20

<210> SEQ ID NO 36
<211> LENGTH: 21
<212> TYPE: PRT
<213> ORGANISM: Artificial Sequence
<220> FEATURE:
```

```
<223> OTHER INFORMATION: Synthetic

<400> SEQUENCE: 36

Cys Cys Gly Thr Thr Cys Thr Gly Ala Ala Thr Cys Thr Gly Cys Thr
1               5                   10                  15

Gly Gly Thr Cys Cys
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic

<400> SEQUENCE: 37

Ala Thr Gly Ala Ala Ala Cys Thr Cys Gly Cys Thr Gly Thr Cys Ala
1               5                   10                  15

Cys Cys Cys Thr
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Gly Thr Thr Thr Cys Gly Ala Thr Gly Ala Cys Ala Cys Gly Cys Thr
1               5                   10                  15

Gly Ala Ala Ala
            20

<210> SEQ ID NO 39
<211> LENGTH: 21
<212> TYPE: PRT
<213> ORGANISM: Artificial Sequence
<220> FEATURE:
<223> OTHER INFORMATION: Synthetic

<400> SEQUENCE: 39

Cys Ala Gly Cys Ala Cys Thr Thr Thr Ala Ala Ala Gly Gly Ala Cys
1               5                   10                  15

Gly Gly Thr Gly Thr
            20

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Gly Gly Gly Thr Gly Thr Gly Thr Gly Gly Ala Cys Cys Ala Thr
1               5                   10                  15

Gly Thr

<210> SEQ ID NO 41
<211> LENGTH: 20
<212> TYPE: PRT
<213> ORGANISM: Artificial Sequence
<220> FEATURE:
```

<223> OTHER INFORMATION: Synthetic

<400> SEQUENCE: 41

Gly Cys Thr Thr Ala Gly Cys Cys Thr Cys Gly Thr Cys Gly Ala Thr
1               5                   10                  15

Gly Ala Ala Cys
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic

<400> SEQUENCE: 42

Ala Ala Cys Cys Cys Cys Ala Ala Gly Ala Thr Gly Cys Ala Cys Ala
1               5                   10                  15

Ala Cys Thr Cys
            20

<210> SEQ ID NO 43
<211> LENGTH: 19
<212> TYPE: PRT
<213> ORGANISM: Artificial Sequence
<220> FEATURE:
<223> OTHER INFORMATION: Synthetic

<400> SEQUENCE: 43

Gly Thr Ala Cys Cys Cys Gly Cys Ala Cys Thr Thr Gly Cys Ala Cys
1               5                   10                  15

Ala Ala Cys

<210> SEQ ID NO 44
<211> LENGTH: 20
<212> TYPE: PRT
<213> ORGANISM: Artificial Sequence
<220> FEATURE:
<223> OTHER INFORMATION: Synthetic

<400> SEQUENCE: 44

Ala Thr Thr Cys Cys Ala Cys Thr Thr Thr Gly Cys Gly Thr Thr Cys
1               5                   10                  15

Ala Ala Gly Gly
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic

<400> SEQUENCE: 45

Ala Gly Cys Ala Ala Ala Gly Ala Gly Thr Cys Cys Thr Gly Ala
1               5                   10                  15

Thr Gly Gly Ala
            20

<210> SEQ ID NO 46
<211> LENGTH: 20
<212> TYPE: PRT
<213> ORGANISM: Artificial Sequence
<220> FEATURE:

-continued

<223> OTHER INFORMATION: Synthetic

<400> SEQUENCE: 46

Cys Gly Ala Thr Ala Ala Gly Ala Ala Gly Gly Cys Gly Thr Thr Thr
1               5                   10                  15

Cys Ala Gly Gly
            20

COMPOSITIONS AND METHODS FOR OBTAINING 3-DIMENSIONAL LUNG-LIKE EPITHELIUM AND RELATED USES THEREOF

This application claims priority to U.S. provisional application No. 62/513,191, filed May 31, 2017, the contents of which is herein incorporated by reference in its entirety.

STATEMENT REGARDING FEDERALLY SPONSORED RESEARCH OR DEVELOPMENT

This invention was made with government support under HL119215 awarded by the National Institutes of Health. The government has certain rights in the invention.

FIELD OF THE INVENTION

The invention disclosed herein generally relates to methods and systems for growing, expanding and/or obtaining 3-dimensional lung-like epithelium comprising cells having SOX9 protein activity and SOX2+ protein activity. In particular, the invention disclosed herein relates to methods and systems for growing human cells having SOX9 protein activity and SOX2+ protein activity in vitro, and for promoting pluripotent stem cell derived ventral-anterior foregut spheroid tissue into 3-dimensional lung-like epithelium comprising cells having SOX9 protein activity and SOX2+ protein activity.

INTRODUCTION

During development, the lung undergoes branching morphogenesis, where a series of stereotyped epithelial bifurcations give rise to the branched, tree-like architecture of the adult lung (Metzger et al., 2008). A population of rapidly proliferating progenitor cells resides at the distal tips of the epithelium throughout the branching process (Branchfield et al., 2015; Rawlins et al., 2009). Branching morphogenesis and maintenance of the distal tip progenitor cells is regulated by a series of complex mesenchymal-epithelial interactions that involve multiple signaling events, transcription factors, and dynamic regulation of the physical environment (Domyan and Sun, 2010; Hines and Sun, 2014; H. Y. Kim and Nelson, 2012; Morrisey et al., 2013; Morrisey and Hogan, 2010; Rawlins, 2010; Rock and Hogan, 2011; Varner and Nelson, 2014).

The molecular regulation of branching morphogenesis has been investigated in depth, with genetic mouse models playing a central role. These studies have identified major roles for several signaling events, including Wnt, Fibroblast Growth Factor (Fgf), Bone Morphogenic Protein (Bmp), Sonic Hedgehog (Shh), Retinoic Acid (RA) and Hippo signaling among others (Abler et al., 2009; Bellusci et al., 1997a; 1997b; 1996; Cornett et al., 2013; Desai et al., 2006; 2004; Domyan et al., 2011; Goss et al., 2009; Harris-Johnson et al., 2009; Herriges et al., 2015; Lange et al., 2015; Lu et al., 2009; Mahoney et al., 2014; Motoyama et al., 1998; Sekine et al., 1999; Shu et al., 2005; Weaver et al., 2000; White et al., 2006; Yin et al., 2011; 2008; Y. Zhang et al., 2016; Zhao et al., 2014). These studies have shown the importance of epithelial-mesenchymal cross talk for regulating processes such as branching morphogenesis and proximal-distal patterning (Morrisey and Hogan, 2010), and due to the complex and intertwined nature of these signaling networks, perturbations in one pathway affect signaling activity of others (Hines and Sun, 2014; Morrisey et al., 2013; Ornitz and Yin, 2012). This understanding of murine lung development has been used as a guide to direct differentiation of human pluripotent stem cells into lung lineages and 3-dimensional lung organoids (Dye et al., 2016a; 2015; Firth et al., 2014; Ghaedi et al., 2013; Gilpin et al., 2014a; Gotoh et al., 2014; Huang et al., 2013; Konishi et al., 2015; Longmire et al., 2012).

Despite the wealth of information gained from murine studies, significant gaps in our understanding of lung development remain, especially in the context of human lung development. For example, it remains unknown how closely developmental processes in the murine lung mirror human lung development. Furthermore, due to the interdependence of mesenchymal and epithelial cell types, and the complex signaling events that interact to control this process, the precise mechanisms that control distal tip progenitor cell maintenance and cell fate differentiation have remained elusive.

These unknowns have been highlighted in studies that have attempted to differentiate lung lineages from hPSCs (Dye et al., 2015). For example, it has been shown that hPSCs can be differentiated into human lung organoids (HLOs) that possess airway-like epithelial structures, but it is not clear if HLOs pass through distal-tip progenitor-like stage, mimicking the normal developmental events in vivo. This gap in knowledge also suggests that robustly predicting cellular outcomes during hPSC-differentiation is still a major challenge. This lack of predictive power may be due, in part, to species-specific differences between the mouse and human lung, to a poor understanding of human fetal lung development, or because the environment controlling the distal-tip progenitor cells is so complex.

An improved understanding of such information is needed.

SUMMARY OF THE INVENTION

During mouse lung branching morphogenesis, a multipotent progenitor population resides at the tips of bifurcating epithelial tubes that give rise to all lung epithelial cell types (Rawlins et al., 2009); however, little is known about this population of progenitor cells in the developing human lung.

The present invention addresses this lack of knowledge. Indeed, experiments conducted during the course of developing embodiments for the present invention used developing mouse and human distal lung bud tip epithelial progenitors cultured in vitro in order to identify factors that promote tissue expansion and maintenance of progenitor identity. Such experimental results show that synergistic activation of FGF, WNT and RA signaling promoted growth, expansion and maintenance of SOX9+ distal lung-bud progenitor cells in vitro in mice and human tissue. Such experiments also identified unique species-specific differences where human progenitors co-express SOX9 and SOX2. When applied to human pluripotent stem cell (hPSC)-derived foregut spheroids, it was observed that FGF/WNT/RA induced a 3-dimensional lung-like epithelium, which possessed a robust population of SOX9+/SOX2+ distal lung progenitor-like cells. In addition to gene-protein expression differences between mice and human tissue, results also showed significant differences in the functional response to dynamic changes in the growth factor signaling environment when comparing the two species. Such results represent improved understanding of the mechanisms regulating progenitor cell identity in the human lung, and demonstrates that a robust signaling environment supportive of human fetal lung progenitors can induce a similar population in hPSC-derived tissues.

Accordingly, the invention disclosed herein generally relates to methods and systems for growing, expanding and/or obtaining 3-dimensional lung-like epithelium comprising cells having SOX9 protein activity and SOX2+ protein activity. In particular, the invention disclosed herein relates to methods and systems for growing human cells having SOX9 protein activity and SOX2+ protein activity in vitro, and for promoting pluripotent stem cell derived ventral-anterior foregut spheroid tissue into 3-dimensional lung-like epithelium comprising cells having SOX9 protein activity and SOX2+ protein activity.

In certain embodiments, the present invention provides methods of inducing formation of 3-dimensional lung tissue, comprising culturing cells isolated from a human lung or cells from the ventral-anterior foregut spheroid tissue derived from pluripotent stem cells in vitro, wherein the culturing results in differentiation of the cells isolated from a human lung or the cells from the ventral-anterior foregut spheroid tissue derived from pluripotent stem cells into tissue comprising 3-dimensional lung-like epithelium having SOX9 and SOX2+ activity, wherein the culturing results in activation of one or more signaling pathways selected from the FGF signaling pathway, the retinoic acid signaling pathway, and the Wnt signaling pathway; and obtaining 3-dimensional lung tissue from the cultured tissue comprising 3-dimensional lung-like epithelium.

In certain embodiments, the present invention provides methods of treating a mammalian subject having a damaged lung tissue with reduced function by engrafting at the site of injury one or more of 1) a composition comprising ex vivo 3-dimensional lung-like epithelium comprising cells having SOX9 protein activity and SOX2+ protein activity, 2) a composition comprising in vitro hPSC-derived ventral-anterior foregut spheroid tissue differentiated into tissue comprising 3-dimensional lung-like epithelium comprising cells having SOX9 protein activity and SOX2+ protein activity, and 3) a composition comprising differentiated derivatives of 3-dimensional lung-like epithelium comprising cells having SOX9 protein activity and SOX2+ protein activity.

In some embodiments, the methods comprise the steps of administering the ex vivo cells to the subject, wherein the ex vivo cells engraft at the site of injury and repopulate at least a portion of the site with the ex vivo cells, wherein the repopulated ex vivo cells supplement the function, thereby treating the subject.

In certain embodiments, the present invention provides methods of treating a mammalian subject having a damaged lung tissue with reduced function, comprising:
a) culturing cells isolated from a human lung or cells from the ventral-anterior foregut spheroid tissue derived from pluripotent stem cells in vitro, wherein the culturing results in differentiation of the cells isolated from a human lung or the cells from the ventral-anterior foregut spheroid tissue derived from pluripotent stem cells into tissue comprising 3-dimensional lung-like epithelium, wherein the culturing comprises activating one or more signaling pathways selected from the FGF signaling pathway, the retinoic acid signaling pathway, and the Wnt signaling pathway;
b) obtaining 3-dimensional lung tissue from the cultured tissue comprising 3-dimensional lung-like epithelium;
c) engrafting the obtained 3-dimensional lung-like epithelium at the site of injury, wherein engrafted 3-dimensional lung-like epithelium engraft at the site of injury and repopulate at least a portion of the site with the engrafted cells, wherein the repopulated cells supplement the function, thereby treating the subject.

In some embodiments, the damaged lung tissue is associated with, but not limited to, a condition caused by injuries that result in loss of epithelial function (e.g., bronchiolitis obliterans). In some embodiments, the damaged lung tissue is associated with, but not limited to, post-lung transplant complications (e.g., bronchiolitis obliterans). In some embodiments, the damaged lung tissue is associated with, but not limited to, a genetic disorder (e.g., mutations that cause an impairment or a loss of epithelial cell function (e.g., cystic fibrosis)).

In some embodiments for such methods, the obtained tissue comprising 3-dimensional lung-like epithelium comprises cells having SOX9 protein activity and SOX2+ protein activity.

Such methods are not limited to a particular manner of activating the Wnt signaling pathway. In some embodiments, activating the Wnt signaling pathway comprises culturing the ventral-anterior foregut spheroid tissue with a small molecule or agonist that activates the Wnt signaling pathway. In some embodiments, the small molecule or agonist that activates the Wnt signaling pathway is CHIR99021. In some embodiments, activating the Wnt signaling pathway occurs through culturing the ventral-anterior foregut spheroid tissue with one or more molecules configured to activate a Wnt protein, wherein the Wnt protein is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

Such methods are not limited to a particular manner of activating the FGF signaling pathway. In some embodiments, activating the FGF signaling pathway comprises culturing the ventral-anterior foregut spheroid tissue with a small molecule or agonist that activates the FGF signaling pathway. In some embodiments, the small molecule or agonist that activates the FGF signaling pathway is selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23.

Such methods are not limited to a particular manner of activating the RA signaling pathway. In some embodiments, activating the RA signaling pathway comprises culturing the ventral-anterior foregut spheroid tissue with a small molecule or agonist that activates the RA signaling pathway. In some embodiments, the small molecule or agonist that activates the RA signaling pathway is all-trans retinoic acid. In some embodiments, the small molecule or agonist that activates the RA signaling pathway is AC 261066 (RARβ2 agonist), AC 55649 (selective RARβ2 agonist), adapalene (RARβ and RARγ agonist), AM 580 (retinoic acid analog; RARα agonist), AM 80 (RARα agonist; anticancer), BMS 753 (RARα-selective agonist), BMS 961 (selective RARγ agonist), CD 1530 (potent and selective RARγ agonist), CD 2314 (selective RARβ agonist), CD 437 (RARγ-selective agonist), Ch 55 (potent RAR agonist), isotretinoin (endogenous agonist for retinoic acid receptors), tazarotene (receptor-selective retinoid; binds RARβ and RARγ), and TTNPB (retinoic acid analog; RAR agonist).

In some embodiments, the ventral-anterior foregut spheroid tissue is derived from definitive endoderm cells. In some embodiments, the definitive endoderm cells are derived from pluripotent stem cells. In some embodiments, the pluripotent stem cells are embryonic stem cells and/or induced pluripotent stem cells and/or or cells obtained through somatic cell nuclear transfer.

In some embodiments, the culturing and obtaining steps are conducted in vitro.

In certain embodiments, the present invention provides compositions comprising 3-dimensional lung-like epithelium. In some embodiments, the 3-dimensional lung-like epithelium comprises cells having SOX9 protein activity and SOX2+ protein activity.

In certain embodiments, the present invention provides kits comprising 3-dimensional lung-like epithelium produced in vitro from the described methods.

In certain embodiments, the present invention provides differentiation-inducing culture medium kits for inducing cells isolated from a human lung or cells from ventral-anterior foregut spheroid tissue into 3-dimensional lung-like epithelium comprising cells having SOX9 protein activity and SOX2+ protein activity, the kit comprising (i) a differentiation-inducing culture medium, and (ii) a small molecule or agonist that activates the Wnt signaling pathway (e.g., CHIR99021), a small molecule or agonist that activates the FGF signaling pathway (e.g., FGF7), a small molecule or agonist that activates the RA signaling pathway (e.g., all-trans retinoic acid).

BRIEF DESCRIPTION OF DRAWINGS

FIG. 1A: FGF7 supports growth and is permissive for differentiation of mouse embryonic lung distal-tip progenitors. Schematic of Sox9-eGFP distal lung buds dissected at E13.5 and cultured in a Matrigel droplet.

FIG. 1B: Low magnification images of isolated lung buds under brightfield (left) or showing Sox9-eGFP expression (right). Scale bar represents 200 um.

FIG. 1C: Buds were cultured in basal media or individually with different factors (10 ng/mL FGF7, 10 ng/mL FGF10, 10 ng/mL BMP4, 50 nM RA, 3 uM CHIR-99021) and imaged at Day 0, Day 5 and Day 14 in culture. Scale bar represents 200 um.

(A, B, C, D, H, I, J) Statistically significant variation between the means of experimental groups within each experiment was determined by an unpaired, one-way analysis of variance in which the mean of each group was compared to the mean of every other group. A significance level of 0.05 was used. Significance is shown on the graph according to the following: P>0.05 ns, P≤0.05*, P≤0.01, P≤0.001*, P≤0.0001****.

Figure 5A:
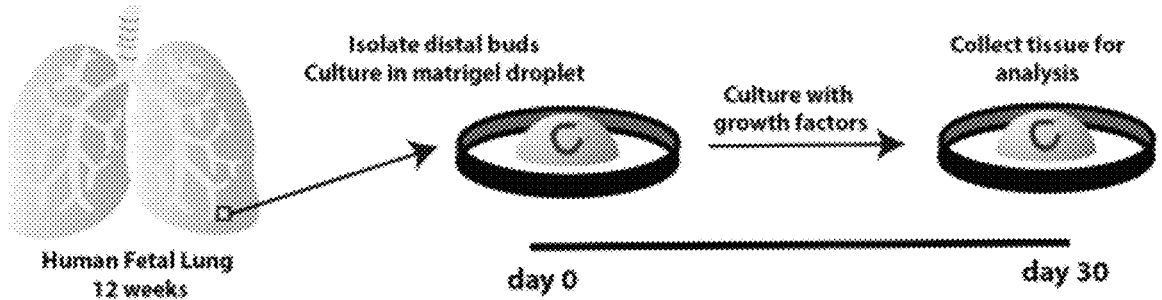
Figure 5B:
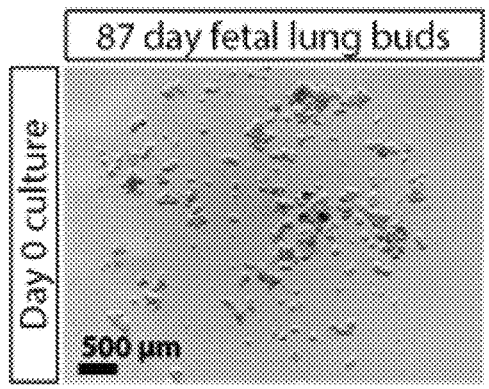

FIG. 5A-B: Synergistic activity of FGF7, CHIR-99021 and RA expands and maintains distal tip-progenitor cells in human fetal lung buds cultured ex vivo. Distal epithelial lung bud tips were collected from ~12 week old human fetal lungs and cultured in Matrigel. Scalebar in (B) represents 500 um.

Figure 5C:
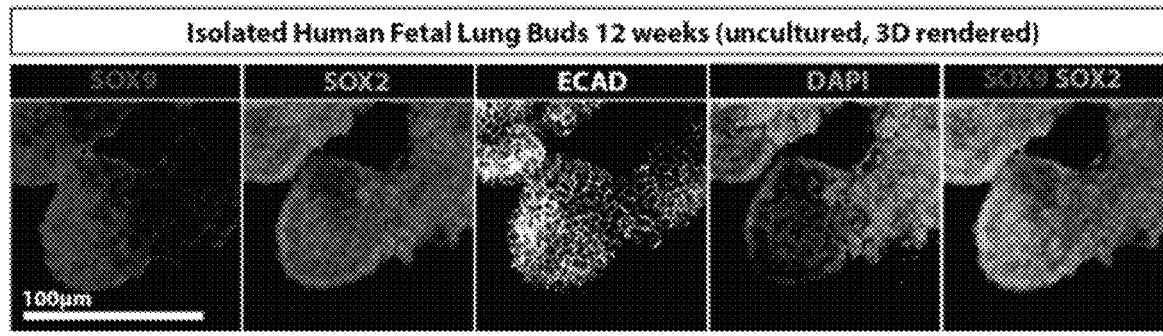

FIG. 5C: Freshly isolated buds were immunostained for SOX9, SOX2, ECAD and DAPI and wholemount imaged. Z-stacks were 3D rendered, and resulting images demonstrated overlapping SOX2 and SOX9 expression at bud tips. Scalebar represents 100 um.

Figure 5D:
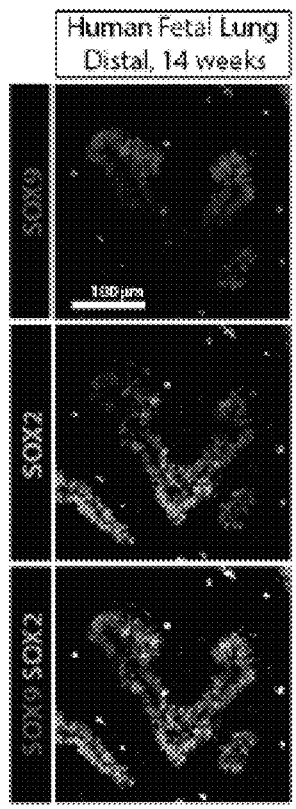

FIG. 5D: Overlapping SOX9/SOX2 protein expression at distal bud tips was confirmed in formalin fixed, paraffin embedded sections from a 14 week old human fetal lung specimen.

Figure 5E:
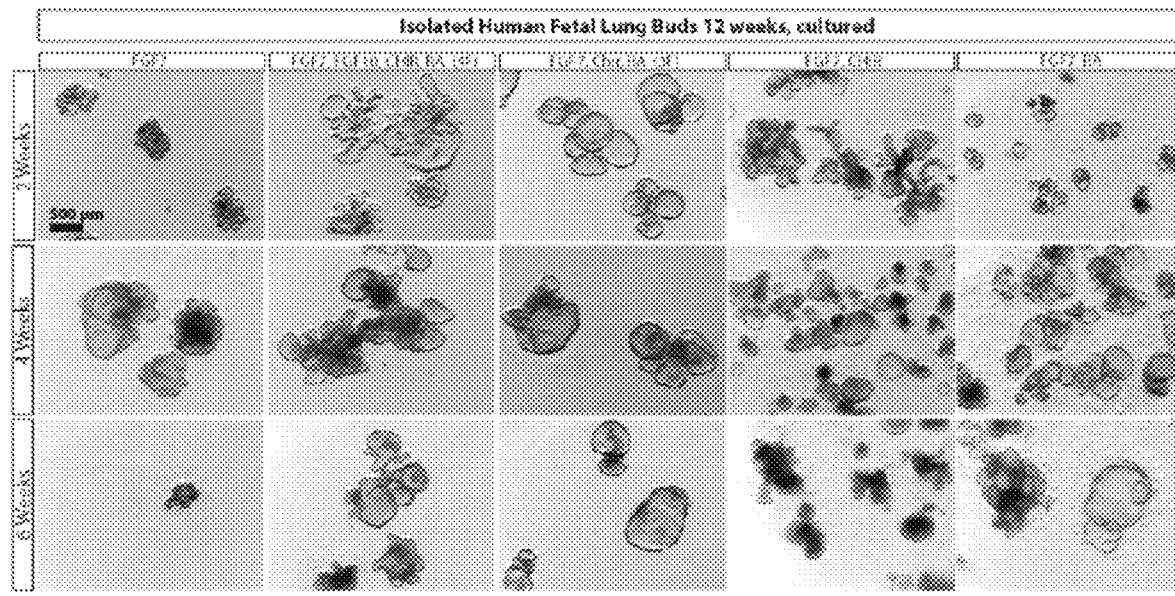

FIG. 5E: Isolated human fetal lung buds were cultured for over 6 weeks various media combinations (optimized in mouse lung bud cultures as shown in FIGS. 1 and 3) to determine conditions that supported tissue growth/expansion. FGF7 alone supported an initial expansion of buds, but the tissue stopped expanding beyond the 4 week period. All other combinations appeared to support robust lung bud expansion up to 6 weeks in culture. Scale bar represents 500 um.

Figure 5F:
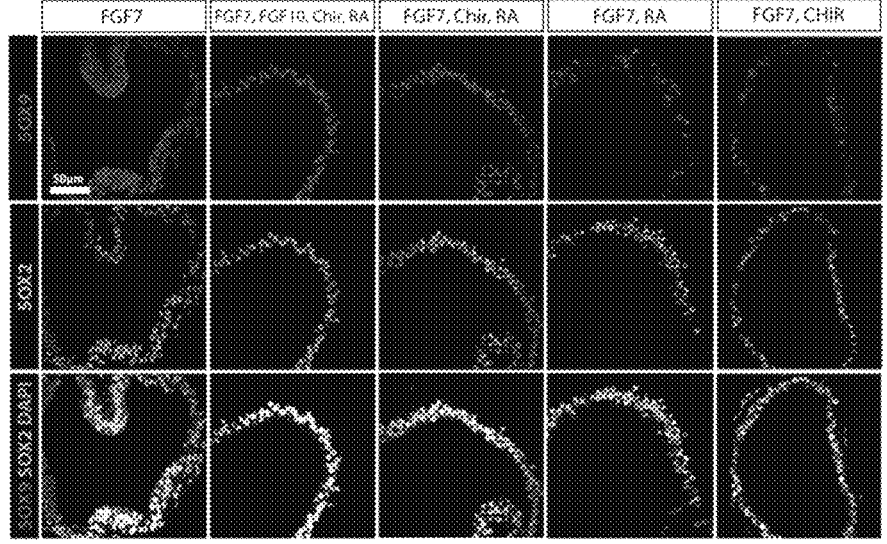
Figure 5G:
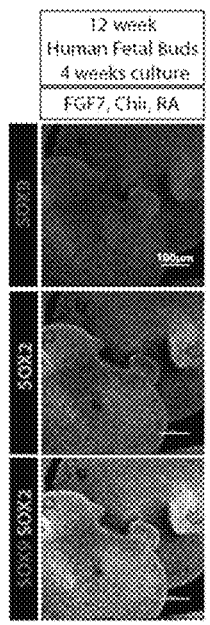

FIG. 5F-G: Immunostaining in sections (F) or in wholemount (G) demonstrated that lung buds expanded in 3F or 4F media after 4 weeks in vitro maintained robust co-expression of SOX9 and SOX2. FGF7 grown buds expressed both markers, but strong cytoplasmic SOX9 localization was observed. FGF7/CHIR-99021 and FGF7/RA conditions showed weak staining. Scalebar in (F) represents 50 um, and in (G) represents 100 um.

Figure 5H:
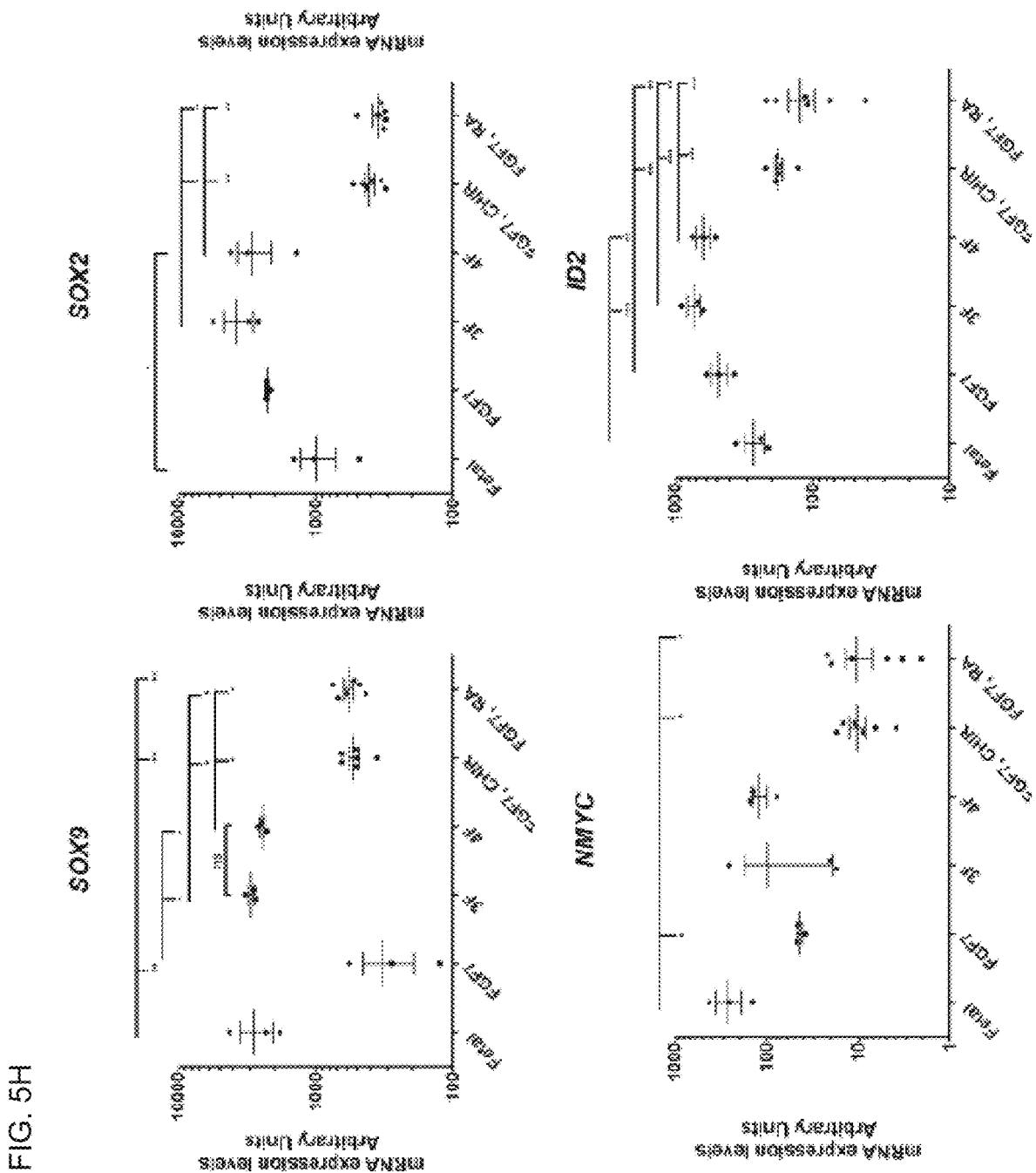

FIG. 5H: QRT-PCR analysis after 4 weeks in vitro showed that 3F and 4F conditions maintained the highest levels of SOX9, which were not significantly different from levels seen in the human fetal lung (H), while also maintaining robust expression of distal progenitor markers SOX2, NMYC and ID2 when compared to FGF7 alone, FGF7/CHIR-99021 or FGF7/RA. Each data point represents an independent biological replicate and graphs indicate the mean+/−the standard error of the mean for each experimental group. An unpaired, one-way analysis of variance was performed for each experiment followed by Tukey's multiple comparison to compare the mean of each group to the mean of every other group within the experiment. A significance level of 0.05 was used. Significance is shown on the graph according to the following: P>0.05 ns, P≤0.05*, P≤0.01, P≤0.001*, P≤0.0001****.

Figure 6A:
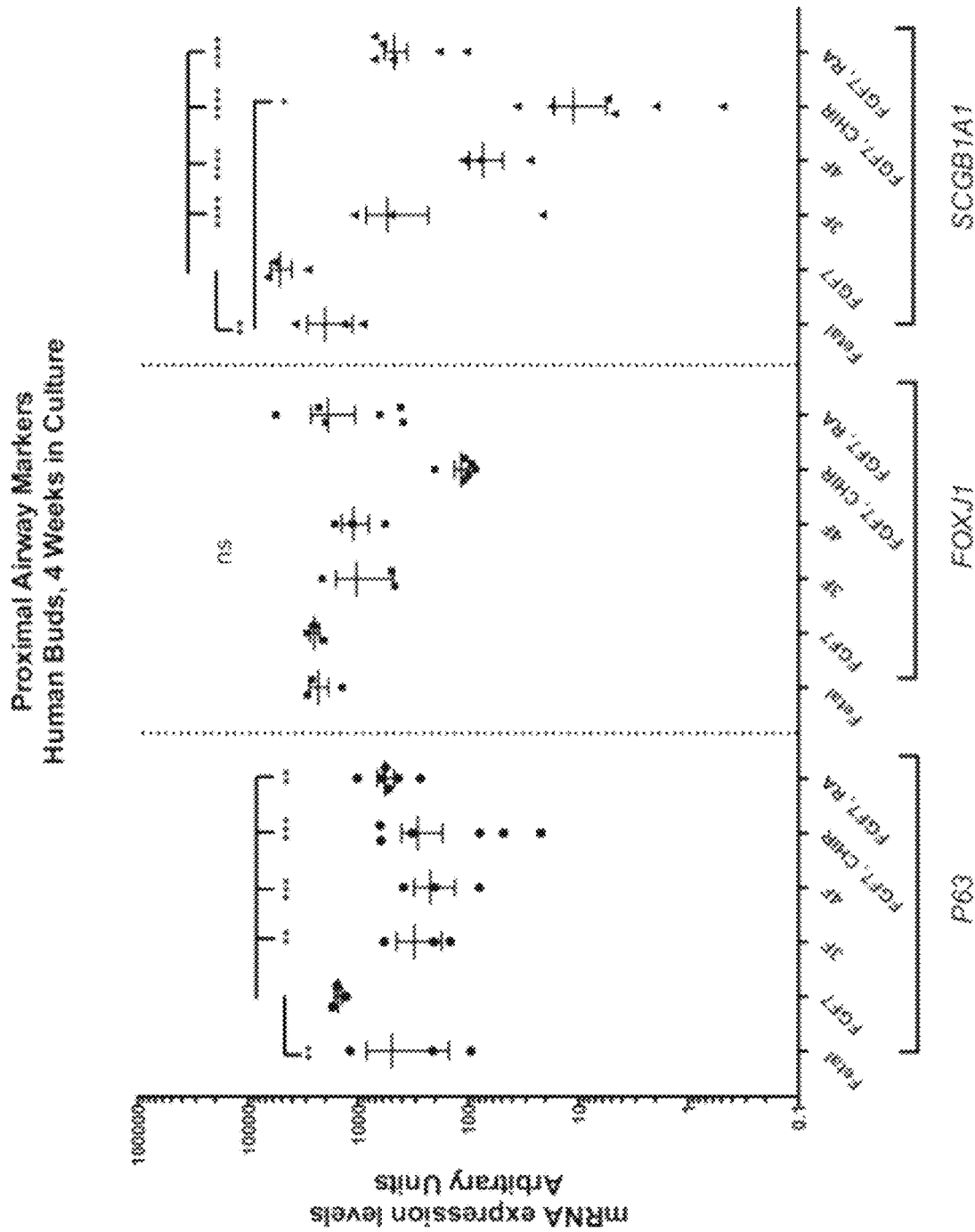

FIG. 6A: Characterizing human fetal lung buds in situ and in culture. Human fetal epithelial buds expanded in different media combinations were assessed for differentiation markers using QRT-PCR after 4 weeks in culture. FGF7-only media led to significantly increased expression of the proximal airway markers P63 and SCGB1A1 compared to the 14 week old human fetal lung (Fete), whereas treatment with 3F or 4F media kept the expression levels of mature proximal markers P63, FOXJ1 and SCGB1A1 at or below the levels seen in human fetal lung. Each data point represents an independent biological replicate.

Figure 6B:
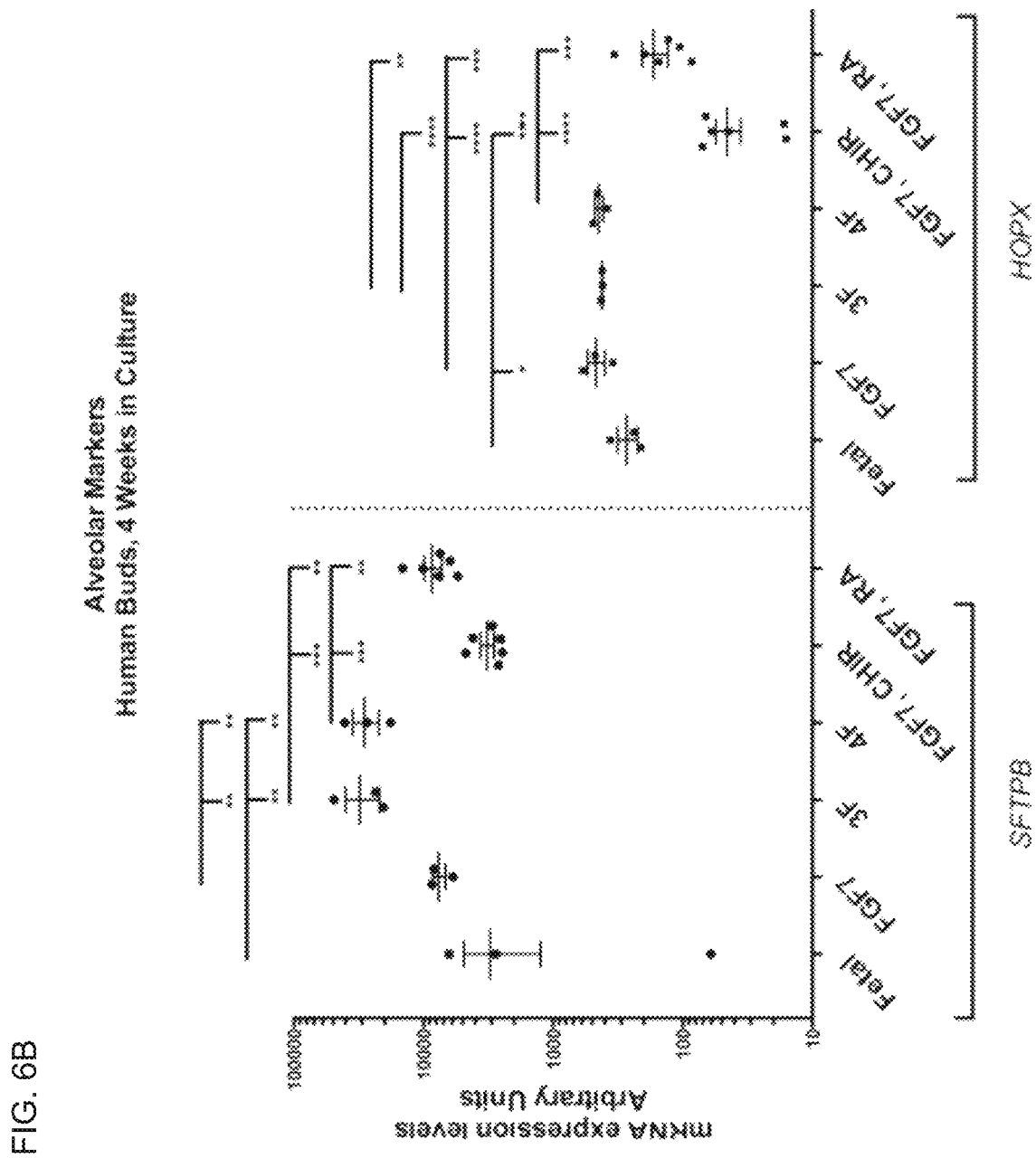

FIG. 6B: Treatment with 3F or 4F media significantly increased the expression of the AECII marker SFTPB compared to human fetal lung expression and FGF7-only, but did not lead to increased expression of the AECI marker HOPX.

(A, B) Each data point represents an independent biological replicate and graphs indicate the mean+/−the standard error of the mean for each experimental group. An unpaired, one-way analysis of variance was performed for each experiment followed by Tukey's multiple comparison to compare the mean of each group to the mean of every other group within the experiment. A significance level of 0.05 was used. Significance is shown on the graph according to the following: P>0.05 ns, P≤0.05*, P≤0.01, P≤0.001*, P≤0.0001****.

Figure 6C:
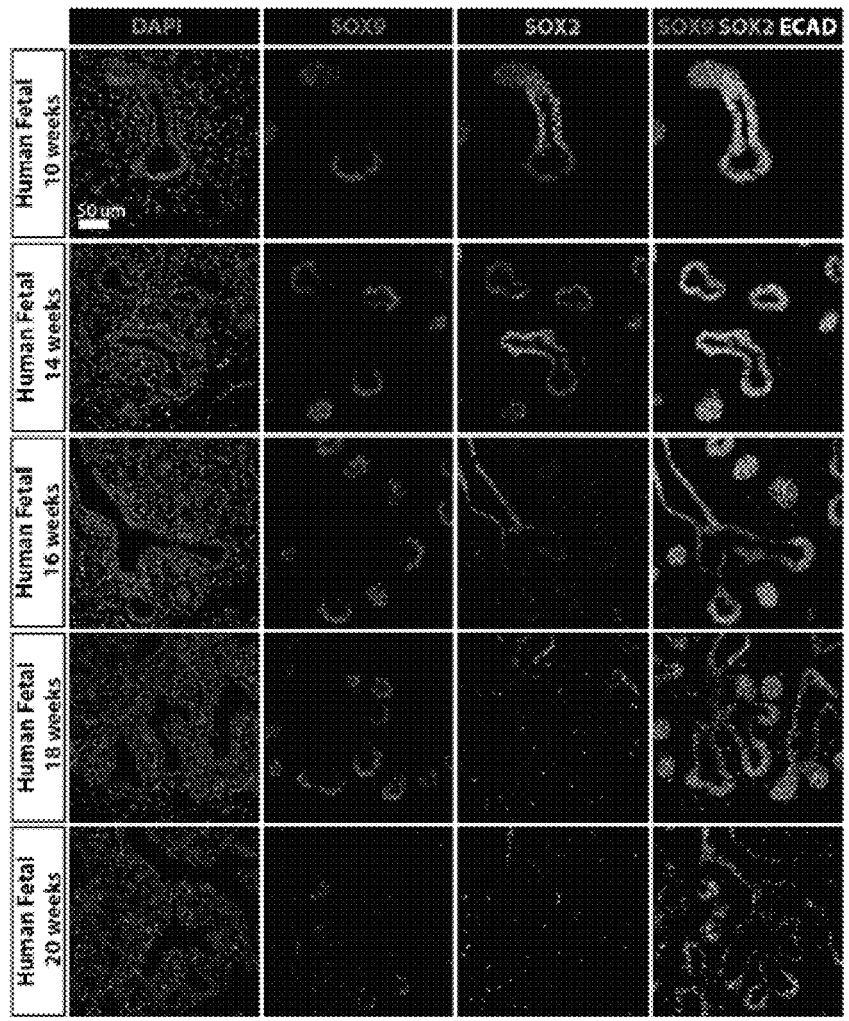

FIG. 6C: Paraffin embedded sections from human fetal lung specimens from 10-20 weeks demonstrate that distal epithelial progenitor regions are SOX9/SOX2 double-positive until 14 weeks, but lose this property sometime between 14 and 16 weeks gestation. By 16 weeks distal buds are SOX9+/SOX2− and a clear transition zone is established where cells are negative for both SOX2 and SOX9. Scale bar represents XXum.

Figure 6D:
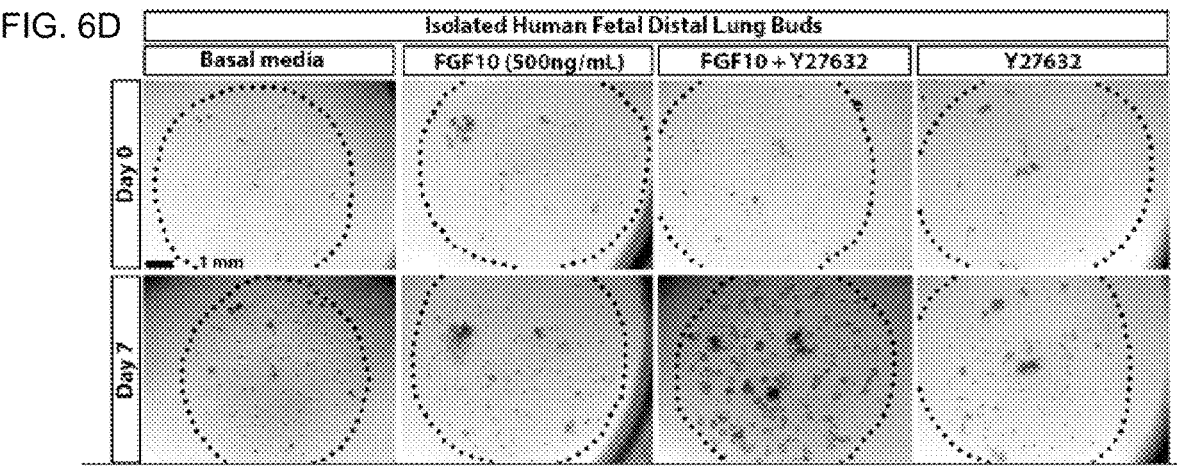

FIG. 6D: High concentrations of FGF10 do not lead to expansion of human fetal lung buds. Isolated tip-progenitors were cultured with in basal media or 500 ng/mL of FGF10. Bud tips were observed to form small cysts in FGF10 at this concentration; however, expansion of the tissue was not robust. Similarly, bud tips treated with the Rho-kinase (Rock) inhibitor Y27632 did not lead to tissue expansion; however, treatment with FGF10 (500 ng/mL) plus Y27632 led to robust cyst formation and tissue expansion. This indicated that the effect of high concentrations of FGF10 alone had limited effects on isolated human fetal buds. Dashed lines highlight the Matrigel droplet.

Figure 7A:
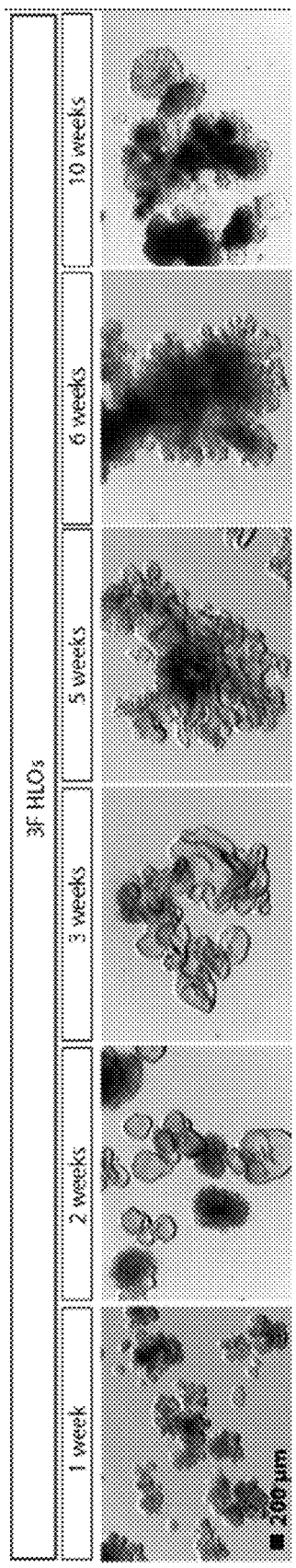
Figure 7B:
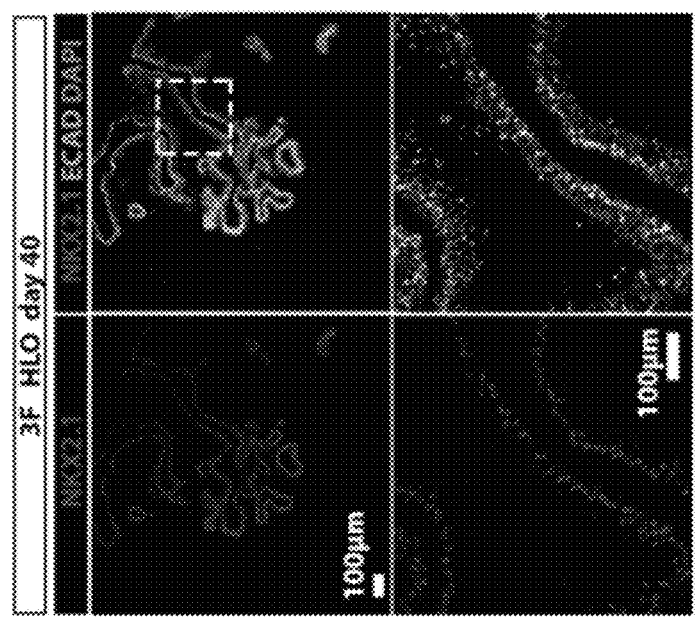

FIG. 7A-B: Synergistic activity of FGF7, CHIR-99021 and RA induces and maintains a population of distal lung tip-progenitor-like cells in hPSCs. Foregut spheroids were cultured with 3F media (FGF7, CHIR-99021 and RA) and brightfield images were collected over time in vitro. Spheroids exhibited stereotyped growth over time and resulted in highly complex epithelial structures, called Human Lung Organoid, grown in 3F media (3F HLOs). Scale bars represent 200 um. Note: In panel (B) the same spheroid is imaged for Day 1 through Day 9; however, representative images of different organoids are show on Day 14 and Day 45.

Figure 7C:
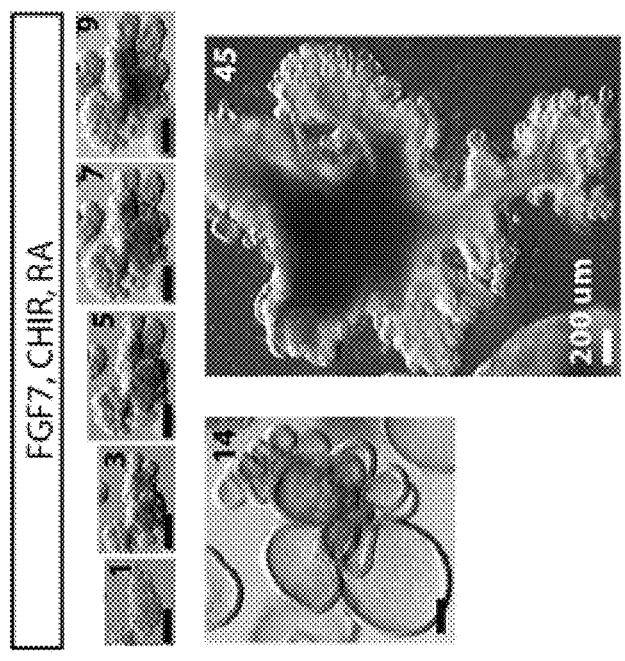

FIG. 7C: 3F HLOs exhibited robust NKX2.1 protein expression by immunofluorescence after 40 days in vitro, demonstrating a lung lineage. Scale bar represents 100 um.

Figure 7D:
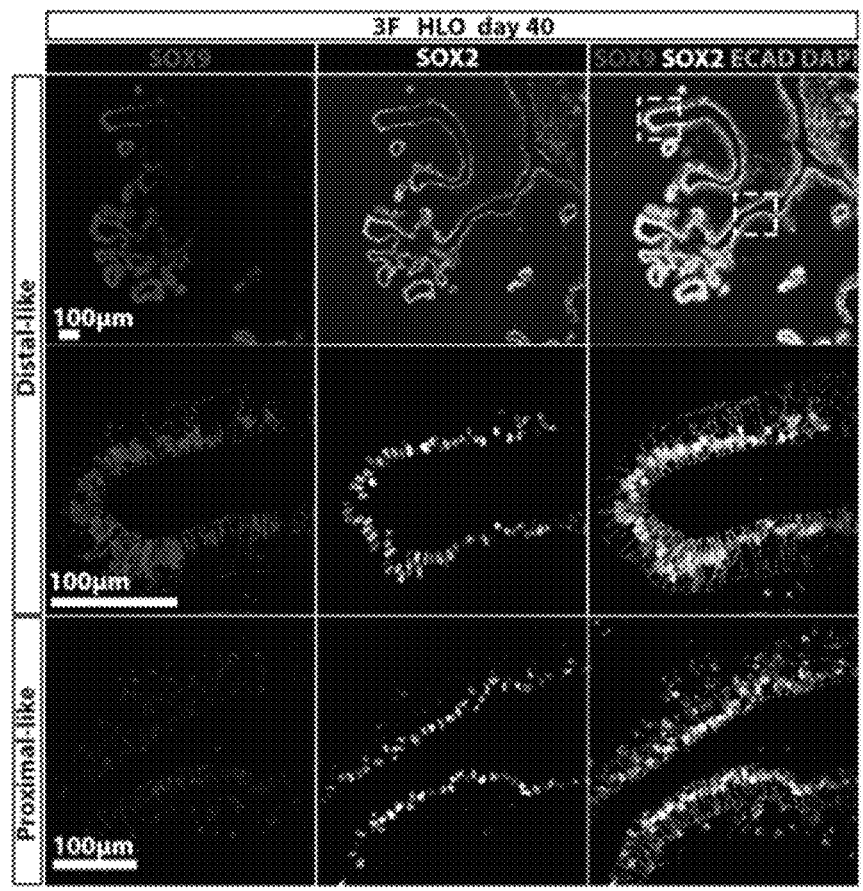

FIG. 7D: 3F HLOs exhibited and apparent proximal-distal patterning after 40 days in vitro, where immunofluorescence demonstrated that budded domains at the periphery of the 3D structure co-expressed SOX9/SOX2, consistent with the human fetal lung, and interior regions of the structures contained SOX2+ cells that were negative for SOX9. Scale bar represents 100 um.

Figure 7E:
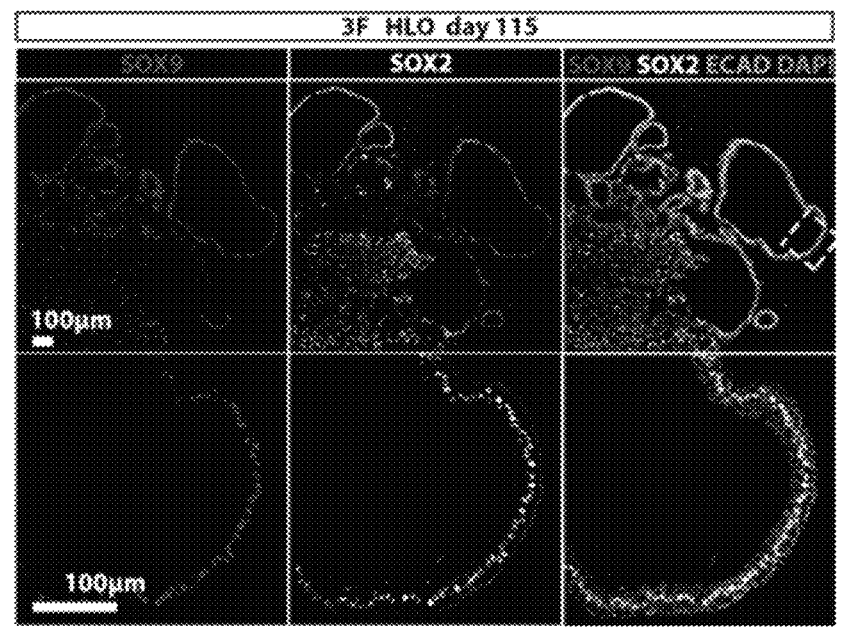

FIG. 7E: Immunofluorescence showed that SOX9/SOX2 double positive peripheral regions were maintained for up to 115 days in 3F media, Cellular debris can be seen within the lumen of the HLOs. Scale bar represents 100 um.

Figure 7F:
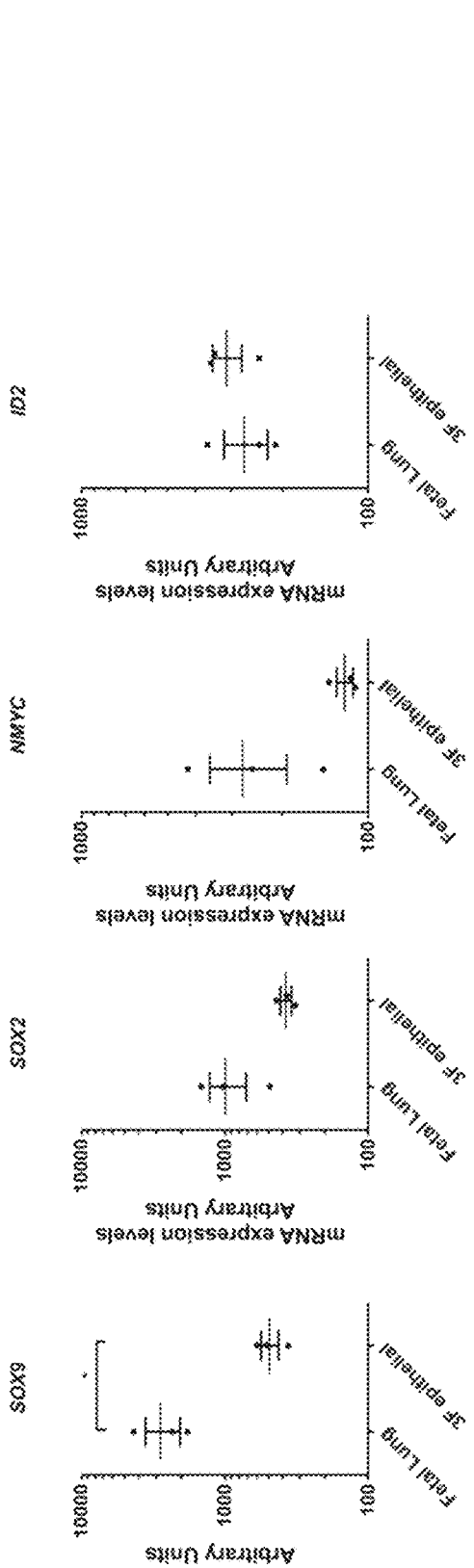

FIG. 7F: After 4 weeks in culture, 3F HLOs were compared to distal regions of the human fetal lung (epithelium plus mesenchyme) using QRT-PCR. 3F HLOs exhibited significantly lower levels of SOX9 transcript, but similar levels of other transcripts found in the human fetal lung, including NMYC, ID2 and SOX2. Each data point represents an independent biological replicate, and the graph shows the mean of each group+/−the standard error of the mean. For each target, means of each group were compared using a two-sided Student's T-test with a significance level of 0.05. Significance is shown on the graph according to the following: P>0.05 ns, P≤0.05*, P≤0.01, P≤0.001*, P≤0.0001****.

Figure 7G:
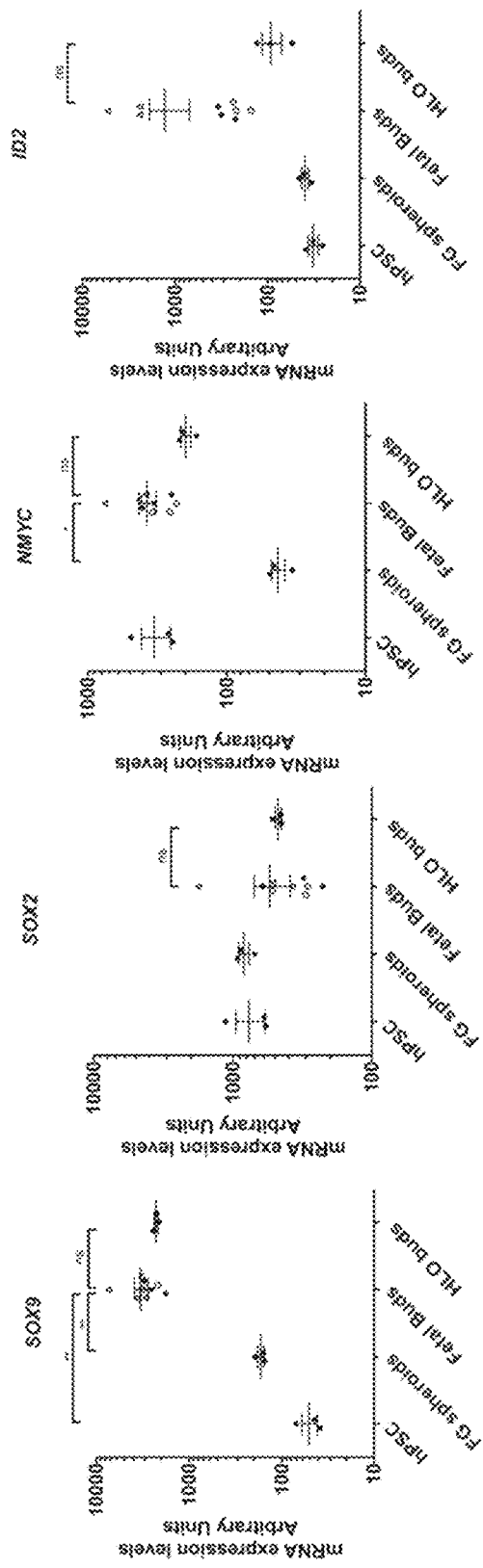

FIG. 7G: A QRT-PCR comparison was also performed between hPSCs, foregut (FG) spheroids, isolated human fetal buds and isolated peripheral budded regions from 3F HLOs (after 6 weeks in vitro). In this analysis, 3F HLOs and human fetal buds expressed similar levels of SOX9, SOX2, NMYC and ID2. Each data point represents an independent biological replicate. Different shapes indicate biological replicates in the human fetal bud sample, and each point for the same shape represents a technical replicates. The graph indicates the mean+/−the standard error of the mean for all values included within each experimental group. An unpaired one-way analysis of variance was performed followed by Tukey's multiple comparison test to compare the mean of each group to the mean of every other group for each target. A significance value of 0.05 was used. P>0.05 ns, P≤0.05*, P≤0.01, P≤0.001*, P≤0.0001****.

Figure 7H:
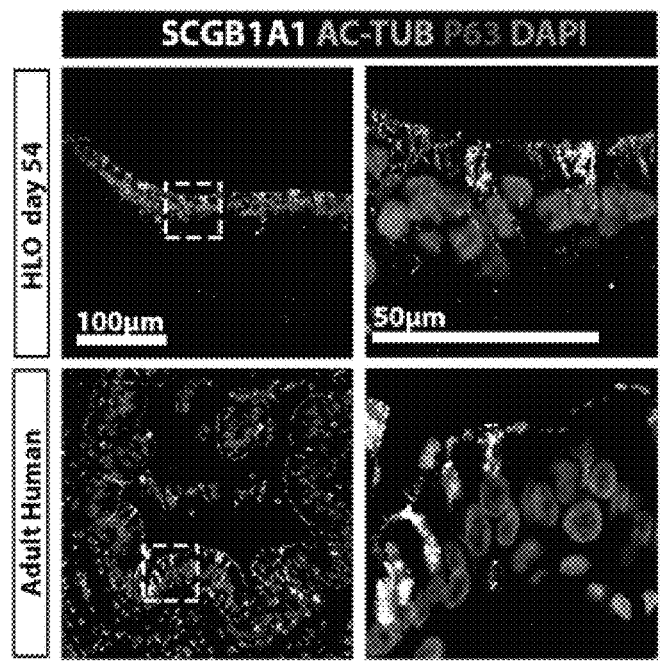
Figure 7I:
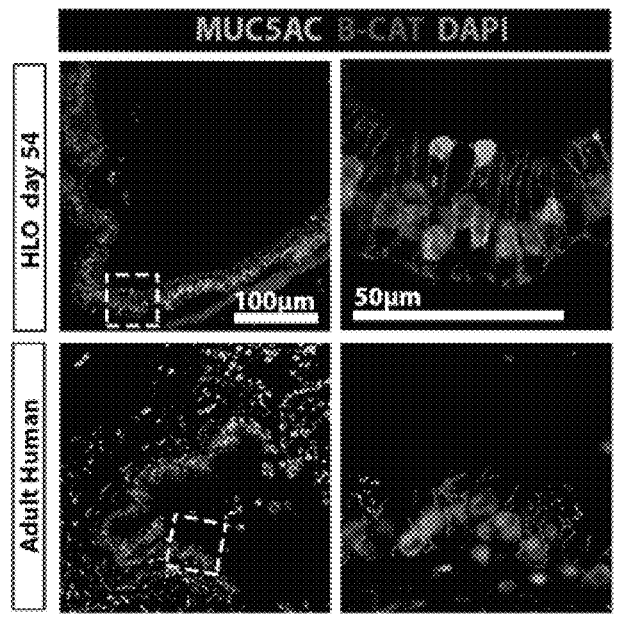
Figure 7J:
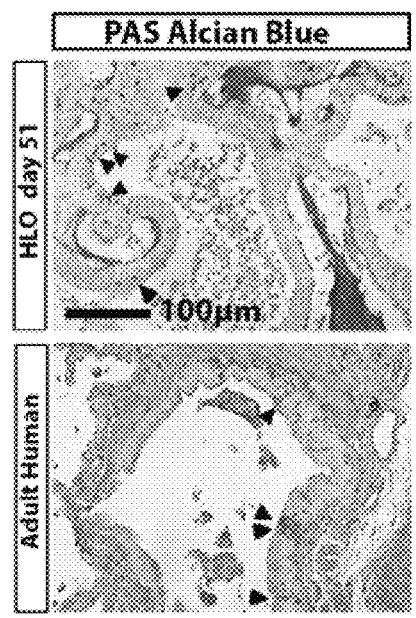

FIG. 7H-J: Interior regions of 3F HLOs (top row) possessed cells expressing markers of secretory cells, including SCGB1A1 (club cells) (H) and MUCSAC (goblet cells) (I) when compared to adult human airway tissue (bottom row). Notably, 3F HLOs lacked P63+ cells (H) and demonstrated AC-TUB staining, which was not localized to bona fide multiciliated structures (H). 3F HLOs also demonstrated evidence of goblet cells (arrowheads) and mucous secretion within the lumen as shown by PAS Alcian Blue staining (J). Scalebars in (H) represent 50 um and apply to low and high magnification images in (H) and (I), respectively. Scale bars in (J) represent 100 um.

Figure 8A:
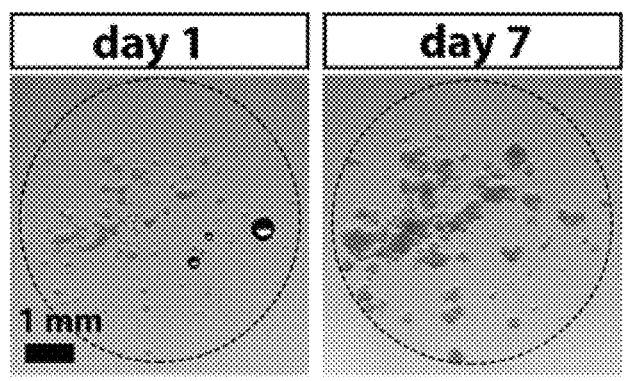
Figure 8B:
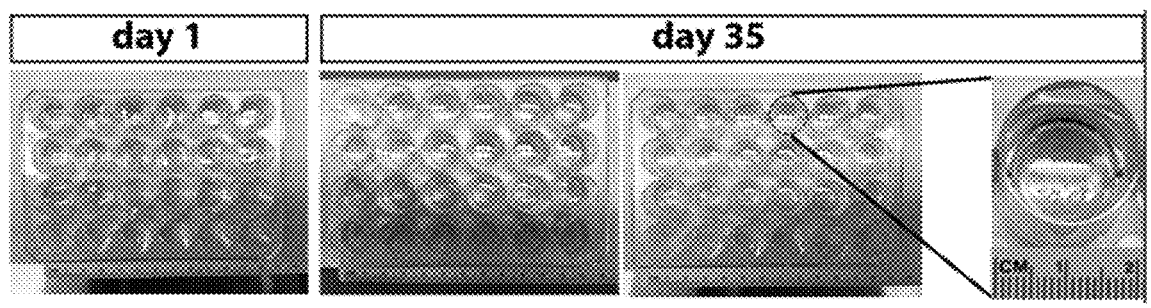

FIG. 8A-B: In vitro expansion, growth and passaging of 3F HLOs. Generation of 3F HLOs is robust. A single 24 well plate of hPSC cultures yield hundreds of foregut spheroids, which are expanded in Matrigel droplets in a new 24 well plate (A, B). Many foregut spheroids are placed into each droplet of Matrigel and expanded (A), and cultures grow substantially after 7 days (A) and are subsequently split into new Matrigel droplets every two weeks to provide room for growth and expansion (B). 3F HLOs are visible to the eye without a microscope by day 35 (B). Scale bar in (A) represents 1 mm.

Figure 8C:
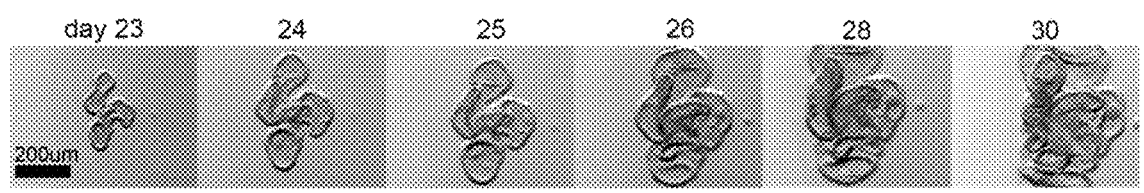
Figure 8D:
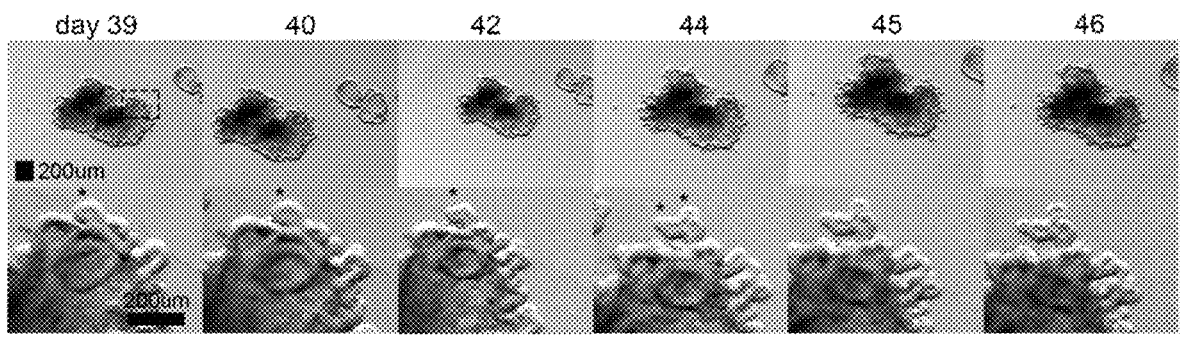

FIG. 8C-D: 3F HLOs undergo stereotyped growth, starting with epithelial expansion and folding from day ~20 through day ~35, followed by the emergence of bud-like domains and apparent bifurcation of bud tips (D). Asterisks indicate bud-like domains that appear to bifurcate over time. Scale bars in (C, D) represent 200 um.

Figure 8E:
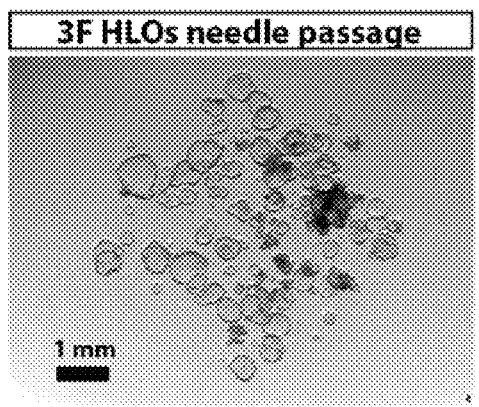
Figure 8F:
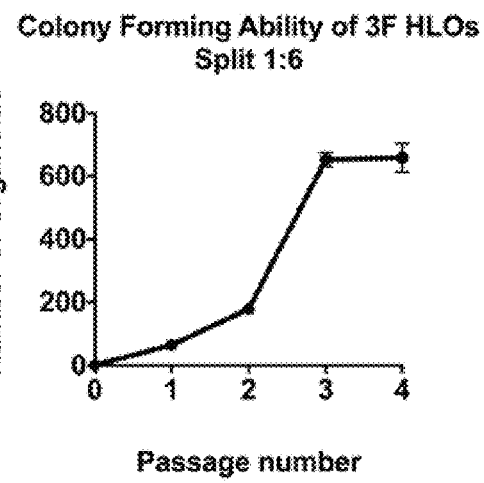
Figure 8G:
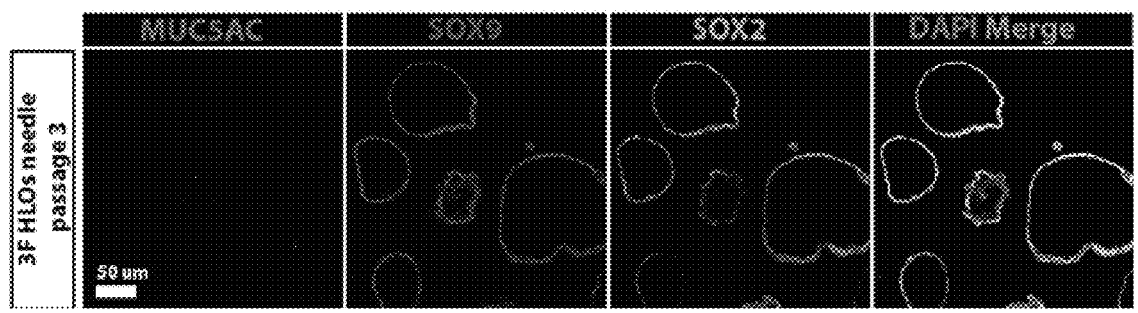

FIG. 8E-G: 3F HLOs can be serially split and expanded by mechanical shearing through a 27-gauge needle. Following passaging, 3F HLOs maintain a cystic structure (E), which allows for rapid expansion of the population (F). Error bars in F show the mean+/−the standard error of the mean. The majority HLOs resulting from needle passaging are double positive for SOX9 and SOX2 (G), suggesting a selection for the distal progenitor-like population. Scale bar in (E) represents 1 mm, and in (G) represents 50 um.

Figure 9A:
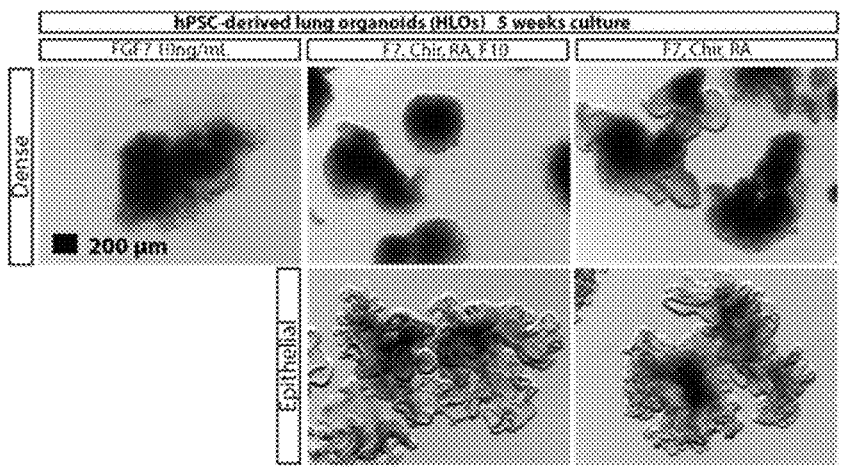
Figure 9B:
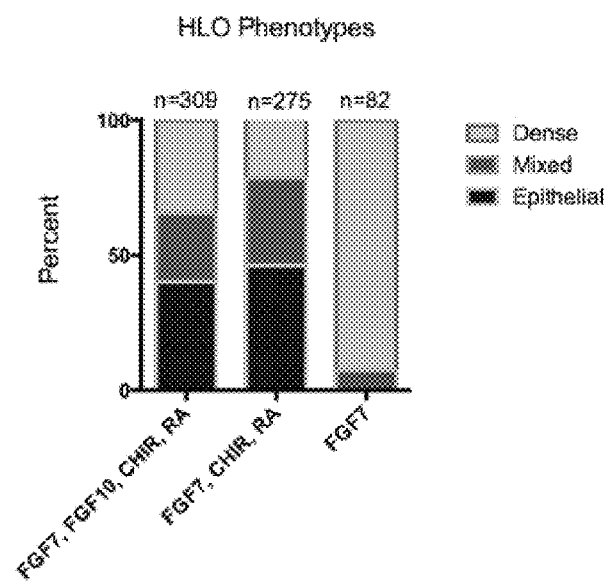

FIG. 9A-B: Characterizing 'epithelial' and 'dense' phenotypes in HLOs. HLOs exhibited 2 major phenotypes when grown in 3F media, termed 'epithelial' (as characterized in FIGS. 5, 7 and 10) and 'dense'. We also observed many HLOs that were a mix of these 2 phenotypes, termed 'mixed' (A). When grown in FGF7 alone, 90% of HLOs exhibited a 'dense' phenotype with no clear epithelial structures, whereas 5% of the FGF7 HLOs contained a clear epithelial phenotype (A, B). 3F and 4F media contained HLOs that were either entirely epithelial in nature, entirely 'dense', or mixed, in various proportions (A-B). Scale bar in (A) represents 200 um.

Figure 9C:
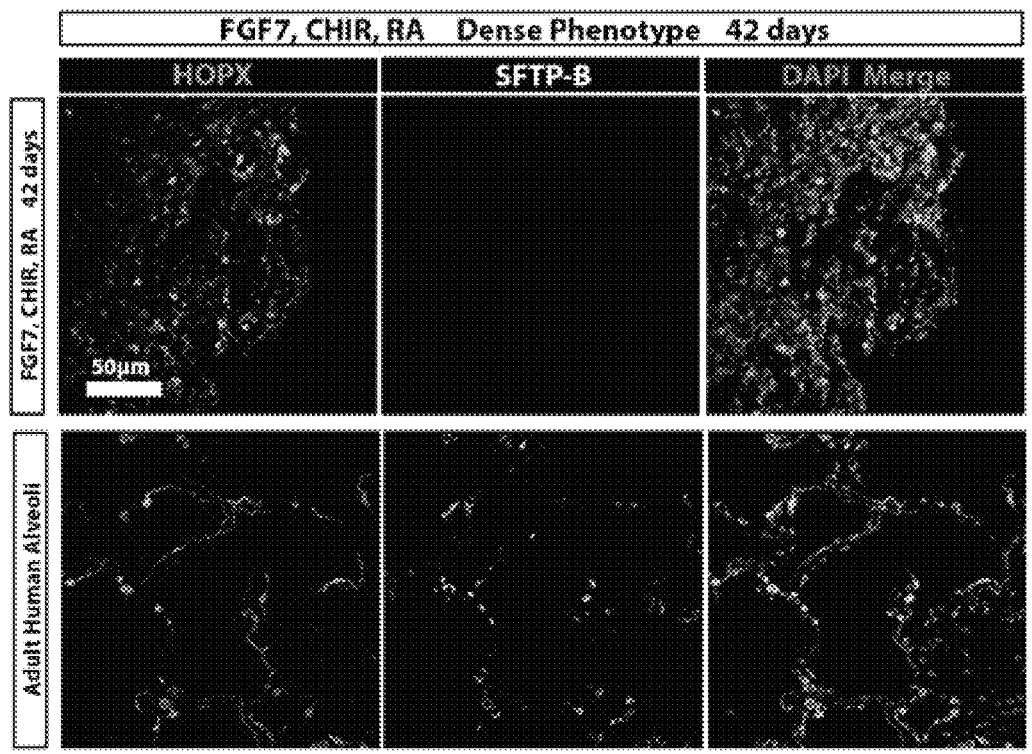
Figure 9D:
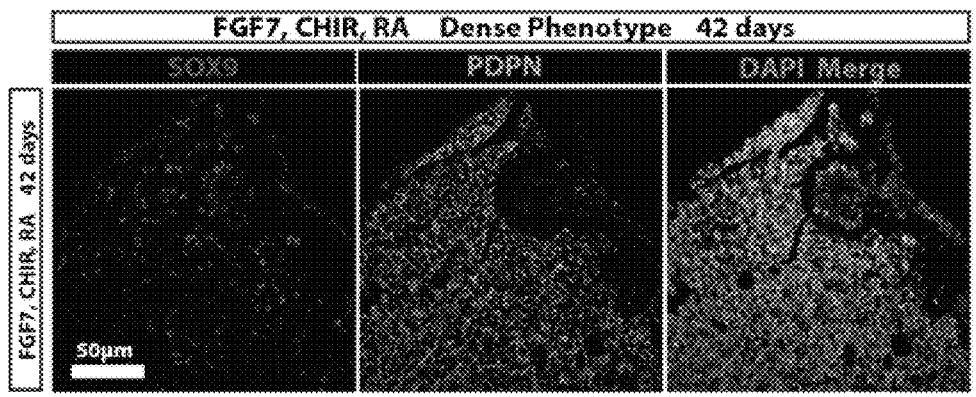

FIG. 9C-D: After 42 days in vitro, dense 3F HLOs were assessed by immunofluorescence. Dense 3F HLOs consisted predominantly of cells expressing the markers HOPX (C) and PDPN (D), which is consistent with AECI cells in the adult alveoli (C, bottom row). Notably, dense 3F HLOs did not express SFTPB (C), but maintained expression of SOX9 (D). Scale bar represents 50 um.

Figure 9E:
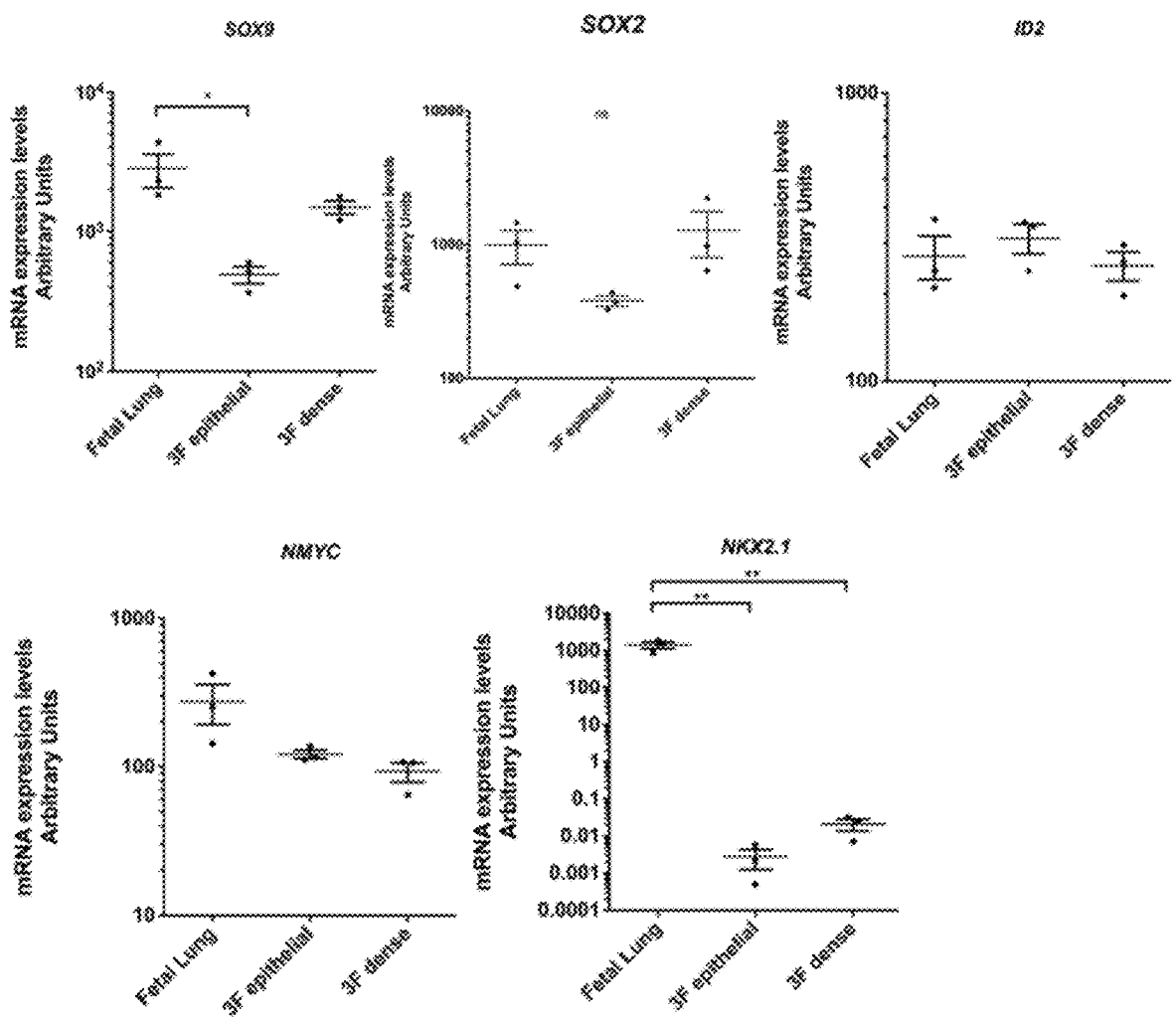
Figure 9F:
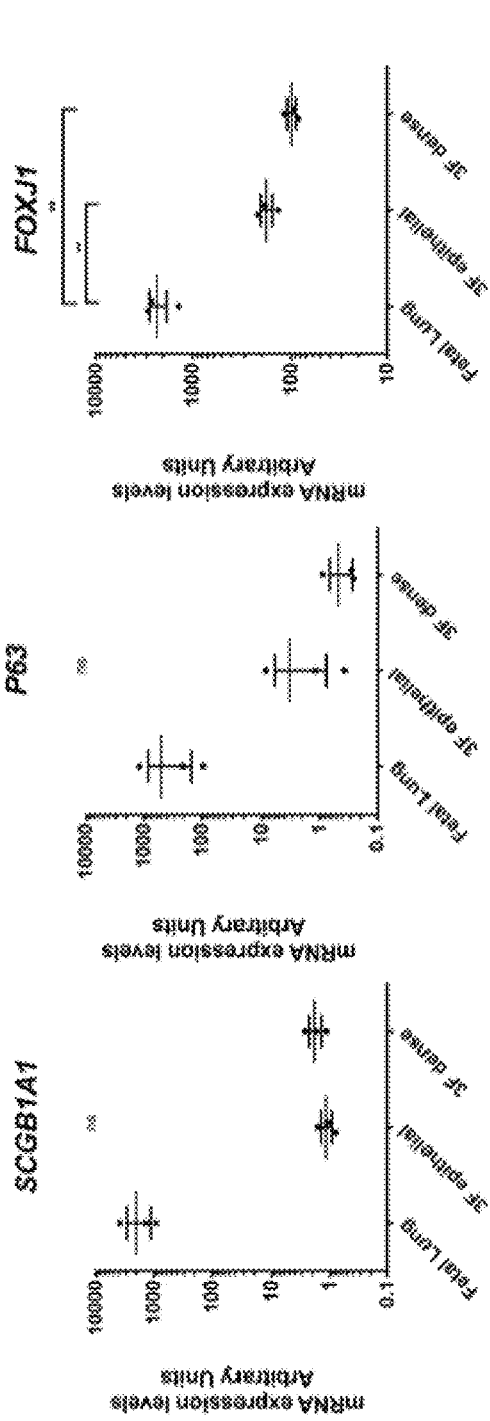
Figure 9G:
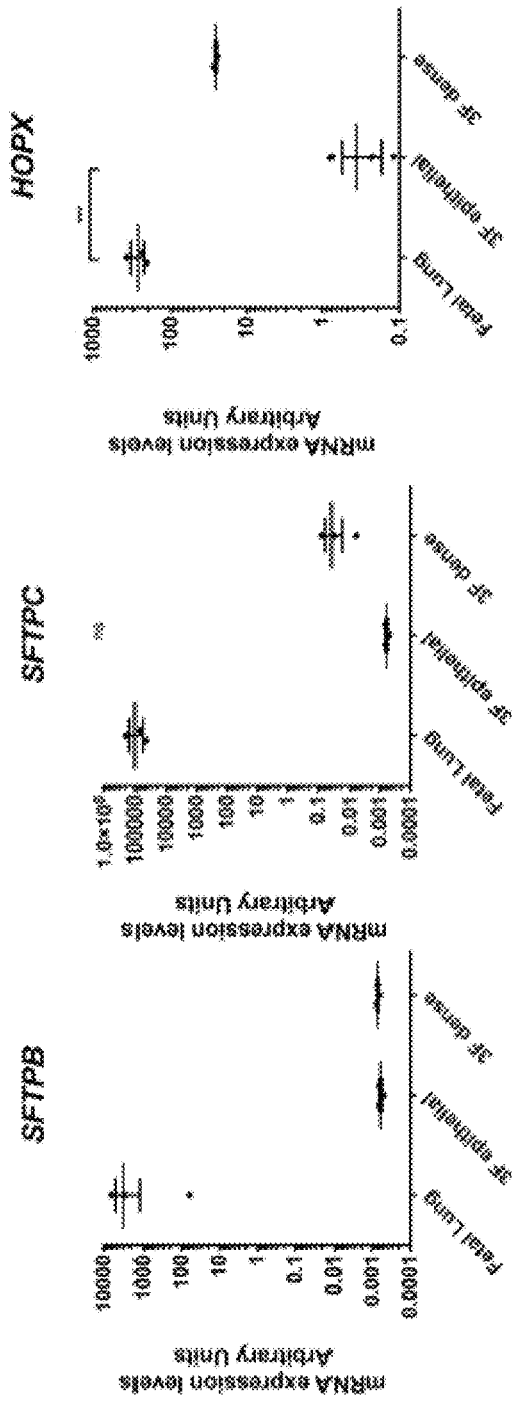

FIG. 9E-G: After 42 days in vitro, dense 3F HLOs were compared to epithelial 3F HLOs and whole fetal lung tissue by QRT-PCR. Consistent with immunostaining data, dense 3F HLOs were enriched for HOPX mRNA compared to epithelial HLOs or human fetal lung tissue (H). In general, both dense and epithelial 3F HLOs had lower expression of differentiated cell markers, and in the general lung epithelial marker, NKX2.1 was reduced compared to the fetal lung, consistent with our previously published lung organoid data (Dye et al., 2015). Each data point represents an independent biological replicate, and the mean+/−the standard error of the mean is shown for each group. An unpaired one-way analysis of variance was performed followed by Tukey's multiple comparison test to compare the mean of each group to the mean of every other group for each target. A significance value of 0.05 was used. P>0.05 ns, P≤0.05*, P≤0.01, P≤0.001*, P≤0.0001****.

Figure 10C:
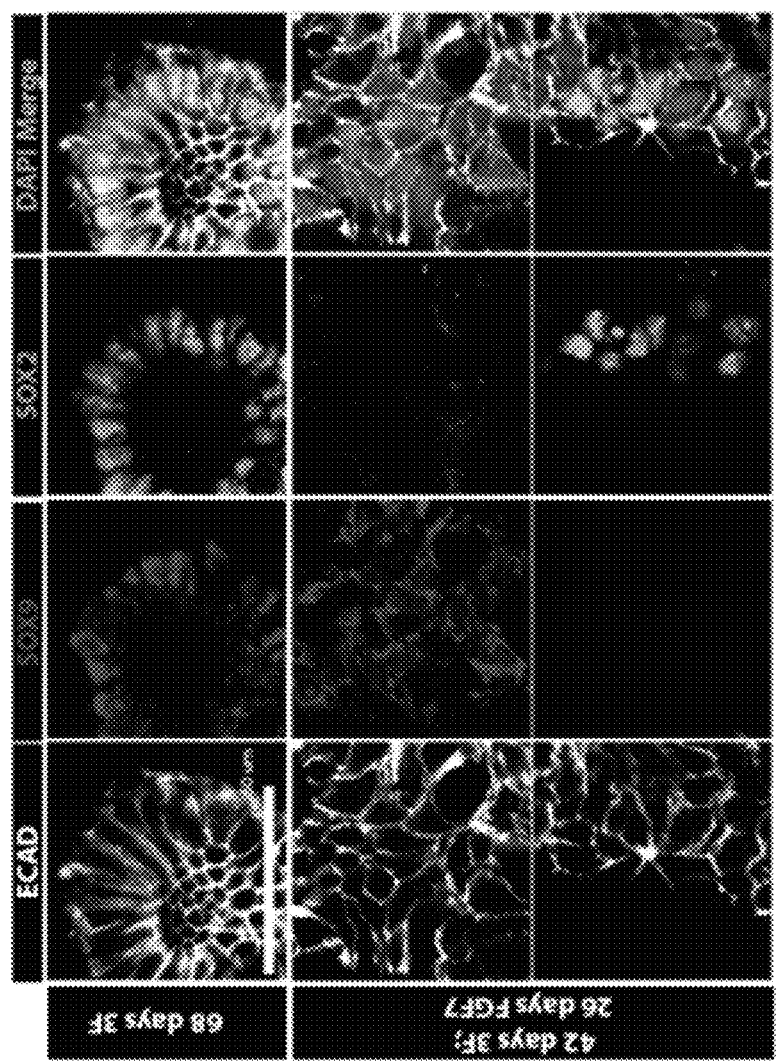
Figure 10A:
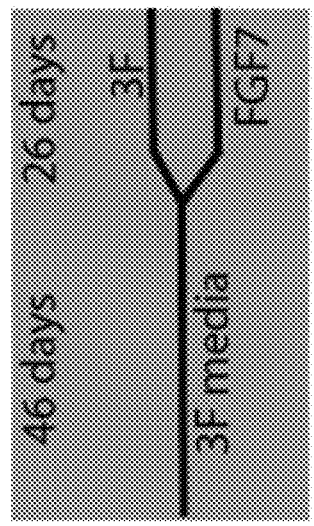

FIG. 10A: 3F Media is required for prolonged maintenance of distal progenitor-like cells in HLOs. Schematic of the experimental setup in FIG. 10. HLOs were generated and grown in 3F media for 42 days, at which time, half of the tissue was maintained in 3F for an additional 26 days while the other half was switched to FGF7-only media.

Figure 10B:
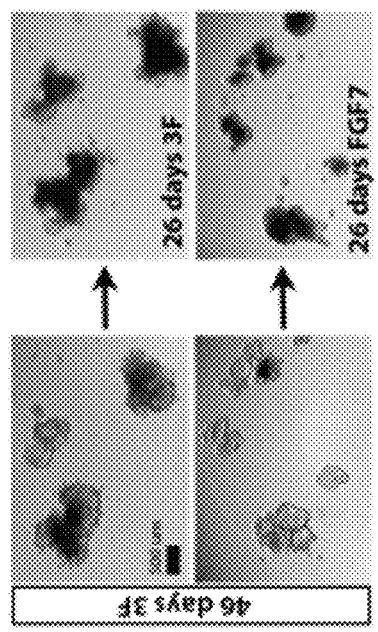

FIG. 10B: Wholemount brightfield imaging revealed that HLOs grown in 3F maintained bud-like structures for the duration of the experiment (top), whereas FGF7-only HLOs lost bud-like structures and the epithelium appeared smooth on the outer surface of the 3D structure (bottom). Scalebar represents 500 um.

FIG. 10C: Peripheral budded regions of 3F HLOs showed nuclear SOX9/SOX2 co-staining (top row), whereas FGF7-only HLOs exhibited a loss of double-positive cells (middle and bottom row). FGF7-only HLOs still expressed SOX2 and SOX9, but we observed that SOX9 expression appeared cytoplasmic (middle row), and was not co-expressed in the same domains as SOX2 (bottom row). Scale bar represents 50 um.

Figure 10D:
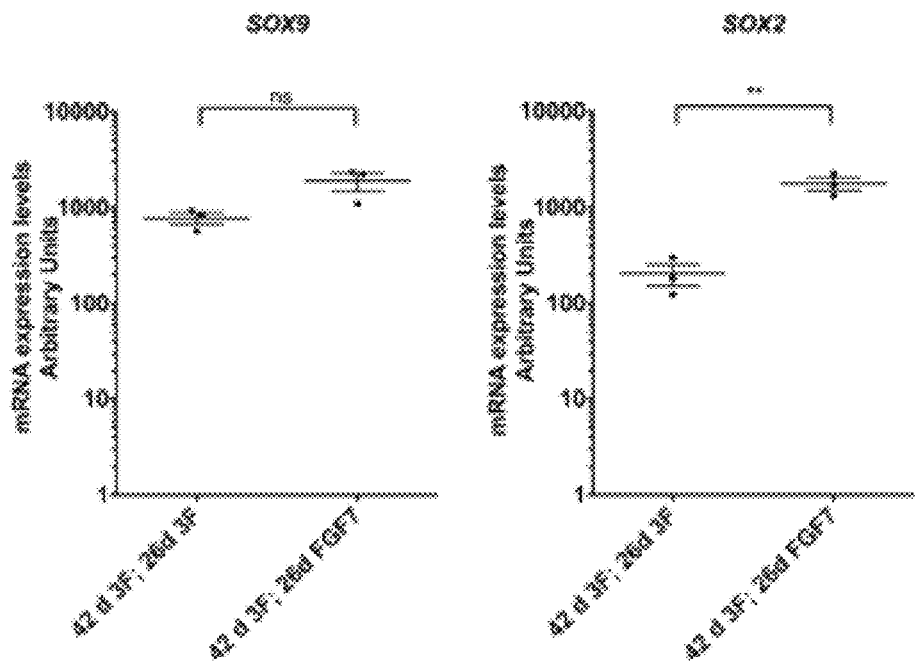

FIG. 10D: QRT-PCR analysis comparing 3F HLOs and FGF7-only HLOs demonstrated that SOX9 expression was not different between groups, whereas SOX2 was increased when grown in FGF7-only. Each data point represents an independent biological replicate.

Figure 10E:
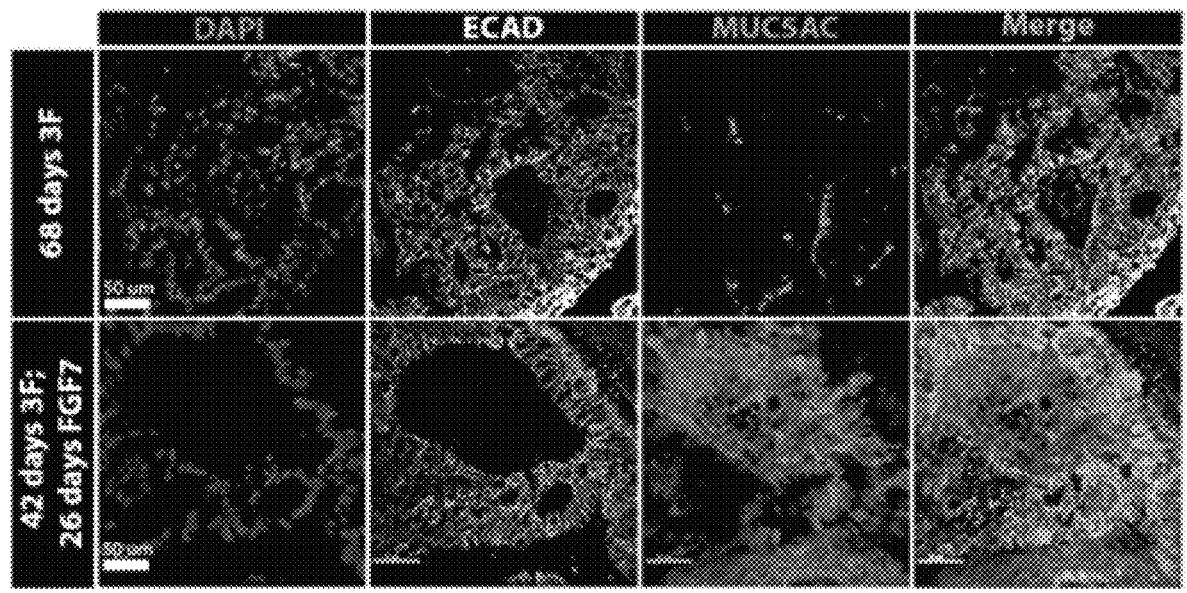

FIG. 10E: 3F HLOs and FGF7-only HLOs were examined for expression of the goblet cell marker, MUCSAC. A striking increase in the number of MUCSAC+ cells was observed in FGF7-only, as well as an increase in mucus staining within the lumens of the HLO. Scale bars represent 50 um.

Figure 10F:
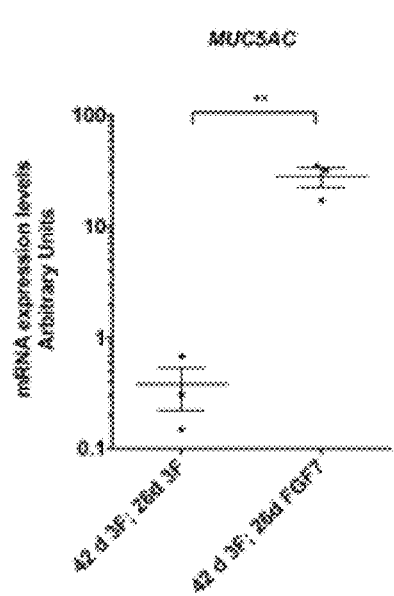

FIG. 10F: MUC5AC gene expression levels reflected protein expression in (E), with FGF7-only HLOs having significantly higher mRNA levels compared to 3F HLOs based on QRT-PCR. Each data point represents an independent biological replicate.

Figure 10G:
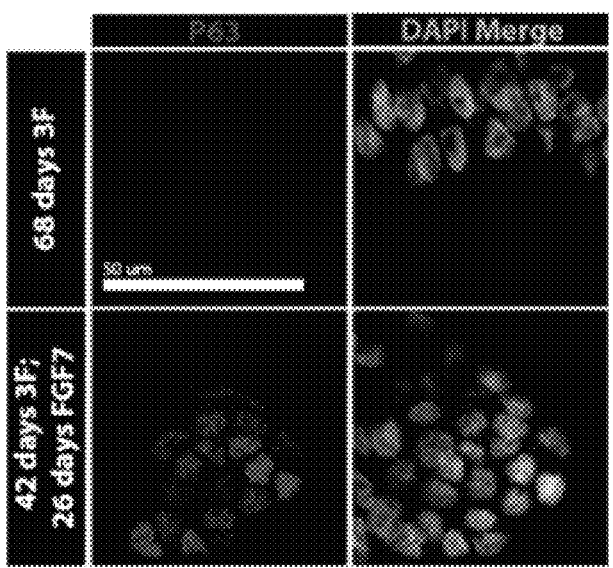
Figure 10H:
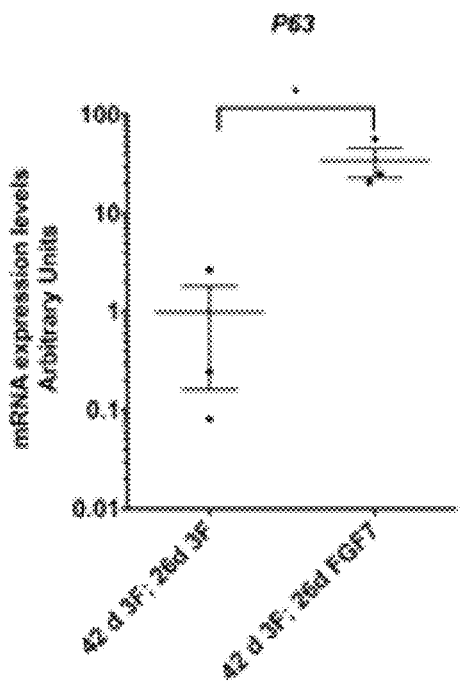

FIG. 10G-H: In 3F HLOs, the basal cell marker, P63, was not observed in immunofluorescent images (G, See also FIG. 7H), and P63 mRNA expression was low based on QRT-PCR (H). In contrast, P63-positive cells were present in FGF7-only HLOs based on immunostaining (G), and P63 mRNA expression was significantly increased based on QRT-PCR (H). Scale bar in (G) represents 50 um. Each data point represents an independent biological replicate.

Figure 10I:
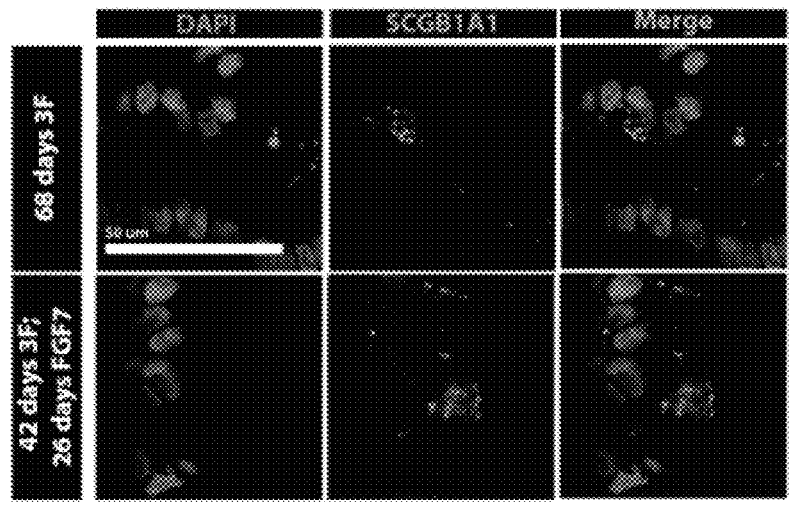
Figure 10J:
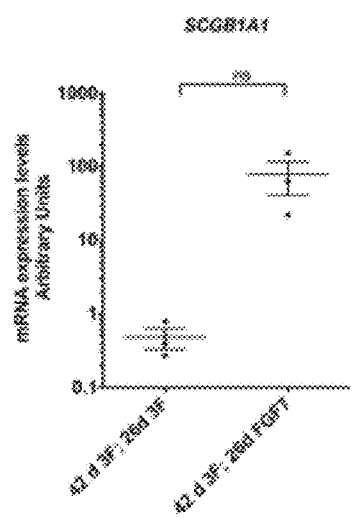
Figure 10K:
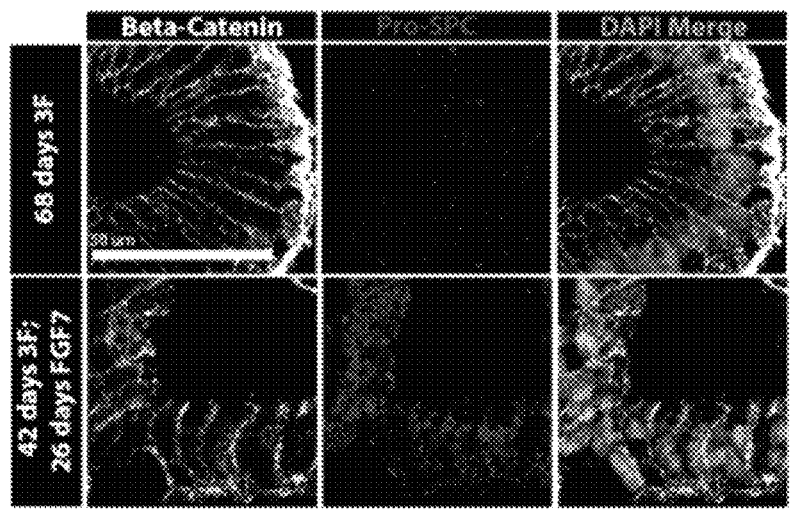
Figure 10L:
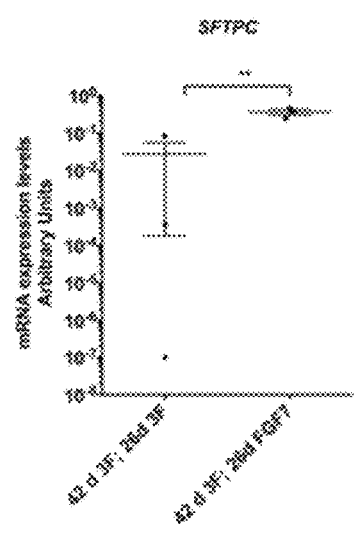
Figure 11A:
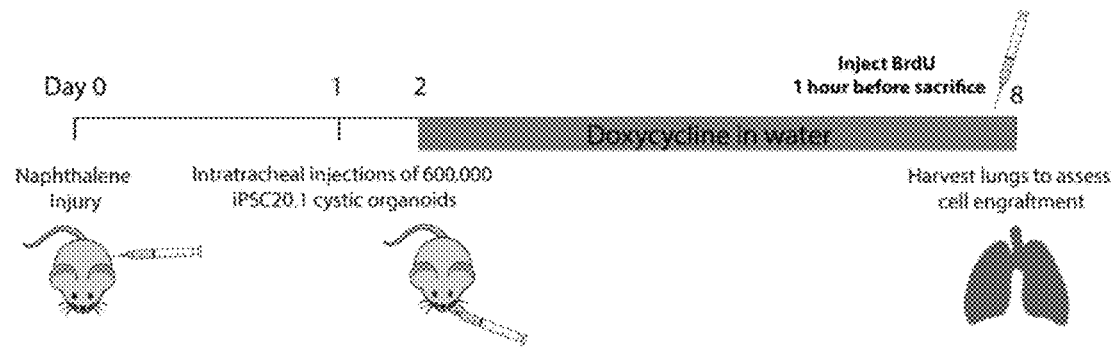
Figure 11B:
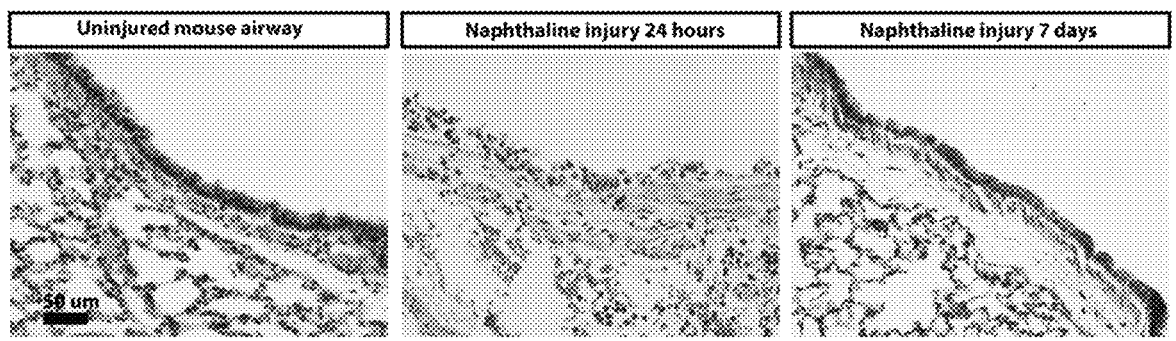
Figure 11C:
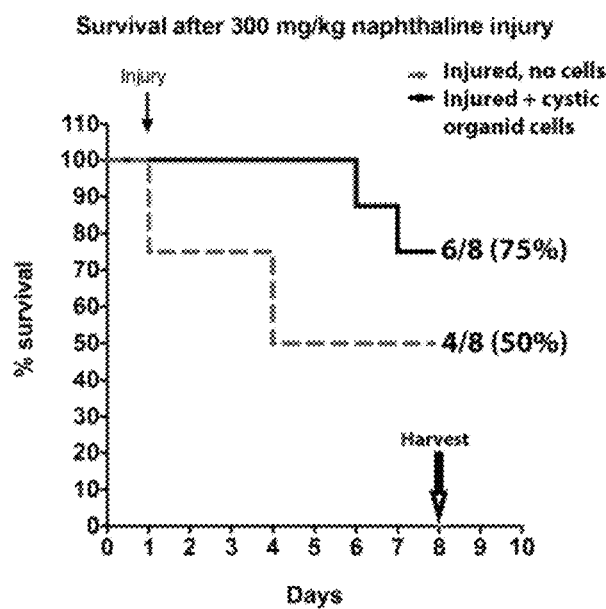
Figure 11G:
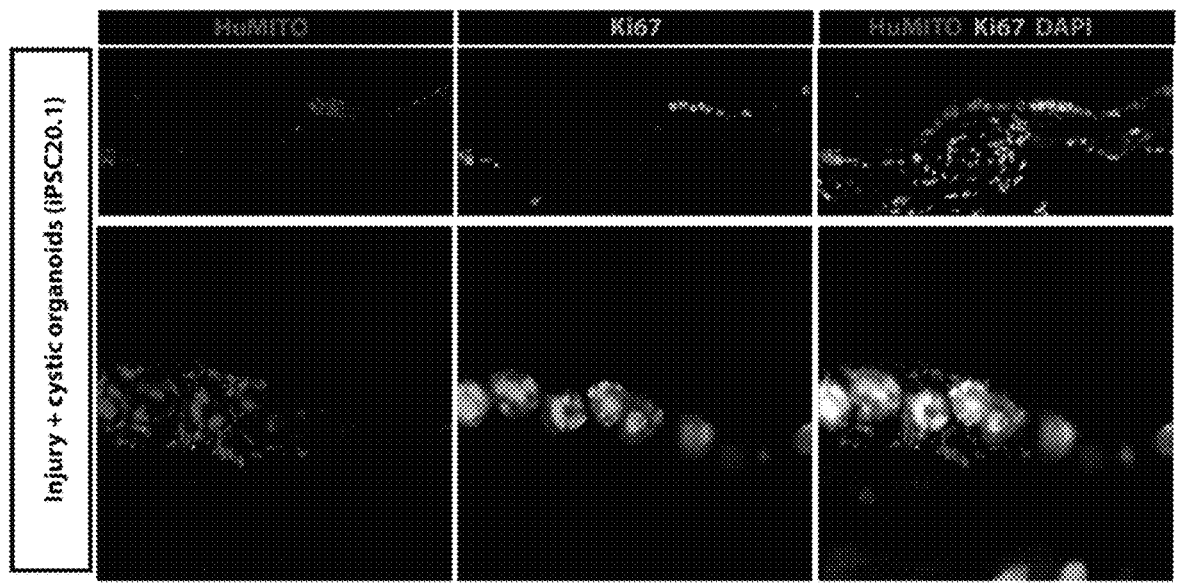
Figure 11H:
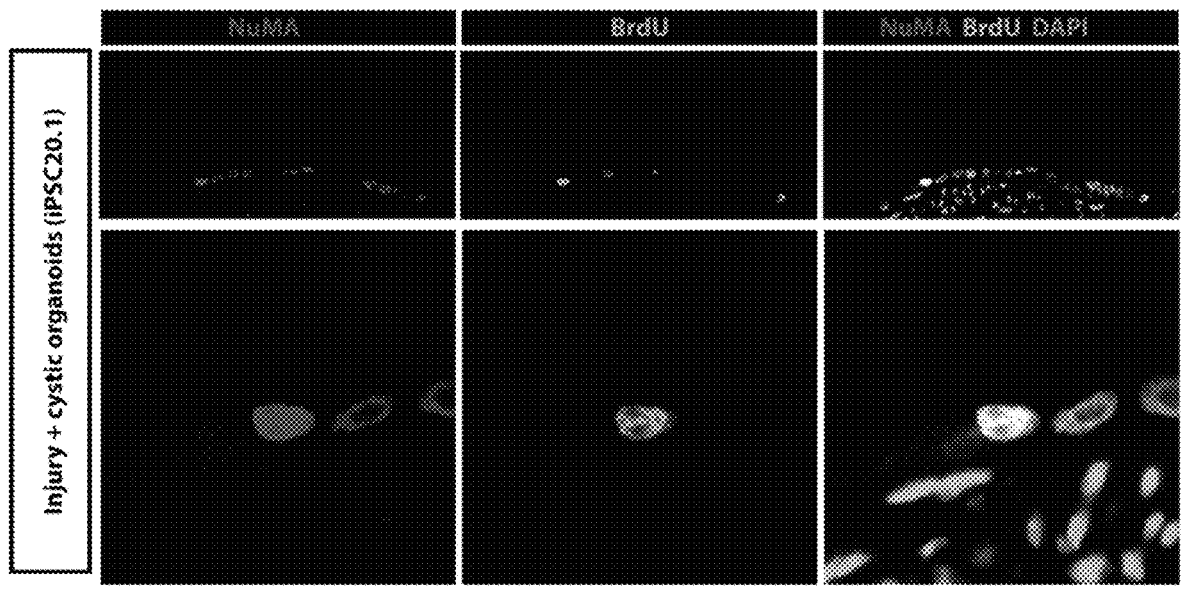
Figure 11I:
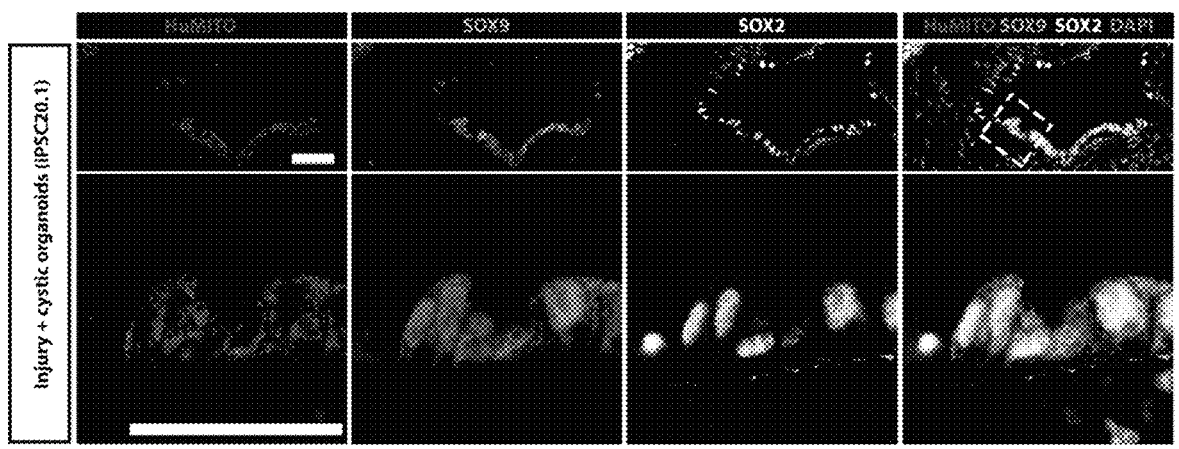
Figure 11J:
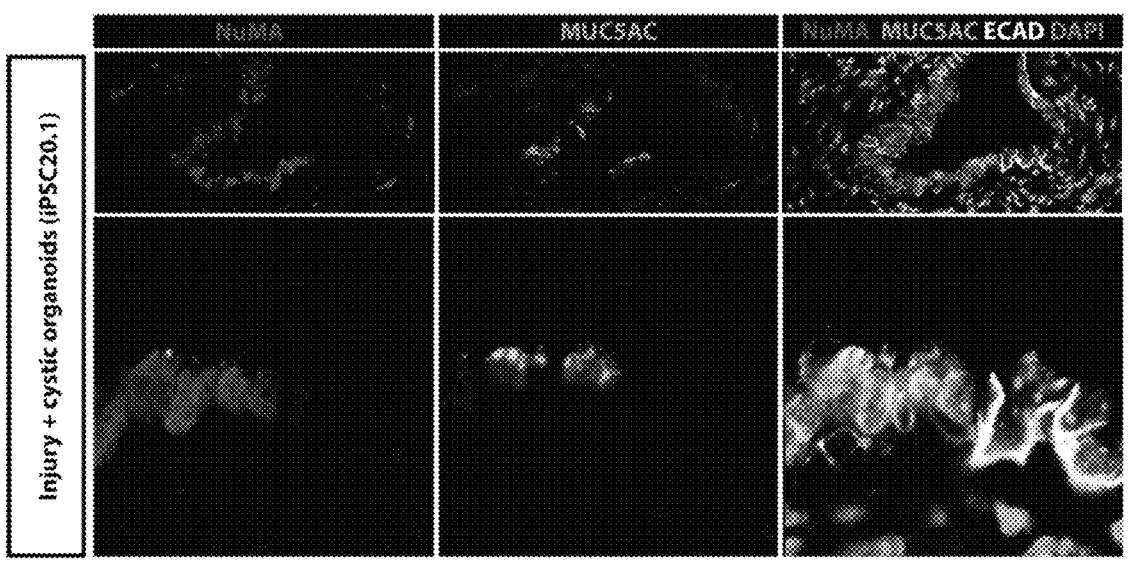
Figure 11K:
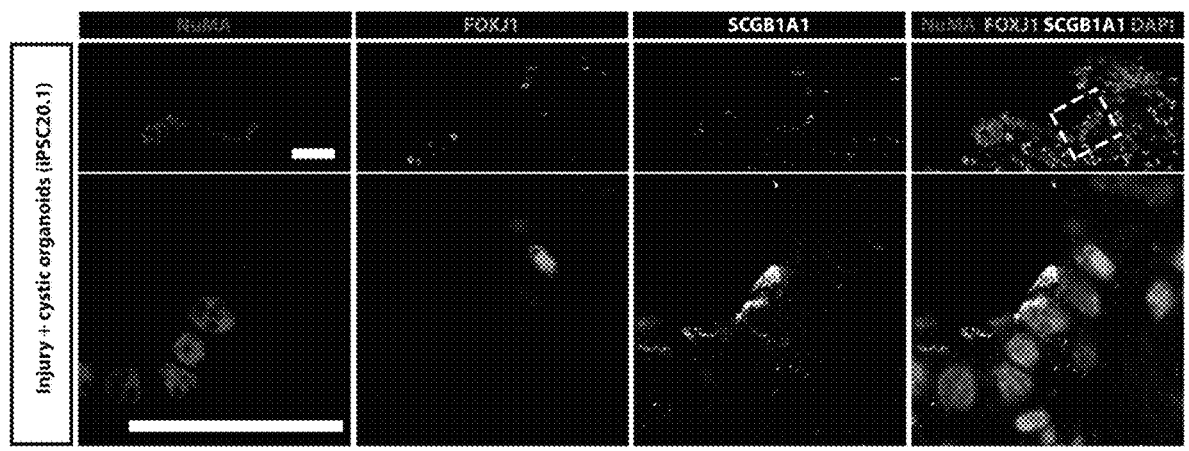
Figure 11L:
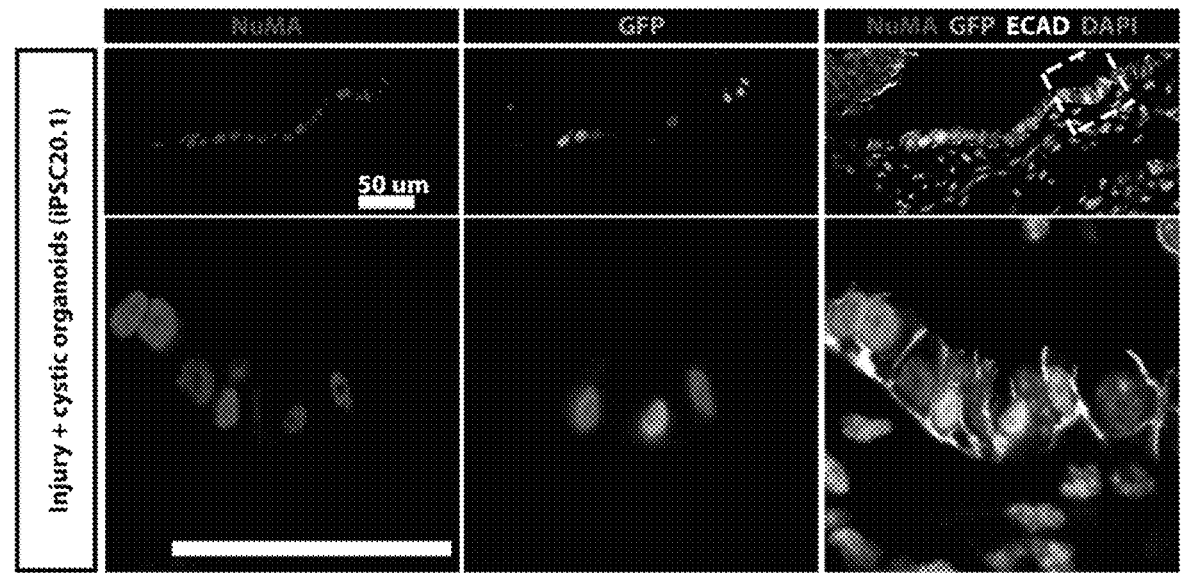

FIG. 10I-J: Immunofluorescence (I) and QRT-PCR (J) were used to examine expression of club cell marker SCGB1A1. Cells positive for SCGB1A1 protein staining were observed in both groups (I). While mRNA levels of SCGB1A1 increased 100-fold in HLOs treated with FGF7-only, this increase was not statistically significant (J). Scale bar in (I) represents 50 um. Each data point represents an independent biological replicate.

FIG. 10K-N: Immunofluorescence (K, M) and QRT-PCR (L, N) were used to examine expression of markers for AECII (SFTPC) (K, L) and AECI (PDPN, HOPX) (M-N). Protein staining (K) and mRNA (L) for SFTPC showed increased expression in FGF7-only HLOs compared to 3F HLOs, although we also note the high variability in expression in the 3F HLOs across biological replicates (L). Similarly, Protein staining for PDPN (M) and HOPX mRNA (N) showed increased expression in FGF7-only HLOs compared to 3F HLOs. Scale bar in (K, M) represents 50 um and applies to all panels in (K) and (M). Each data point in (L) and (N) represents an independent biological replicate.

FIG. 10O: QRT-PCR analysis showed that mRNA levels of FOXJ1 were significantly increased in HLOs treated with FGF7-only (O). However, FOXJ1 protein staining was not detected in either group (data not shown). Each data point represents an independent biological replicate.

(D, F, H, J, L, N, O) The mean+/−the standard error of the mean for each group is shown. For each target, a double-sided student's T-test was used to compare the mean of the 3F group to the mean of the FGF7 alone group. P values less than 0.05 were considered significant. P>0.05 ns, P≤0.05*, P≤0.01, P≤0.001*, P≤0.0001****.

FIG. 11A-L: Cystic human lung organoids generated from human iPSCs engraft into injured mouse airways. A) Schematic of experimental design. 16 immunocompromised NSG male mice were injected with 300 mg/kg of Naphthaline, a chemical that is highly toxic to mouse lung epithelial airway cells, on day 0.24 hours post injury, mice were randomly assigned (8 per group) to receive an intratracheal injection of 600,000 single cells isolated from cystic HLOs maintained in 3F media or no injection of cells. HLOs were generated from the human iPSC 20-1 line, which had been transfected with a tet-o GFP construct and will express GFP when exposed to doxycycline. Doxycycline (1 mg/ml) was added to the drinking water for all mice starting on day 2. 8 days post injury, animals were injected with BrdU to assess cell proliferation and sacrificed one hour later. Lungs were harvested to analyze potential engraftment and cell identity of injected cells. B) H and E staining shows severe disruption of the proximal epithelial layer 24 hours after naphthalene injury. By 7 days post injury the airway epithelium has largely recovered. C) 75% (6/8) of animals that received naphthaline and an injection of HLO cells survived until the day of harvest, compared with 50% (4/8) of animals that did not receive cells. However, increased survival due to cell injections was not statistically significant (log-rank test p>0.05). D) Of the 6 surviving animals which received cells, lungs were sectioned and stained with human specific antibodies (NuMA, huMITO) to assess the degree of cell engraftment. The number of grafts identified on 3 non-serial sections for each lung were analyzed. Engraftment was observed in 4/6 animals. E) The number of human cells in each engrafted cell patch were counted in 3 non-serial sections for each lung. F) Human cells expressing HuMITO (red) from HLOs retained expression of the lung epithelial marker NKX2.1 (green) after engraftment. G) Engrafted human cells (HuMITO, red) were actively proliferating as shown by Ki67 (green). H) Engrafted human cells expressed human NuMA (red), were able to absorb BrdU (green) from the bloodstream of the host and incorporate it into actively proliferating cells. I) Most engrafted human cells (red) retained expression of both SOX2 (white) and SOX9 (green), although SOX9 expression appeared reduced compared to expression levels in the starting material, and the staining pattern appeared to also include cytoplasmic SOX9 staining. J) Engrafted cells (red) expressed MUCSAC (green), a marker of mature Goblet cells. K) Engrafted cells (red) also exhibit positive staining for SCGB1A1, a marker of mature Club cells in the lung. No engrafted cells were found that expressed either FOXJ1 or Acetylated tubulin (data not shown), both markers of mature multiciliated cells. L) A large number of engrafted cells also expressed GFP, suggesting these cells had access to the host blood stream to receive doxycycline from the drinking water. ECAD staining (white) shows the engrafted cells generating a continuous single cell epithelial layer and integrating with host mouse epithelial cells.

DEFINITIONS

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As used herein, the term "organoid" is used to mean a 3-dimensional growth of mammalian cells in culture that retains characteristics of the tissue in vivo, e.g. prolonged tissue expansion with proliferation, multilineage differentiation, recapitulation of cellular and tissue ultrastructure, etc.

DETAILED DESCRIPTION OF THE INVENTION

Experiments conducted during the course of developing embodiments for the present invention aimed to increase the understanding of how multiple growth factor signaling pathways interact to promote maintenance of distal epithelial progenitors in an undifferentiated state. Second, experiments were aimed to elucidate the mechanisms by which distal epithelial progenitor cells of the human fetal lung are maintained and could be expanded and passaged in culture. Third, experiments were aimed to use new information gained from ex vivo culture of mouse and human fetal bud-tip progenitors in a predictive manner, in order to differentiate, de novo, distal epithelial lung progenitor-like cells from hPSCs.

Using isolated epithelial distal-tip progenitor cells from mouse and human fetal lungs during branching morphogenesis, experiments screened growth factors implicated in lung development individually and in combination for their ability to promote tissue expansion and maintenance of progenitor identity in vitro. The results demonstrated that FGF7 promoted robust growth and expansion of both mouse and human epithelial progenitors, but could not maintain the progenitor population, which underwent differentiation. In the mouse, FGF signaling (FGF7+/−FGF10) plus either CHIR-99021 (to stabilize β-catenin) or All-trans Retinoic Acid (RA) increased mRNA and protein expression of the distal epithelial progenitor marker, SOX9, and led to growth/expansion and improved epithelial architecture in vitro. Synergistic activity of all 4 factors (FGF7/FGF10/CHIR-99021/RA; 4-factor; '4F' conditions) led to the highest mRNA expression of Sox9 in mice, whereas in human fetal lung buds we found that only 3-factors '3F' (FGF7, CHIR-99021, RA) were required to maintain growth, allow tissue expansion, and maintain expression of distal epithelial progenitor genes, including SOX9, ID2 and NMYC. Together, these results suggested that FGF, WNT and RA signaling act synergistically to maintain distal progenitor identity in vitro in both mouse and human distal-tip progenitor cells, but that these pathways affected epithelial progenitors in subtly different ways between species. Unexpectedly, such results also revealed that distal epithelial progenitor cells in the human lung express SOX2, which is exclusively expressed in the proximal airway in mice (Hashimoto et al., 2012; Que et al., 2007), identifying an important molecular difference between mouse and human progenitor cells.

When applied to hPSC-derived foregut spheroid cultures, it was observed that 3F conditions promoted robust epithelial growth into larger organoid structures. hPSC-derived organoids grown in 3F media developed a patterned epithelium, with proximal airway-like domains and distal epithelial bud-like domains that possessed SOX9/SOX2+ cells with a molecular profile similar to the human fetal lung buds. Taken together, these studies provide an improved mechanistic understanding of human lung epithelial progenitor cell regulation, and highlight the importance of using developing tissues to provide a framework for improving differentiation of hPSCs into specific lineages.

Accordingly, the invention disclosed herein generally relates to methods and systems for growing, expanding and/or obtaining 3-dimensional lung-like epithelium comprising cells having SOX9 protein activity and SOX2+ protein activity. In particular, the invention disclosed herein relates to methods and systems for growing human cells having SOX9 protein activity and SOX2+ protein activity in vitro, and for promoting pluripotent stem cell derived ventral-anterior foregut spheroid tissue into 3-dimensional lung-like epithelium comprising cells having SOX9 protein activity and SOX2+ protein activity.

In some embodiments, the ventral-anterior foregut spheroid tissue is derived from definitive endoderm cells. In some embodiments, the definitive endoderm cells are derived from pluripotent stem cells. In some embodiments, the pluripotent stem cells are embryonic stem cells and/or induced pluripotent stem cells and/or or cells obtained through somatic cell nuclear transfer.

In some embodiments, an important step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) have a normal XY karyotype, and two cell lines (H7 and H9) have a normal XX karyotype.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Indeed, embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 in GFPhES; and H9 Syn-GFP.

More details on embryonic stem cells can be found in, for example, Thomson et al., 1998, *Science* 282 (5391):1145-1147; Andrews et al., 2005, *Biochem Soc Trans* 33:1526-1530; Martin 1980, *Science* 209 (4458):768-776; Evans and Kaufman, 1981, *Nature* 292(5819): 154-156; Klimanskaya et al., 2005, *Lancet* 365 (9471): 1636-1641).

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

More details on induced pluripotent stem cells can be found in, for example, Kaji et al., 2009, *Nature* 458:771-775; Woltjen et al., 2009, *Nature* 458:766-770; Okita et al., 2008, *Science* 322(5903):949-953; Stadtfeld et al., 2008, *Science* 322(5903):945-949; and Zhou et al., 2009, *Cell Stem Cell* 4(5):381-384.

In some embodiments, examples of iPS cell lines include but not limited to iPS-DF19-9; iPS-DF19-9; iPS-DF4-3; iPS-DF6-9; iPS(Foreskin); iPS(IMR90); and iPS(IMR90).

The lungs of mammals including those of humans, have a soft, spongelike texture and are honeycombed with epithelium, having a much larger surface area in total than the outer surface area of the lung itself.

Breathing is largely driven by the muscular diaphragm at the bottom of the thorax. Contraction of the diaphragm pulls the bottom of the cavity in which the lung is enclosed downward, increasing volume and thus decreasing pressure, causing air to flow into the airways. Air enters through the oral and nasal cavities; it flows through the pharynx, then the larynx and into the trachea, which branches out into the main bronchi and then subsequent divisions. During normal breathing, expiration is passive and no muscles are contracted (the diaphragm relaxes). The rib cage itself is also able to expand and contract to some degree through the use of the intercostal muscles, together with the action of other respiratory and accessory respiratory muscles. As a result, air is transported into or expelled out of the lungs.

In humans, the trachea divides into two main bronchi that enter the roots of the lungs. The bronchi continue to divide within the lung, and after multiple divisions, give rise to bronchioles. The bronchial tree continues branching until it reaches the level of terminal bronchioles, which lead to alveolar sacs. Alveolar sacs, are made up of clusters of alveoli, like individual grapes within a bunch. The individual alveoli are tightly wrapped in blood vessels and it is here that gas exchange actually occurs. Deoxygenated blood from the heart is pumped through the pulmonary artery to the lungs, where oxygen diffuses into blood and is exchanged for carbon dioxide in the haemoglobin of the erythrocytes. The oxygen-rich blood returns to the heart via the pulmonary veins to be pumped back into systemic circulation.

Human lungs are located in two cavities on either side of the heart. Though similar in appearance, the two are not identical. Both are separated into lobes by fissures, with three lobes on the right and two on the left. The lobes are further divided into segments and then into lobules, hexagonal divisions of the lungs that are the smallest subdivision visible to the naked eye. The connective tissue that divides lobules is often blackened in smokers. The medial border of the right lung is nearly vertical, while the left lung contains a cardiac notch. The cardiac notch is a concave impression molded to accommodate the shape of the heart.

Each lobe is surrounded by a pleural cavity, which consists of two pleurae. The parietal pleura lies against the rib cage, and the visceral pleura lies on the surface of the lungs. In between the pleura is pleural fluid. The pleural cavity helps to lubricate the lungs, as well as providing surface tension to keep the lung surface in contact with the rib cage.

Lungs are to a certain extent "overbuilt" and have a tremendous reserve volume as compared to the oxygen exchange requirements when at rest. Such excess capacity is one of the reasons that individuals can smoke for years without having a noticeable decrease in lung function while still or moving slowly; in situations like these only a small portion of the lungs are actually perfused with blood for gas exchange. Destruction of too many alveoli over time leads to the condition emphysema, which is associated with extreme shortness of breath. As oxygen requirements increase due to exercise, a greater volume of the lungs is perfused, allowing the body to match its $CO_2/O_2$ exchange requirements. Additionally, due to the excess capacity, it is possible for humans to live with only one lung, with the one compensating for the other's loss.

The environment of the lung is very moist, which makes it hospitable for bacteria. Many respiratory illnesses are the result of bacterial or viral infection of the lungs. Inflammation of the lungs is known as pneumonia; inflammation of the pleura surrounding the lungs is known as pleurisy.

Vital capacity is the maximum volume of air that a person can exhale after maximum inhalation; it can be measured with a spirometer. In combination with other physiological measurements, the vital capacity can help make a diagnosis of underlying lung disease.

The lung parenchyma is strictly used to refer solely to alveolar tissue with respiratory bronchioles, alveolar ducts and terminal bronchioles. However, it often includes any form of lung tissue, also including bronchioles, bronchi, blood vessels and lung interstitium.

Following gastrulation (embryonic day E7.5 in mice), the definitive endoderm undergoes complex morphogenetic movements that ultimately lead to the formation of the primitive gut tube. The foregut represents the most anterior (cranial) region of this tube, while the midgut and hindgut are located at progressively more posterior regions, towards the caudal end of the embryo (see, e.g., Wells, et al., Annu. Rev. Cell Dev. Biol. 15, 393-410). Transcription factor genes such as Foxa1, Foxa2, Gata4 and Gata6, which are expressed early in the endoderm, are crucial for the survival, differentiation and morphogenesis of the foregut (see, e.g., Kuo, et al., Genes Dev. 11, 1048-1060; Morrisey, et al., Genes Dev. 12, 3579-3590; Ang, et al., Cell 78, 561-574; Wan, et al., J. Biol. Chem. 280, 13809-13816). By E8.0-9.5, the local expression of transcription factors along the antero-posterior (AP) axis of the gut endoderm marks organ-specific domains (or fields). For example, the homeodomain protein gene Nkx2.1 [also known as thyroid transcription factor 1 (Titf1) or T/EBP] is expressed in the thyroid and respiratory fields (see, e.g., Kimura, et al., Genes Dev. 10, 60-69), Hex (hematopoietically expressed homeobox) is expressed in the thyroid and liver fields (see, e.g., Martinez Barbera, et al., Development 127, 2433-2445), and the Pdx1 (pancreas-duodenal-associated homeobox gene) is expressed in the pancreas and duodenal fields (see, e.g., Offield, et al., Development 122, 983-995). In addition, morphogenetic movements foster dynamic interactions between the endoderm and neighboring structures, such as the heart, notochord or the septum transversum (the mesodermal cells that give rise to the diaphragm). Exposure of the endoderm to diffusible signals from these structures at crucial developmental windows is essential for endodermal cell fate specification (see, e.g., Kumar and Melton, Curr. Opin. Genet. Dev. 13, 401-407; Bort, et al., Development 131, 797-80).

Fibroblast growth factor 4 (Fgf4), bone morphogenetic protein 2 (Bmp2) and retinoic acid (RA) are among the signals that confer AP identity to the early endoderm. They render the endoderm competent to respond to signals from the adjacent mesoderm or from nearby structures to initiate morphogenesis (see, e.g., Tiso, eta al., Mech. Dev. 118, 29-37; Stafford and Prince, Curr. Biol. 12, 1215-1220; Wells and Melton, Development 127, 1563-1572). In zebrafish, disrupted retinoic acid (RA) signaling during gastrulation results in the loss of liver and pancreatic (posterior) fates, while thyroid and pharynx (anterior) fates remain unaltered. Conversely, excess RA induces hepatic and pancreatic cell fates at more anterior domains (see, e.g., Stafford and Prince; Curr. Biol. 12, 1215-1220). In mice and rats, RA signaling initiates soon after gastrulation (see, e.g., Rossant, et al., Genes Dev. 5, 1333-1344), but does not seem to be as crucial for foregut AP identity as it is in the zebrafish.

The invention disclosed herein relates to methods and systems for promoting ventral-anterior foregut spheroid tissue into 3-dimensional lung-like epithelium comprising cells having SOX9 protein activity and SOX2+ protein activity.

In some embodiments, PSCs, such as ESCs and iPSCs, undergo directed differentiation in a step-wise manner first into definitive endoderm (DE), then into ventral-anterior foregut spheroid tissue (e.g., SOX2+ anterior foregut 3D spheroid structures), then into 3-dimensional lung-like epithelium comprising cells having SOX9 protein activity and SOX2+ protein activity.

As such, in some embodiments, methods are provided for the directed differentiation of pluripotent cells (e.g., iPSCs or ESCs) into definitive endoderm, and the obtaining of such definitive endoderm. In some embodiments, methods are provided for the directed differentiation of the obtained definitive endoderm into ventral-anterior foregut spheroid tissue, and obtaining of such ventral-anterior foregut spheroid tissue. In some embodiments, methods are provided for the directed differentiation of the obtained ventral-anterior foregut spheroid tissue into 3-dimensional lung-like epithelium comprising cells having SOX9 protein activity and SOX2+ protein activity, and the obtaining of such 3-dimensional lung-like epithelium tissue.

Such methods are not limited to a particular manner of accomplishing the directed differentiation of PSCs into definitive endoderm. Indeed, any method for producing definitive endoderm from pluripotent cells (e.g., iPSCs or ESCs) is applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-β superfamily. In such embodiments, the one or more growth factors comprise the Nodal/Activin and/or the BMP subgroups of the TGF-β superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX2+ marker.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent.

Additional methods for obtaining or creating DE cells that can be used in the present invention include but are not limited to those described in U.S. Pat. No. 7,510,876; U.S. Pat. No. 7,326,572; Kubol et al., 2004, Development 131: 1651-1662; D'Amour et al., 2005, Nature Biotechnology 23:1534-1541; and Ang et al., 1993, Development 119: 1301-1315.

In some embodiments, directed differentiation toward ventral-anterior foregut spheroid tissue, 3-dimensional lung tissue, and lung organoid tissue is achieved by selectively activating or inhibiting certain signaling pathways in the iPSCs and/or DE cells. In some embodiments, the activated and/or inhibited signaling pathways are those active in lung development, including but not limited to the BMP signaling pathway, the TGFβ signaling pathway, the Wnt signaling pathway, the FGF signaling pathway, and the Hedgehog signaling pathway in a step-wise manner.

In some embodiments, directed differentiation of definitive endoderm into 3-dimensional lung-like epithelium tissue is accomplished first through directed differentiation of definitive endoderm into ventral-anterior foregut spheroid tissue, then directed differentiation of the ventral-anterior foregut spheroid tissue into 3-dimensional lung-like epithelium tissue.

Such techniques are not limited to a particular manner of inducing formation of ventral-anterior foregut spheroid tissue from definitive endoderm. In some embodiments, inducing formation of ventral-anterior foregut spheroid tissue from definitive endoderm is accomplished through selectively activating the Wnt signaling pathway and the FGF signaling pathway, and inhibiting the BMP signaling pathway, and the TGFβ signaling pathway in the DE cells. In some embodiments, activating and/or inhibiting one or more signaling pathways within the definitive endoderm cells comprises culturing the definitive endoderm cells with a Wnt signaling pathway agonist, a FGF signaling pathway agonist, a BMP signaling pathway inhibitor, and a TGF signaling pathway inhibitor. In some embodiments, activating and/or inhibiting one or more signaling pathways within the definitive endoderm cells comprises culturing the definitive endoderm cells with CHIR99021, FGF4, Noggin, and SB431542.

Such techniques are not limited to a particular manner of inducing formation of 3-dimensional lung-like epithelium from the ventral-anterior foregut spheroid tissue. In some embodiments, inducing formation of 3-dimensional lung-like epithelium from the ventral-anterior foregut spheroid tissue occurs through activating the FGF signaling pathway, the retinoic acid signaling pathway, and the Wnt signaling pathway within the ventral-anterior foregut spheroid tissue. In some embodiments, the obtained tissue comprising 3-dimensional lung-like epithelium comprises cells having SOX9 protein activity and SOX2+ protein activity.

In some embodiments, selective activation of the Wnt signaling pathway is accomplished with a Wnt agonist ("W").

The Wnt signalling pathway is defined by a series of events that occur when a Wnt protein binds to a cell-surface receptor of a Frizzled receptor family member. This results in the activation of Dishevelled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist (e.g., a small molecule or agonist that activates the Wnt signaling pathway) is defined as an agent that activates TCF/LEF-mediated transcription in a cell. Wnt agonists are therefore selected from true Wnt agonists that bind and activate a Frizzled receptor family member including any and all of the Wnt family proteins, an inhibitor of intracellular β-catenin degradation, and activators of TCF/LEF. Said Wnt agonist is added to the iPSCs and/or DE cells for purposes of directed differentiation of such cells toward lung organoids in an amount effective to stimulate a Wnt activity in a cell by at least 10%, more preferred at least 20%, more preferred at least 30%, more preferred at least 50%, more preferred at least 70%, more preferred at least 90%, more preferred at least 100%, relative to a level of said Wnt activity in the absence of said molecule, as assessed in the same cell type. As is known to a skilled person, a Wnt activity can be determined by measuring the transcriptional activity of Wnt, for example by pTOPFLASH and pFOPFLASH Tcfluciferase reporter constructs (see, e.g., Korinek et al., 1997. Science 275:1784-1787).

A Wnt agonist may comprise a secreted glycoprotein including Wnt-1/Int-1; Wnt-2/Irp (Int-1-related Protein); Wnt-2b/13; Wnt-3/Int-4; Wnt-3a (R&D systems); Wnt-4; Wnt-5a; Wnt-5b; Wnt-6 (Kirikoshi H et al. 2001. Biochem Biophys Res Com 283: 798-805); Wnt-7a (R&D systems); Wnt-7b; Wnt-8a/8d; Wnt-8b; Wnt-9a/14; Wnt-9b/14b/15; Wnt-10a; Wnt-10b/12; Wnt-11; and Wnt-16. An overview of human Wnt proteins is provided in "THE WNT FAMILY OF SECRETED PROTEINS", R&D Systems Catalog, 2004.

Further Wnt agonists include the R-spondin family of secreted proteins, which is implicated in the activation and regulation of Wnt signaling pathway and which is comprised of 4 members (R-spondin 1 (NU206, Nuvelo, San Carlos, Calif.), R-spondin 2 ((R&D systems), R-spondin 3, and R-spondin-4); and Norrin (also called Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al. (2007) BMC Cell Biol. 8: 12).

Compounds that mimic the activity of R-spondin may be used as Wnt agonists of the invention. It has recently been found that R-spondin interacts with Lgr5. Thus, Lgr5 agonists such as agonistic anti-Lgr5 antibodies are examples of Wnt agonists that may be used in the invention.

A small-molecule agonist of the Wnt signaling pathway, an aminopyrimidine derivative, was identified and is also expressly included as a Wnt agonist (Liu et al. (2005) Angew Chem Int Ed Engl. 44, 1987-90).

Known GSK-inhibitors comprise small-interfering RNAs (siRNA; Cell Signaling), lithium (Sigma), kenpaullone (Biomol International; Leost, M. et al. (2000) Eur. J. Biochem. 267, 5983-5994), 6-Bromoindirubin-30-acetoxime (Meijer, L. et al. (2003) Chem. Biol. 10, 1255-1266), SB 216763 and SB 415286 (Sigma-Aldrich), and FRAT-family members and FRAT-derived peptides that prevent interaction of GSK-3 with axin. An overview is provided by Meijer et al., (2004) Trends in Pharmacological Sciences 25, 471-480. Methods and assays for determining a level of GSK-3 inhibition are known to a skilled person and comprise, for example, the methods and assay as described in Liao et al 2004, Endocrinology, 145(6): 2941-9.

In some embodiments the Wnt agonist is a Gsk3 inhibitor. In some embodiments, the Gsk3 inhibitor is selected from the group consisting of CHIR 99021, CHIR 98014, BIO-acetoxime, BIO, LiCl, SB 216763, SB 415286, AR A014418, 1-Azakenpaullone, and Bis-7-indolylmaleimide. In some embodiments the Gsk3 inhibitor is CHIR 99021 or CHIR 98014 at a concentration of at least about 4 μM to about 10 μM i. In some embodiments the Gsk3 inhibitor comprises an RNAi targeted against Gsk3.

In some embodiments, the Wnt agonist added to the iPSCs and/or DE cells for purposes of directed differentiation of such cells toward lung organoids is CHIR 99021. In some embodiments, CHIR 99021 is preferably added to the iPSCs and/or DE cells for purposes of directed differentiation of such cells toward lung organoids at a concentration of at least 200.

In some embodiments, selective activation of the FGF signaling pathway is accomplished with a FGF agonist ("F") (e.g., a small molecule or agonist that activates the FGF signaling pathway).

In some embodiments, the FGF agonist added to the iPSCs and/or DE cells for purposes of directed differentiation of such cells toward lung organoids is able to bind to FGFR2 or FGFR4. An FGF able to bind to FGFR2 (FGF receptor) or FGFR4 is preferably FGF4, FGF7 or FGF10, most preferably FGF10.

FGF10 is a protein that belongs to the fibroblast growth factor (FGF) family of proteins. FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. Most FGFs bind more than one receptor (Ornitz J Biol. Chem. 1998 Feb. 27; 273 (9):5349-57). However, FGF10 and FGF7 are unique among FGFs in that they interact only with a specific isoform of FGFR2, designated FGFR2b which is expressed exclusively by epithelial cells (Igarashi, J Biol. Chem. 1998 273(21):13230-5). FGF10 is a preferred FGF able to bind to FGFR2 or FGFR4.

Preferred concentrations for FGF10 are 20, 50, 100, 500 ng/ml, not higher than 500 ng/ml. FGF (e.g., FGF10) is preferably added to the iPSCs and/or DE cells for purposes of directed differentiation of such cells toward lung organoids when required.

Such methods are not limited to a particular manner of activating the RA signaling pathway. In some embodiments, activating the RA signaling pathway comprises culturing the ventral-anterior foregut spheroid tissue with a small molecule or agonist that activates the RA signaling pathway. In some embodiments, the small molecule or agonist that activates the RA signaling pathway is all-trans retinoic acid. In some embodiments, the small molecule or agonist that activates the RA signaling pathway is AC 261066 (RARβ2 agonist), AC 55649 (selective RARβ2 agonist), adapalene (RARβ and RARγ agonist), AM 580 (retinoic acid analog; RARα agonist), AM 80 (RARα agonist; anticancer), BMS 753 (RARα-selective agonist), BMS 961 (selective RARγ agonist), CD 1530 (potent and selective RARγ agonist), CD 2314 (selective RARβ agonist), CD 437 (RARγ-selective agonist), Ch 55 (potent RAR agonist), isotretinoin (endogenous agonist for retinoic acid receptors), tazarotene (receptor-selective retinoid; binds RARβ and RARγ), and TTNPB (retinoic acid analog; RAR agonist).

In some embodiments, 3-dimensional lung-like epithelium comprises cells having SOX9 protein activity and SOX2+ protein activity produced in vitro from the described methods can be used to screen drugs for lung tissue uptake and mechanisms of transport. For example, this can be done in a high throughput manner to screen for the most readily absorbed drugs, and can augment Phase 1 clinical trials that are done to study drug lung tissue uptake and lung tissue toxicity. This includes pericellular and intracellular transport mechanisms of small molecules, peptides, metabolites, salts.

In some embodiments, 3-dimensional lung-like epithelium comprises cells having SOX9 protein activity and SOX2+ protein activity produced in vitro from the described methods can be used to identify the molecular basis of normal human lung development.

In some embodiments, 3-dimensional lung-like epithelium comprises cells having SOX9 protein activity and SOX2+ protein activity produced in vitro from the described methods can be used to identify the molecular basis of congenital defects affecting human lung development.

In some embodiments, 3-dimensional lung-like epithelium comprises cells having SOX9 protein activity and SOX2+ protein activity produced in vitro from the described methods can be used to correct lung related congenital defects caused by genetic mutations. In particular, mutation affecting human lung development can be corrected using iPSC technology and genetically normal 3-dimensional lung-like epithelium comprises cells having SOX9 protein activity and SOX2+ protein activity produced in vitro from the described methods. In some embodiments, 3-dimensional lung-like epithelium comprises cells having SOX9 protein activity and SOX2+ protein activity produced in vitro from the described methods can be used to generate replacement tissue.

In some embodiments, 3-dimensional lung-like epithelium comprises cells having SOX9 protein activity and SOX2+ protein activity produced in vitro from the described methods can be used to generate replacement lung tissue for lung related disorders.

In some embodiments, a diagnostic kit or package is developed to include 3-dimensional lung-like epithelium comprises cells having SOX9 protein activity and SOX2+ protein activity produced in vitro from the described methods and based on one or more of the aforementioned utilities.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example demonstrates isolation and in vitro culture of murine distal lung bud epithelium.

Figure 1D:
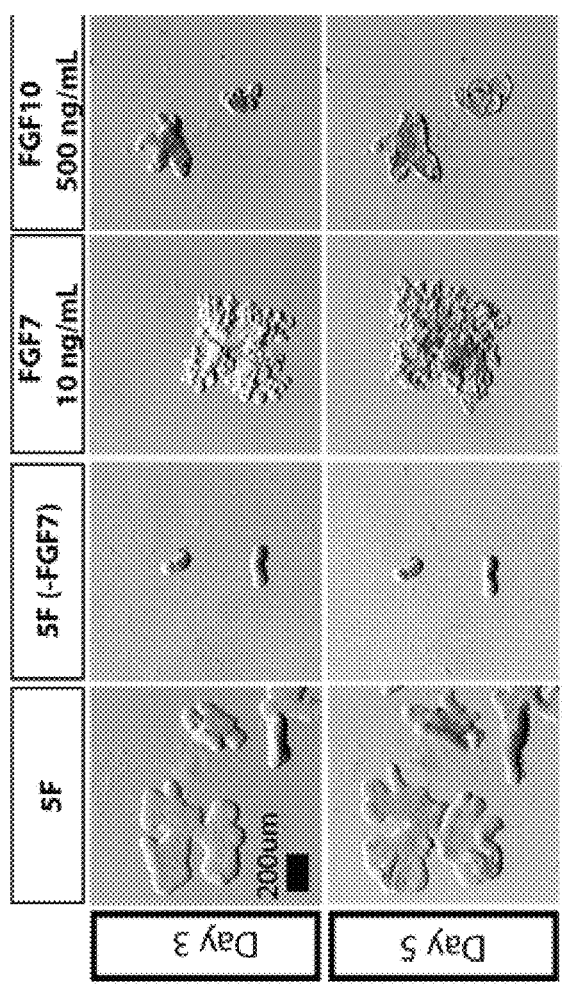
FIG. 1D: All 5 factors ('5F'; FGF7, FGF10, BMP4, RA, CHIR-99021) were combined, or, FGF7 was removed (5F-FGF7) and growth was monitored for 5 days (left two panels). Bud growth was compared for 5 days side-by-side in a low-dose of FGF7 (10 ng/mL) and in a high dose of FGF10 (500 ng/mL) (right two panels). Scale bar represents 200 um.
Figure 2A:
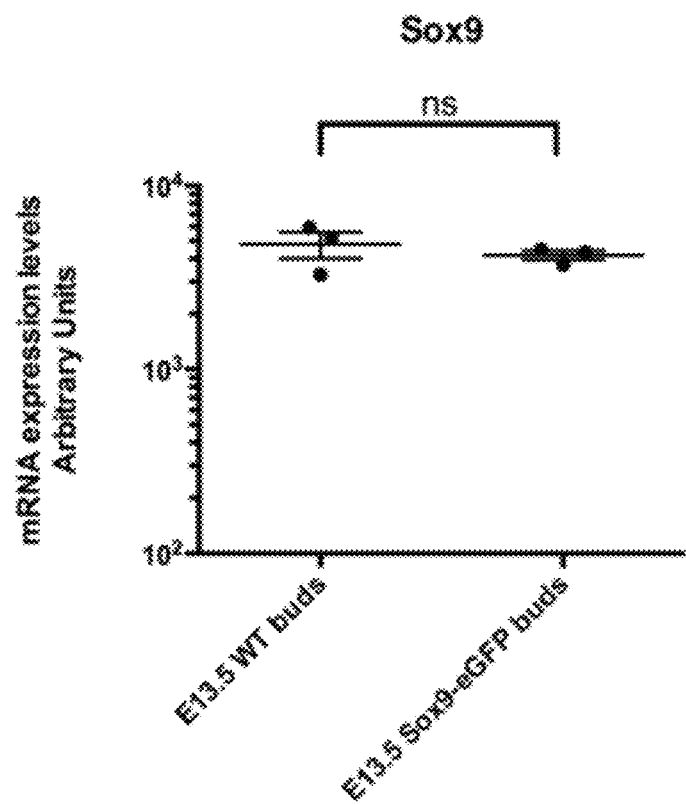
FIG. 2A: FGF7 induces proliferation in a dose-dependent manner in ex vivo cultured murine lung buds. Isolated E13.5 embryonic mouse lung buds from wild type versus Sox9-eGFP mice did not have significantly different levels of Sox9 transcript as shown by qPCR. Each data point represents an independent biological replicate. Error bars plot the standard error of the mean. The mean of each group was compared using a two-sided student's T-test with a significance level of 0.05. $P>0.05$ ns, $P\leq0.05*$, $P\leq0.01$, $P\leq0.001*$, $P\leq0.0001****$.

During branching morphogenesis, the distal epithelial bud tips are comprised of progenitor cells that remain in the progenitor state until the branching program is complete (Chang et al., 2013) and will give rise to all the mature cell types of the lung epithelium (Rawlins et al., 2009). However, the mechanisms maintaining distal progenitors in an undifferentiated state remain unclear. This population of progenitor cells is known to express several transcription factors, including Sox9, Nmyc and Id2 (Chang et al., 2013; Moens et al., 1992; Okubo et al., 2005; Perl et al., 2005; Rawlins et al., 2009; Rockich et al., 2013). In order to study this population of cells, epithelial buds were mechanically isolated from lungs of embryonic day (E) 13.5 Sox9-eGFP mice and cultured in a Matrigel droplet (FIG. 1A). Sox9-eGFP heterozygous lung bud tips were confirmed to have the same level of Sox9 mRNA as their wild type counterparts by QRT-PCR analysis (FIG. 2A). The isolated Sox9+ population was confirmed by GFP expression (FIG. 1B).

Example II

This example demonstrates FGF7 promotes growth and expansion of distal epithelial lung buds.

Experiments were conducted to identify culture conditions that could support the growth and expansion of distal epithelial buds in culture. Signaling events were identified from the literature essential for normal mouse lung epithelial development, including FGF signaling (FGF7 and 10) (Bellusci et al., 1997b; Cardoso et al., 1997; Min et al., 1998; Nyeng et al., 2008; Sekine et al., 1999; Volckaert et al., 2013); Wnt signaling (Elluru and Whitsett, 2004; Goss et al., 2009; Harris-Johnson et al., 2009; Kadzik et al., 2014; Mucenski et al., 2005; 2003; Shu et al., 2005); BMP signaling (Weaver et al., 2000; 1999) and RA signaling (Chen et al., 2010; Desai et al., 2006; 2004; Malpel et al., 2000). Many of these signaling events have previously been used for in vitro differentiation of hPSC-derived lung tissue (Firth et al., 2014; Ghaedi et al., 2013; Gilpin et al., 2014b; Gotoh et al., 2014; Huang et al., 2013; Konishi et al., 2015; Mou et al., 2012; Wong et al., 2012). A low-throughput screen was performed to identify factors that could promote growth of distal bud tips in culture. The screen included FGF7, FGF10, BMP4, All Trans Retinoic Acid (hereafter referred to as 'RA') and CHIR-99021, which inhibits GSK3β and stabilizes β-catenin (βCAT) leading to activation of βCAT-dependent signaling (FIG. 1C). Treating buds with no growth factors (basal media, control) or individual growth factors showed that FGF7 promoted growth, expansion a survival of isolated buds for up to two weeks (FIG. 1C). An experiment was also conducted in which all 5 factors (5F) were combined together, with one factor removed at a time (FIG. 1D). Buds grew robustly in 5F media, whereas removing FGF7 from the 5F media (5F-

FGF7) led to a loss of growth, even after 5 days in culture (FIG. 1D). It was interesting to note that the same concentration of FGF7 and FGF10 did not have the same effect on lung bud outgrowth, since both ligands act on the FGF Receptor 2 (IIIb) isoform (FGFR2IIIb) (Ornitz et al., 1996; X. Zhang et al., 2006), and both ligands are present in the lung during branching morphogenesis (Bellusci et al., 1997b; Tichelaar et al., 2000; White et al., 2006). Previous studies have offered evidence showing that FGF10 has structural similarities with FGF7, but is differentially regulated by components of the extracellular matrix, which may influence the ease of diffusion of the ligand (Makarenkova et al., 2009). To test the possibility that diffusion of ligand through the matrix may explain experimental differences, we treated buds with a 50-fold excess of FGF10 (500 ng/mL compared to 10 ng/mL). A high concentration of FGF10 led to modest growth of buds and was sufficient to keep buds alive in culture for up to 5 days, but cultures did not exhibit the same level of growth as those treated with low levels of FGF7 (FIG. 1D).

Figure 1E:
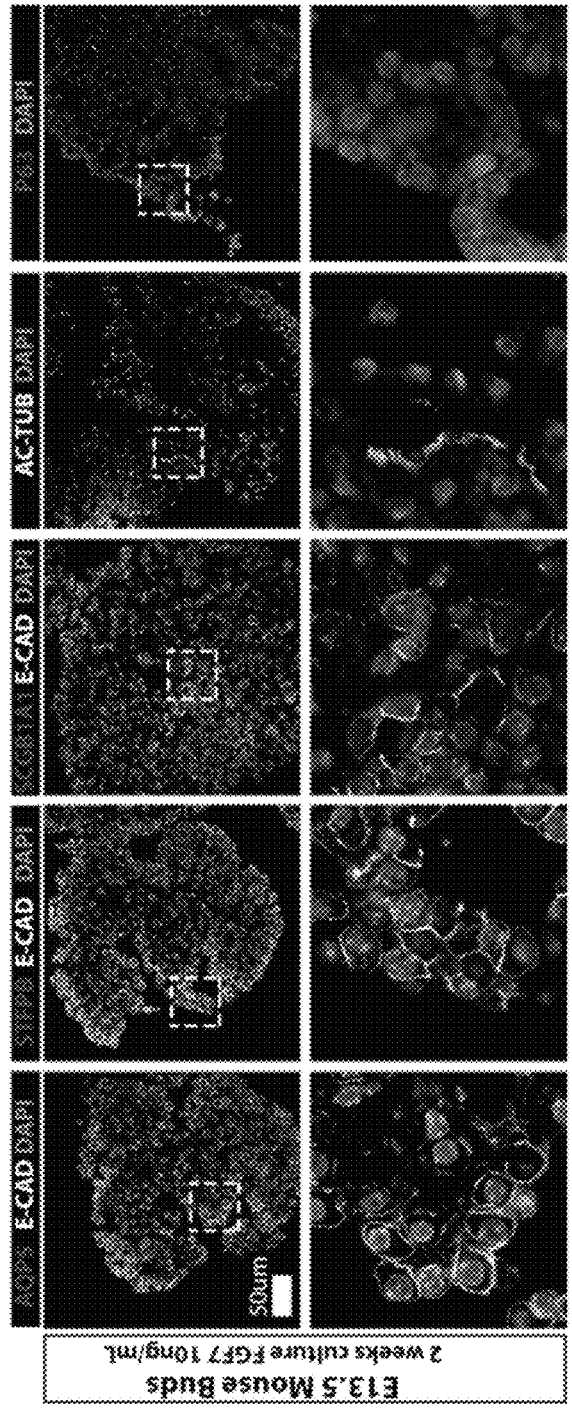
FIG. 1E-F: FGF7 cultured tissue was interrogated for differentiation after 2 weeks in vitro (E) and was compared to the developing mouse lung in vivo (F). Low magnification images (top row in E, F) or at high magnification (bottom row in E, F). Differentiation markers examined include AQP5 (AECI), SFTPB (AECII), SCGB1A1 (club cell), Acetylated-TUBULIN (Ac-Tub; multiciliated cells), P63 (Basal cells). Scale bars in the top and bottom rows represent 50 um.
Figure 1F:
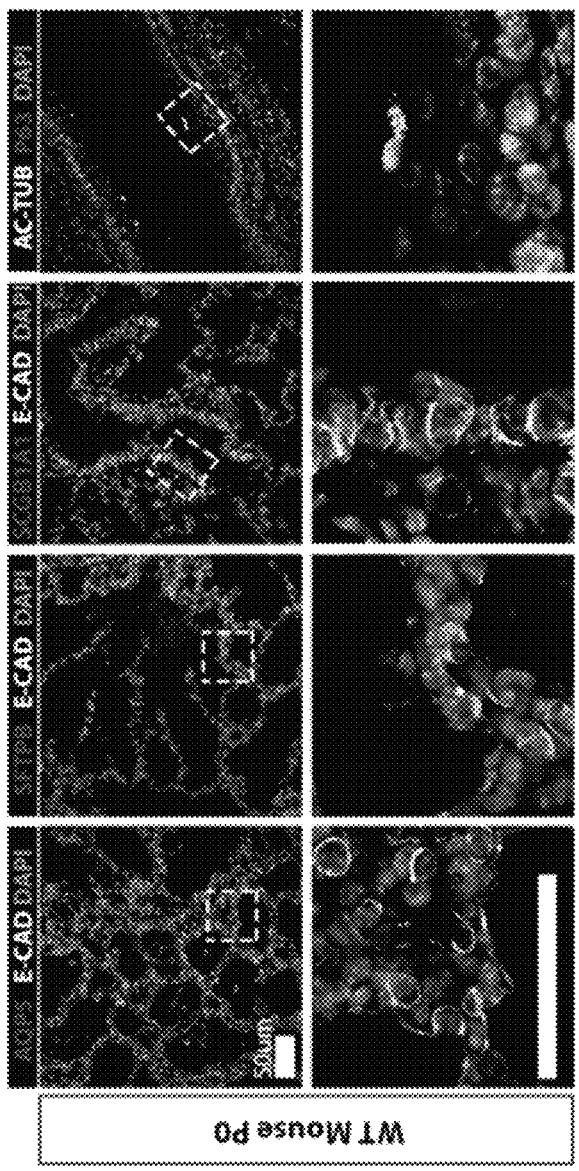
Figure 1G:
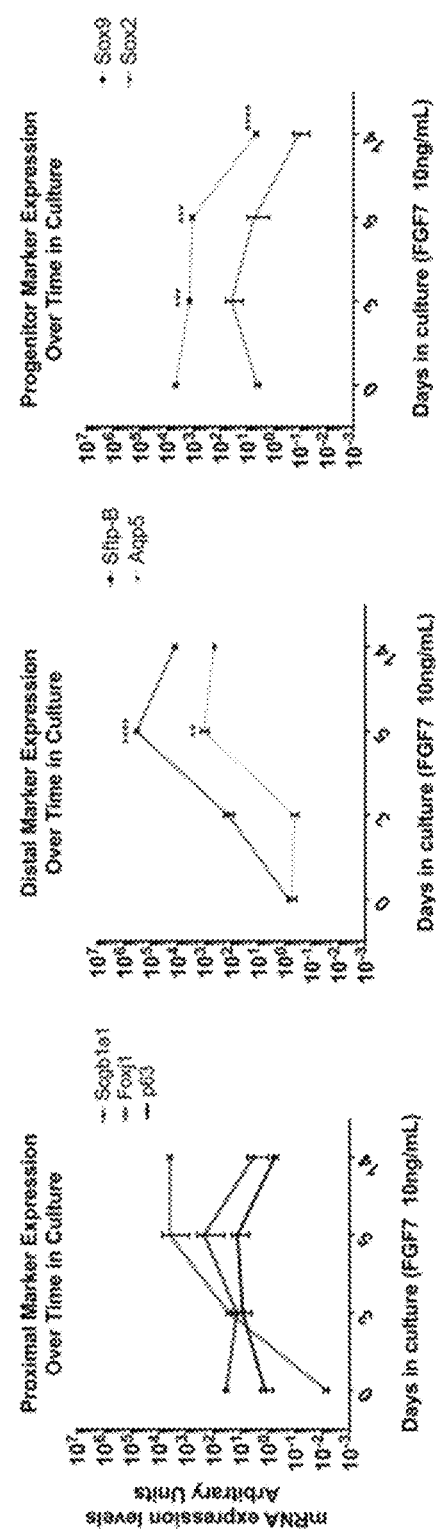
FIG. 1G: QRT-PCR across time in culture with FGF7 indicated that the tissue began to increase expression levels of differentiated cell markers Scgb1a1, Sftpb and Aqp5, and showed a decrease in the expression of the progenitor marker, Sox9. Each data point represents the mean (+/−SEM) of 3 independent biological replicates (n=3). Statistical significance was determined by a one-way, unpaired Analysis of Variance (ANOVA) for each individual gene over time. The mean of each time point was compared to the mean of the expression level for that gene at day 0 of culture. $P>0.05$ ns, $P\leq0.05*$, $P\leq0.01$, $P\leq0.001*$, $P\leq0.0001****$.
Figure 2B:
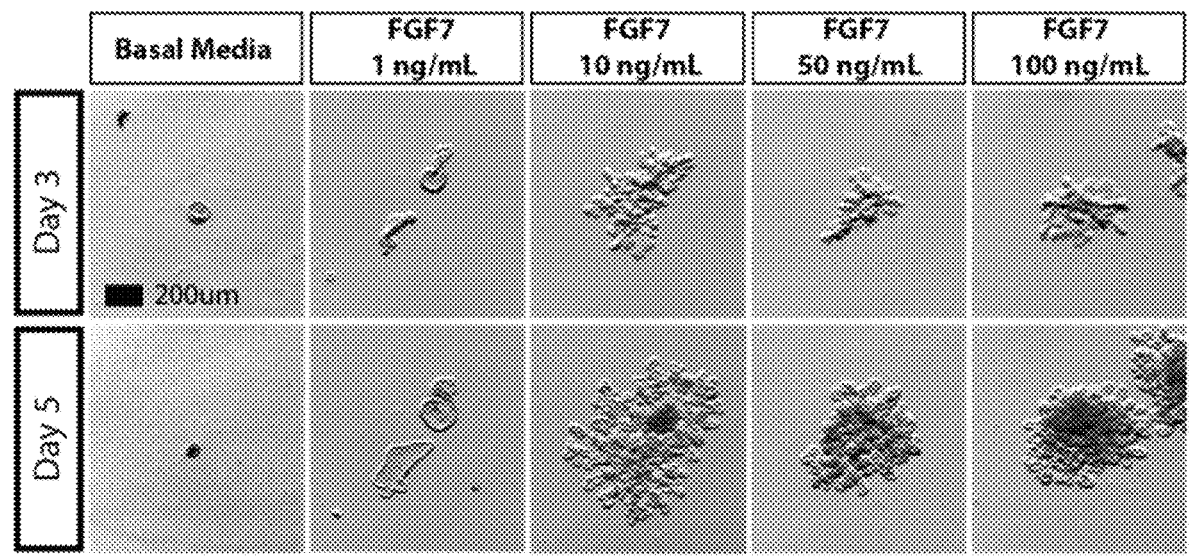
FIG. 2B: Lung buds were grown in increasing concentrations of FGF7 and examined after 3 days and 5 days in vitro. 0 ng/mL (basal media) did not induce bud growth, whereas 1 ng/mL induced very modest growth, and all other conditions supported robust growth for 5 days in vitro. Scale bar represents 200 um.
Figure 2C:
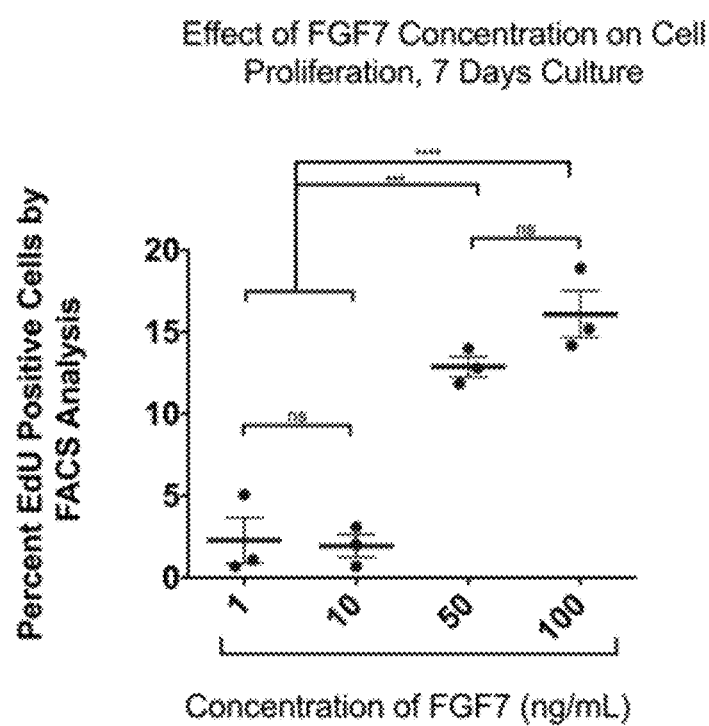
FIG. 2C: Cultured buds were pulse labeled for 1 hour with EdU and the percent of total cell labeled was quantified by Flow Cyotometry. Low doses of FGF7 (1-10 ng/mL) had a similar proportion of cells labeled whereas treatment with 50-100 ng/mL resulted in a significant increase in labeled cells. Each data point represents an independent biological replicate. An unpaired one-way analysis of variance was performed followed by Tukey's multiple comparison test to compare the mean of each group to the mean of every other group within the experiment. A significance value of 0.05 was used. $P>0.05$ ns, $P\leq0.05*$, $P\leq0.01$, $P\leq0.001*$, $P\leq0.0001****$.

Initial experimental conditions used FGF7 concentrations based on previous literature (long/mL; FIG. 1) (Huang et al., 2013). Experiments next tested if FGF7 affected growth in a concentration dependent manner by treating isolated buds with increasing concentrations of FGF7 and performing an EdU incorporation assay (FIGS. 2B and 2C). After one week in culture, cultures were pulsed with EdU for 1 hour prior to Fluorescence Activated Cell Sorting (FACS). Results showed that treating cultures with 50-100 ng/mL of FGF7 increased proliferation significantly above cultures that only received 1-10 ng/mL of FGF7 (FIG. 2C). Despite this increase in proliferation, cultures at lower doses of FGF7 appeared qualitatively healthy (FIG. 2B). Additionally, expansion of buds in 10 ng/mL FGF7 was more robust than 1 ng/mL, and cultures appeared less compact and dense compared to higher doses (FIG. 2B). Based on these results, FGF7 was used at a concentration of 10 ng/mL for the remainder of the experiments.

Example III

This example demonstrates FGF7 promotes growth of Sox9+progenitors followed by cellular differentiation over time in culture.

Figure 2D:
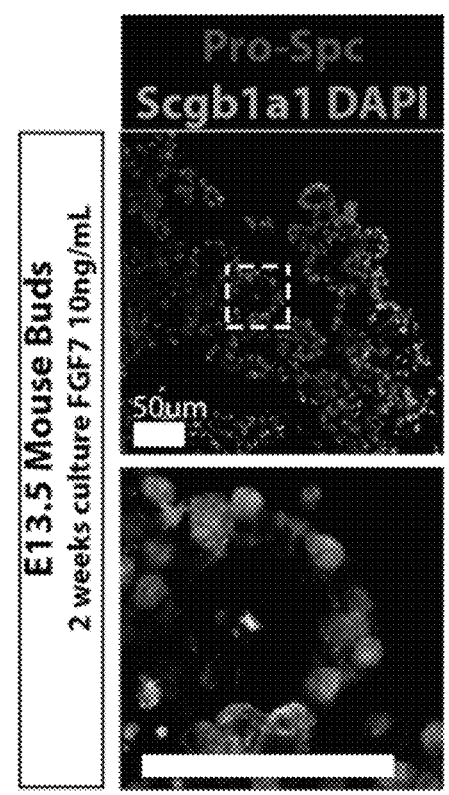
FIG. 2D: Lung bud explants grown in FGF7 for two weeks did not contain cells that were double positive for SCGB1A1 and SFTPC indicating that the explants did not possess bronchoalveolar stem cells (C. F. B. Kim et al., 2005). Scale bar represents 50 um.
Figure 2E:
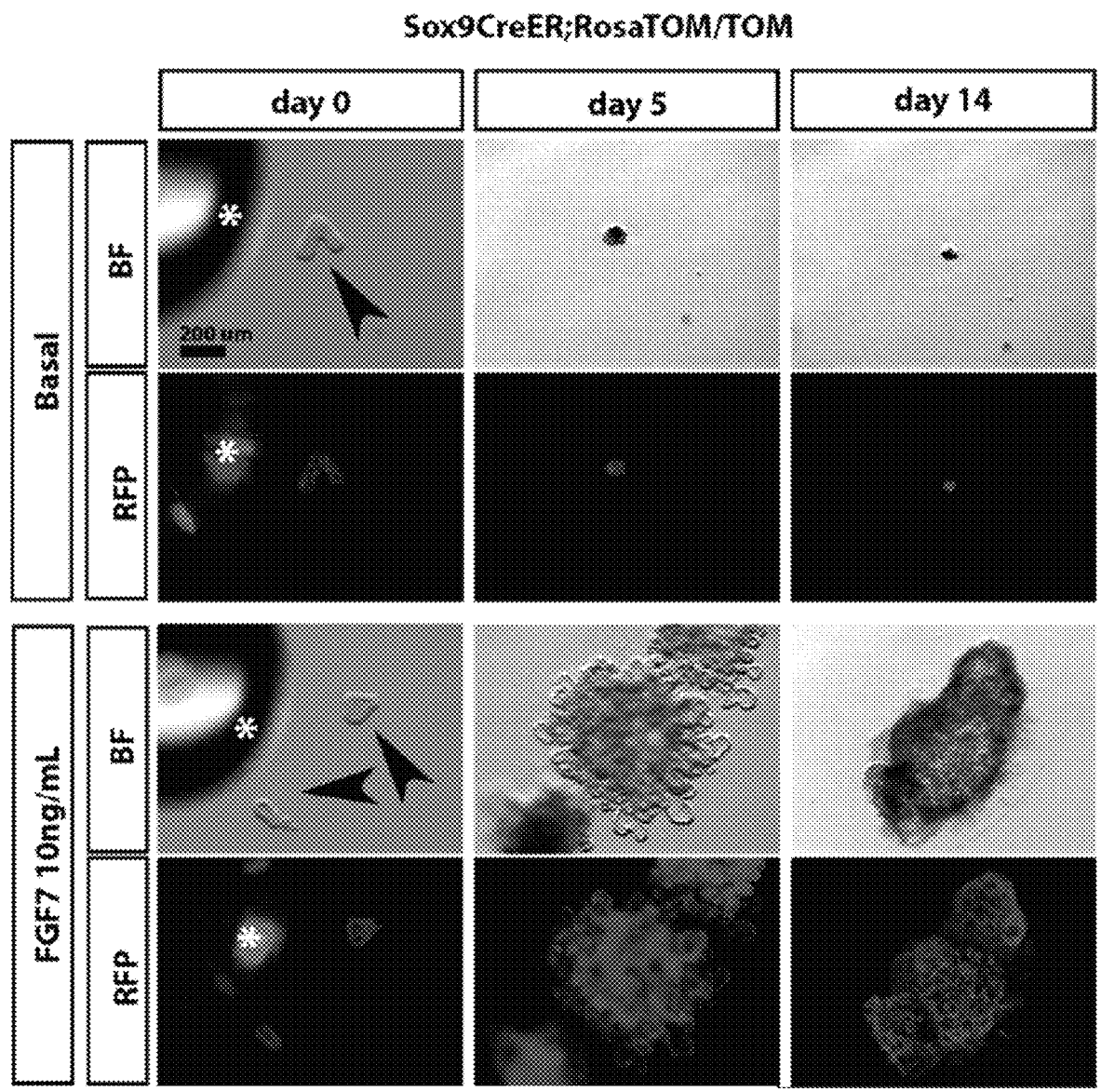
FIG. 2E: Sox9-Cre$^{ER}$; Rosa26$^{Tomato}$ lungs were induced with Tamoxifen 24 hours prior to isolation of the buds, which were isolated and cultured at E13.5. Lineage labeled buds demonstrated that labeled cells expanded in culture over the course of two weeks. Asterisks (*) mark air bubbles within Matrigel droplets that were auto-fluorescent, and arrowheads point to day 0 isolated lung buds. Scale bar represents 200 um.

In order to determine if FGF7 was promoting expansion of Sox9+ distal progenitors cells, experiments performed a lineage trace utilizing Sox9-Cre$^{ER}$; Rosa26$^{Tomato}$ mice. Tamoxifen was given to timed pregnant dams at E12.5, and epithelial lung buds were isolated 24 hours later, at E13.5 (FIG. 2E). Isolated distal buds that were lineage labeled were placed in vitro in basal media (control) or with FGF7. Experiments observed that the Sox9-Cre$^{ER}$; Rosa26$^{Tomato}$ lineage labeled population expanded over time (FIG. 2F). After two weeks in culture, FGF7-treated bud cultures were dense and contained cell that stained positive for mature markers of both alveolar cell types (AEC1-AQP5; AEC2-SFTPB) and bronchiolar cell types (Clara cells—SCGB1A1; multi-ciliated cells-Acetylated Tubulin; basal stem cells—P63) although cells in culture were scattered throughout the tissue and appeared to lack spatial organization (FIG. 1E). None of the cells observed after two weeks in culture were positive for both SFTPC and SCGB1A1, an expression pattern that has been shown to mark bronchio-alveolar stem cells (FIG. 2D)(Lee et al., 2014). Many of these cell types in culture had similar morphologies as cells found at postnatal day 0 of the in vivo mouse lung (FIG. 1F). Experiments next examined the changes of differentiation marker expression over time using QRT-PCR and observed that the length of time in culture led to significant increases in mature alveolar markers Aqp5 and Sftpb, as well as an upward trend in the expression of the club cell marker Scgb1a1. However, time in culture had a less dramatic effect on expression of proximal cell markers Foxj1, p63, and Sox2. The expression of the distal progenitor marker Sox9 was significantly reduced after 3 days in culture and continued to go down as the time in culture increased (FIG. 1H). Collectively, this data strongly indicates that FGF7 promoted an initial expansion of Sox9+ distal epithelial progenitor cells that subsequently underwent differentiation with longer times in culture.

Example IV

This example demonstrates that FGF7, CHIR-99021 and RA act synergistically to maintain the distal progenitor identity in mouse lung buds in vitro.

Figure 3A:
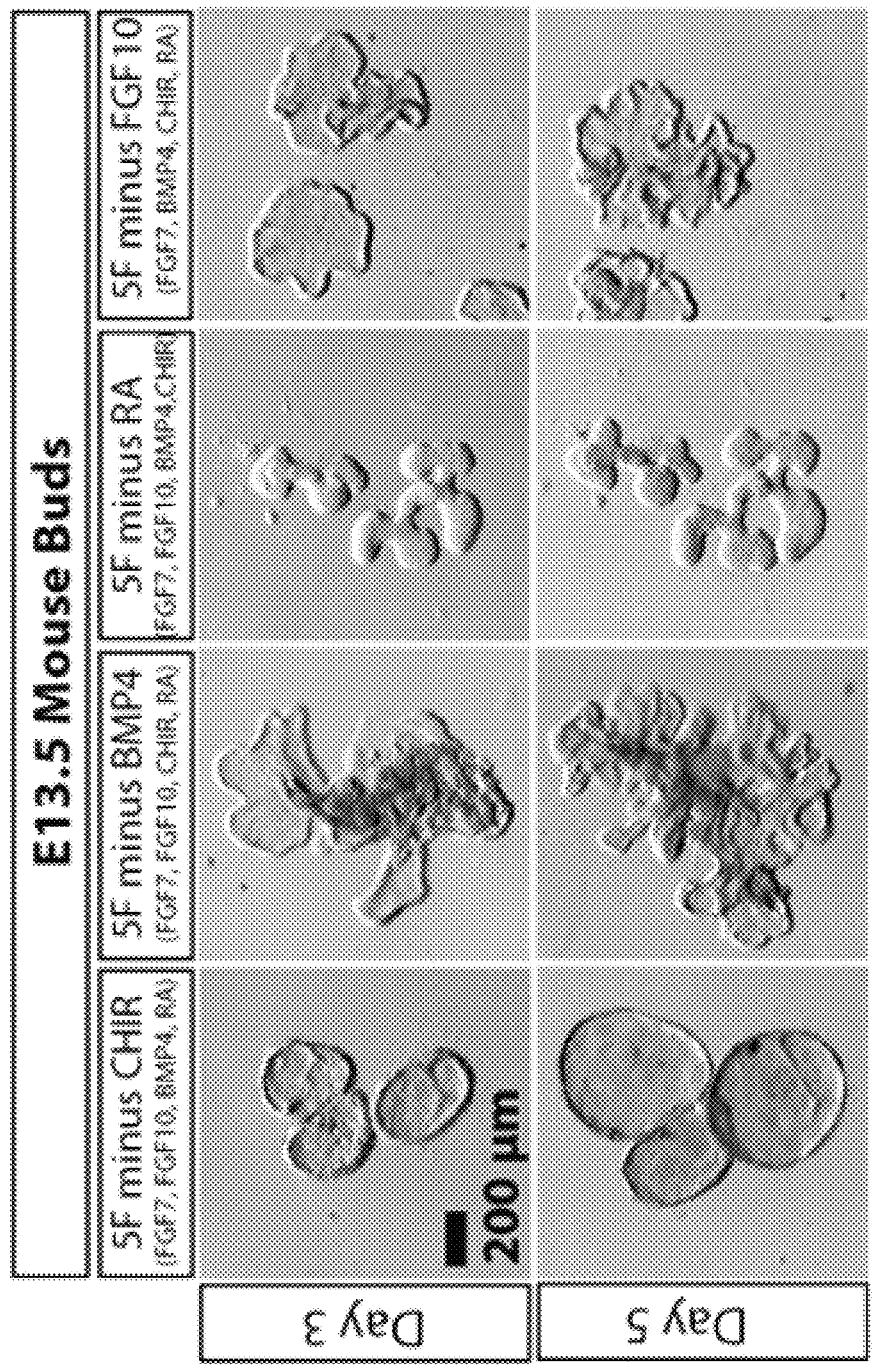
FIG. 3A-B: Synergistic activity of FGF7, CHIR-99021 and RA maintain tip-progenitor-like cells in mouse lung bud explants. Buds were explanted and grown with 5F media minus one growth factor to identify conditions that allowed buds to expand (A) and maximized of expression of Sox9 mRNA (B). Removing BMP4 from the 5F media (5F-BMP4) led to a significant increase in Sox9 expression after 5 days when compared to the full 5F media and resulted in expression levels closest to those of freshly isolated E13.5 lung buds. All groups exhibited low levels of Sox2 expression. Scale bar represents 200 um. Each data point in (B) represents an independent biological replicate plotted with the mean+/−the standard error of the mean. Statistically significant variation in (B) and (D) was determined by an unpaired, one-way analysis of variance in which the mean of each group was compared to the mean of every other group. A significance level of 0.05 was used. Significance is shown on the graph according to the following: $P>0.05$ ns, $P\leq0.05*$, $P\leq0.01$, $P\leq0.001*$, $P\leq0.0001****$.
Figure 3B:
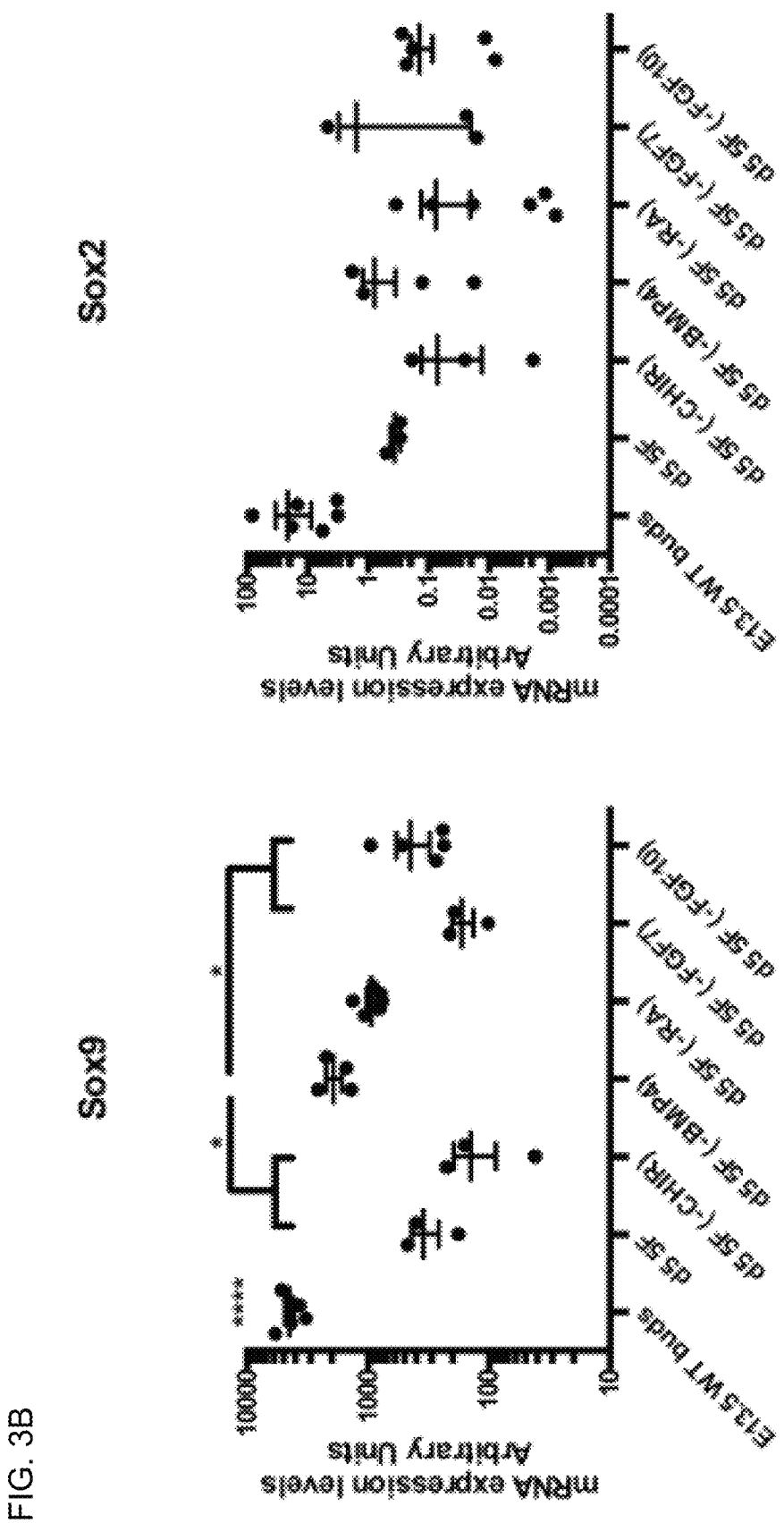
Figure 4A:
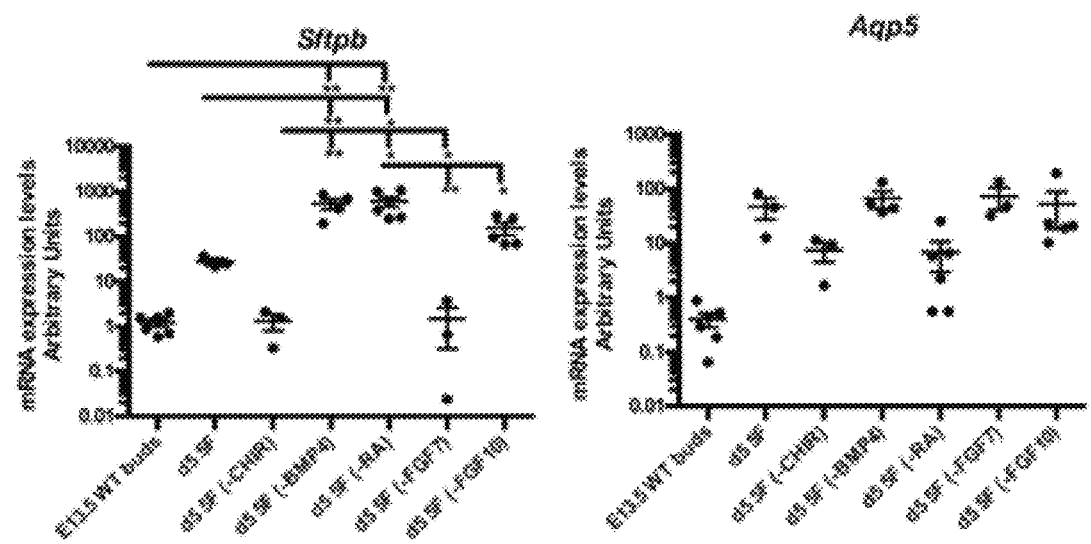
FIG. 4A-B: Synergistic activity of FGF7, CHIR-99021 and RA expands Sox9-lineage labeled murine distal epithelial lung progenitors. E13.5 mouse lung buds were explanted and grown with 5F media, and 5F minus one growth factor. Gene expression was examined in each condition after 2 weeks in culture for differentiation markers of alveolar cell types (A) and airway cell types (B), including Aqp5 (AECI), Sftpb (AECII), p63 (basal cell), Foxj1 (multiciliated cells), Scgb1a1 (club cells). Each data point represents an independent biological replicate and graphs indicate the mean+/−the standard error of the mean for each experimental group.
Figure 4B:
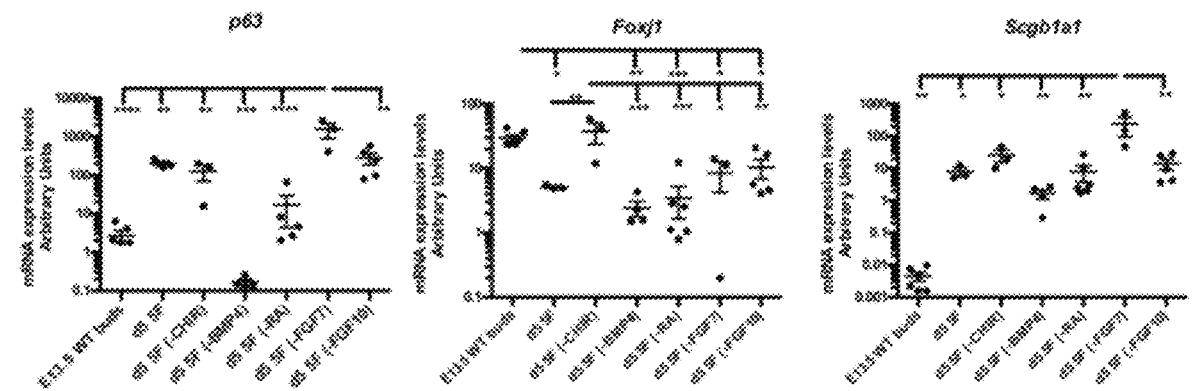

Given that FGF7 promoted robust expansion of distal buds in vitro, but was also permissive for differentiation, experiments were conducted to identify additional growth factors that interacted with FGF signaling to maintain the undifferentiated SOX9+ distal progenitor cell state in vitro. To do this, experiments were conducted that returned to the strategy of using 5F media, and removed one additional growth factor at a time to examine the effect on growth, and expression of Sox9 and Sox2 as markers of distal progenitor and proximal airway cells, respectively. Removing any single factor (FGF10, CHIR-99021, RA or BMP4) from '5F' culture media did not affect the ability of isolated buds to expand (FIG. 3A; 5F control condition presented in FIG. 1D). QRT-PCR analysis of buds after 5 days in culture showed that removing BMP4 led to a statistically significant increase in Sox9 expression levels when compared to other culture conditions (FIG. 3B), and led to gene expression levels that were closest in expression levels of freshly isolated wild type (WT) E13.5 lung buds (FIG. 3B). Sox2 gene expression was generally low in freshly isolated E13.5 lung buds, and in all culture conditions after 5 days in vitro (FIG. 3B). Experiments were also conducted that assessed markers for several genes expressed in differentiating cells (FIG. 4A-B), and noted that the removal of BMP4 from the 5F media also resulted in a significant increase in Sftpb and reduced expression in the proximal markers p63, Foxj1 and Scgb1a1 (FIG. 4A-B). Collectively, this data indicated that removing BMP4 from the media was ideal for supporting an environment with low expression proximal airway markers and high Sox9.

Figure 3C:
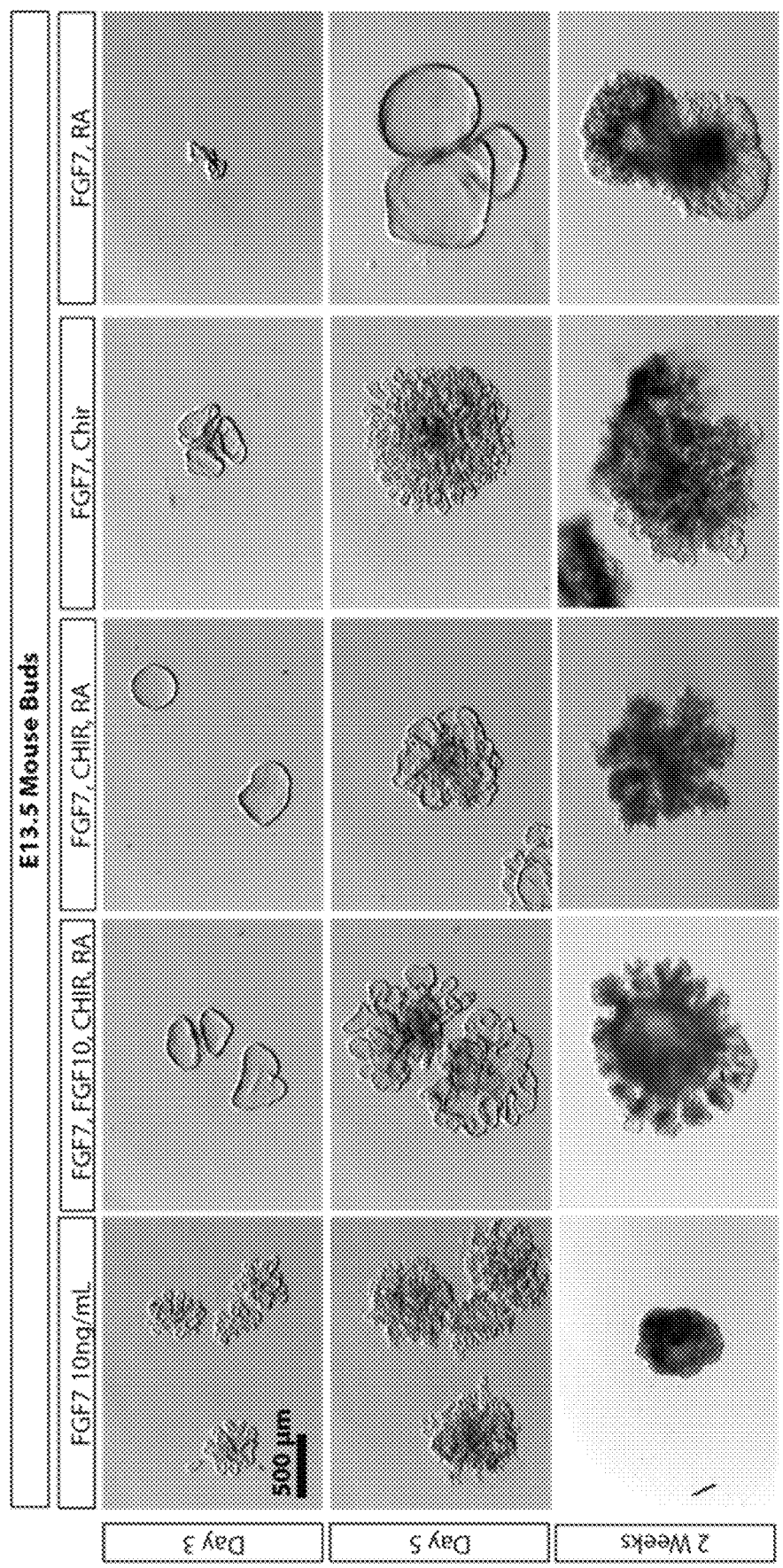
FIG. 3C-D: After removing BMP4, the minimum combination of factors that interact with FGF7 to promote growth (C) and maintain high expression of distal progenitor markers was assessed. Treatment with '4F' media (FGF7/FGF10/CHIR-99021/RA) or '3F' media (FGF7/CHIR-99021/RA) led to growth and had the highest levels of Sox9 expression when compared to FGF7 alone. All groups exhibited maintenance of the progenitor markers Id2 and N-myc and had low levels of proximal marker Sox2. Each data point in (D) represents an independent biological replicate. Scale bar represents 500 um.
Figure 3D:
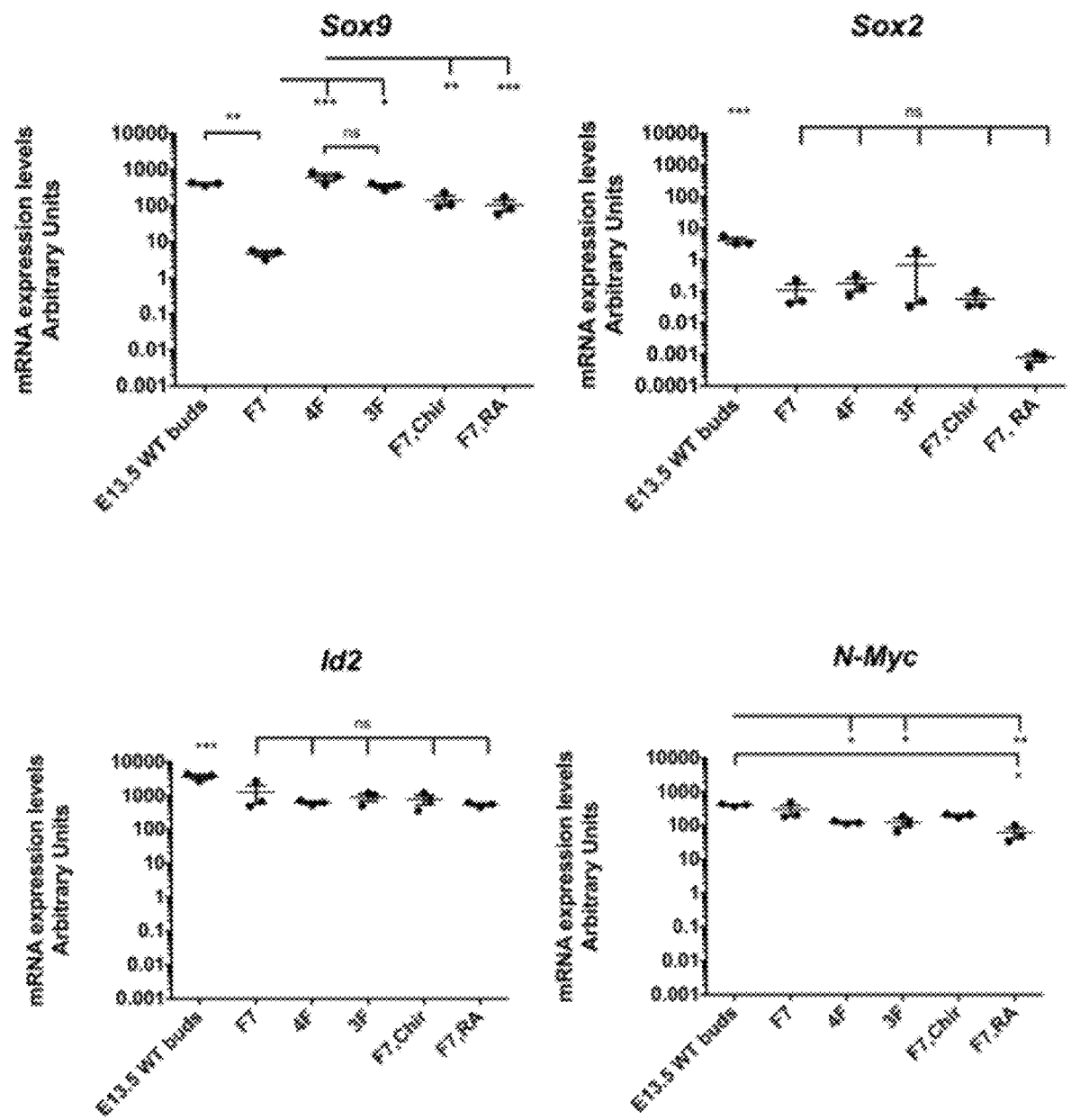
Figure 3F:
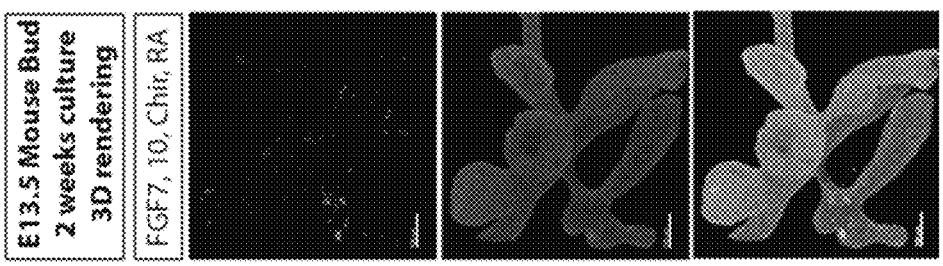
FIG. 3E-F: Section and whole mount immunohistochemical staining analysis confirmed that 3F and 4F conditions maintained robust SOX9 protein staining.
Figure 3E:
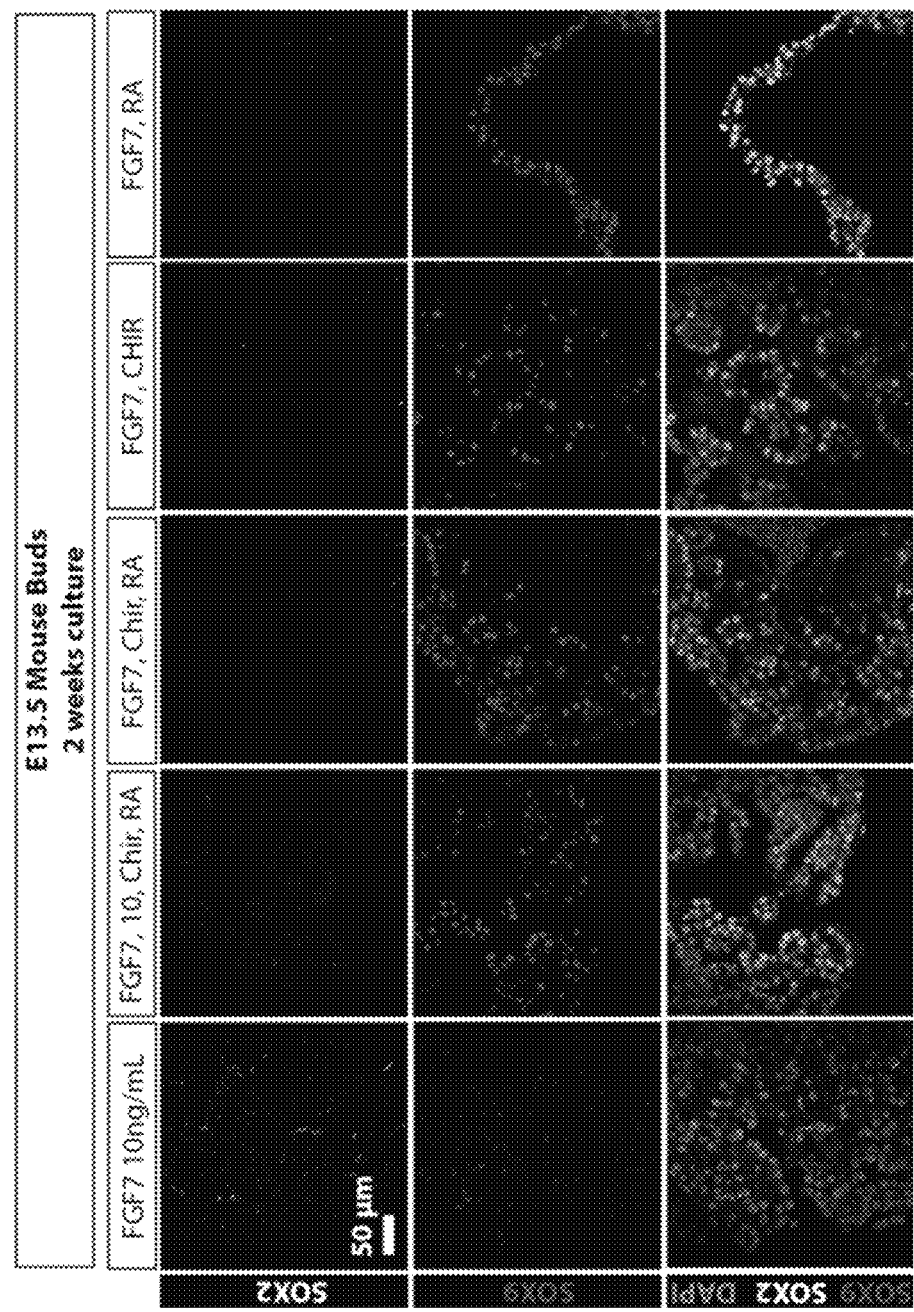
Figure 4C:
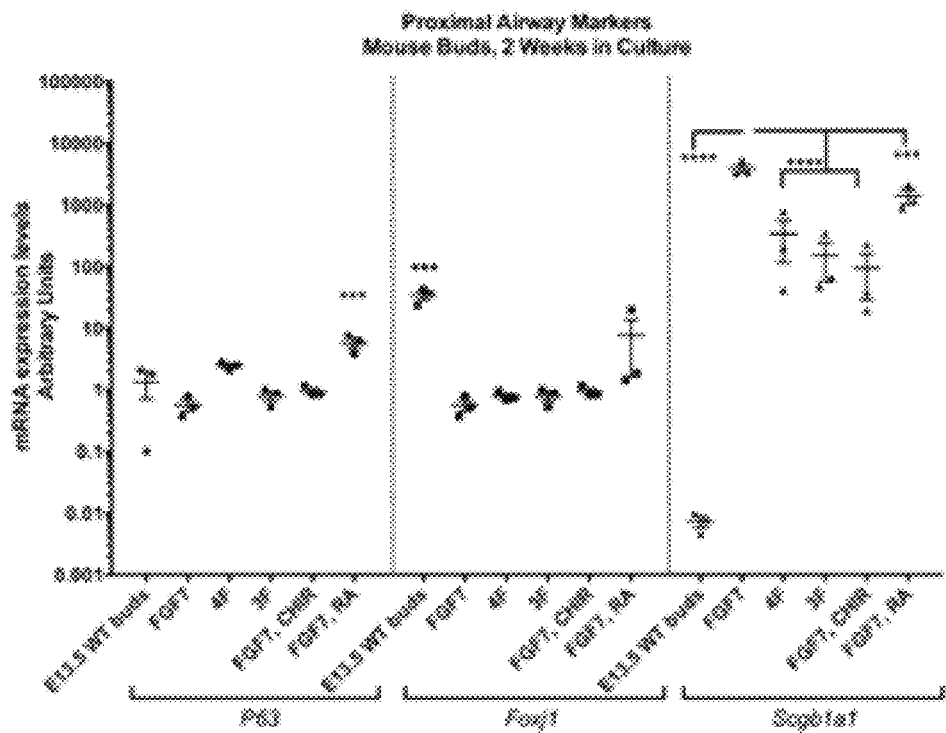
FIG. 4C-D: E13.5 mouse lung buds were explanted and grown with different combinations of growth factors, including '4F' media (FGF7/FGF10/CHIR-99021/RA) or '3F' media (FGF7/CHIR-99021/RA), in addition to FGF7/CHIR-99021 and FGF7/RA. Gene expression for proximal airway markers (C) and maintained levels of mature proximal (C) and distal alveolar (D) markers were assessed after 2 weeks in culture. Each data point represents an independent biological replicate and graphs indicate the mean+/−the standard error of the mean for each experimental group.
Figure 4D:
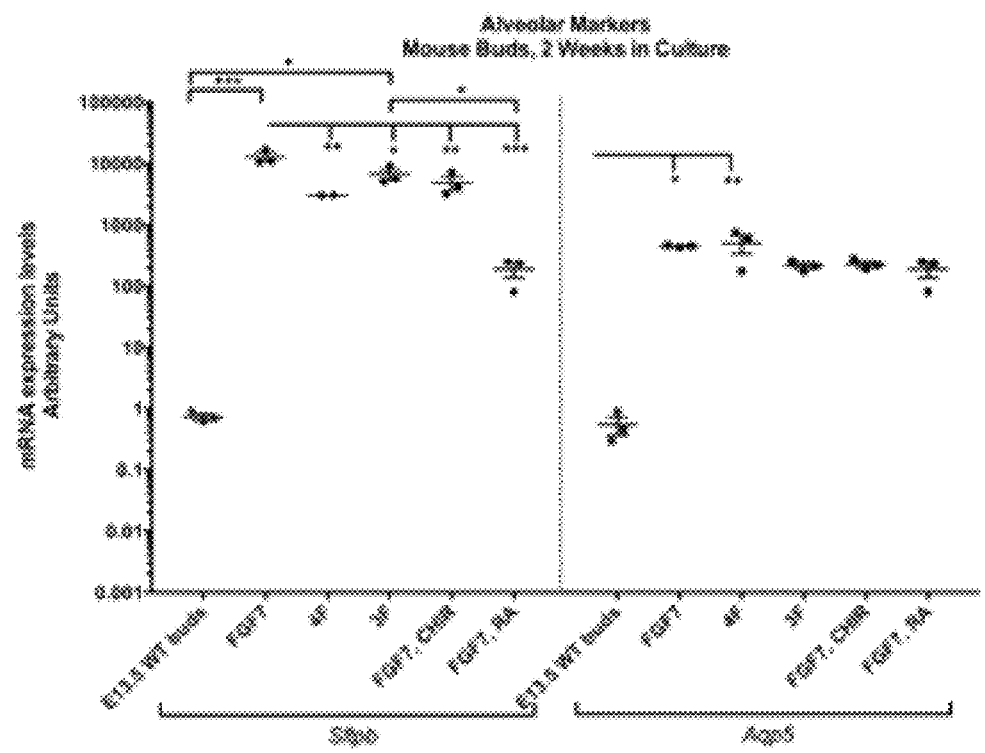
Figure 4E:
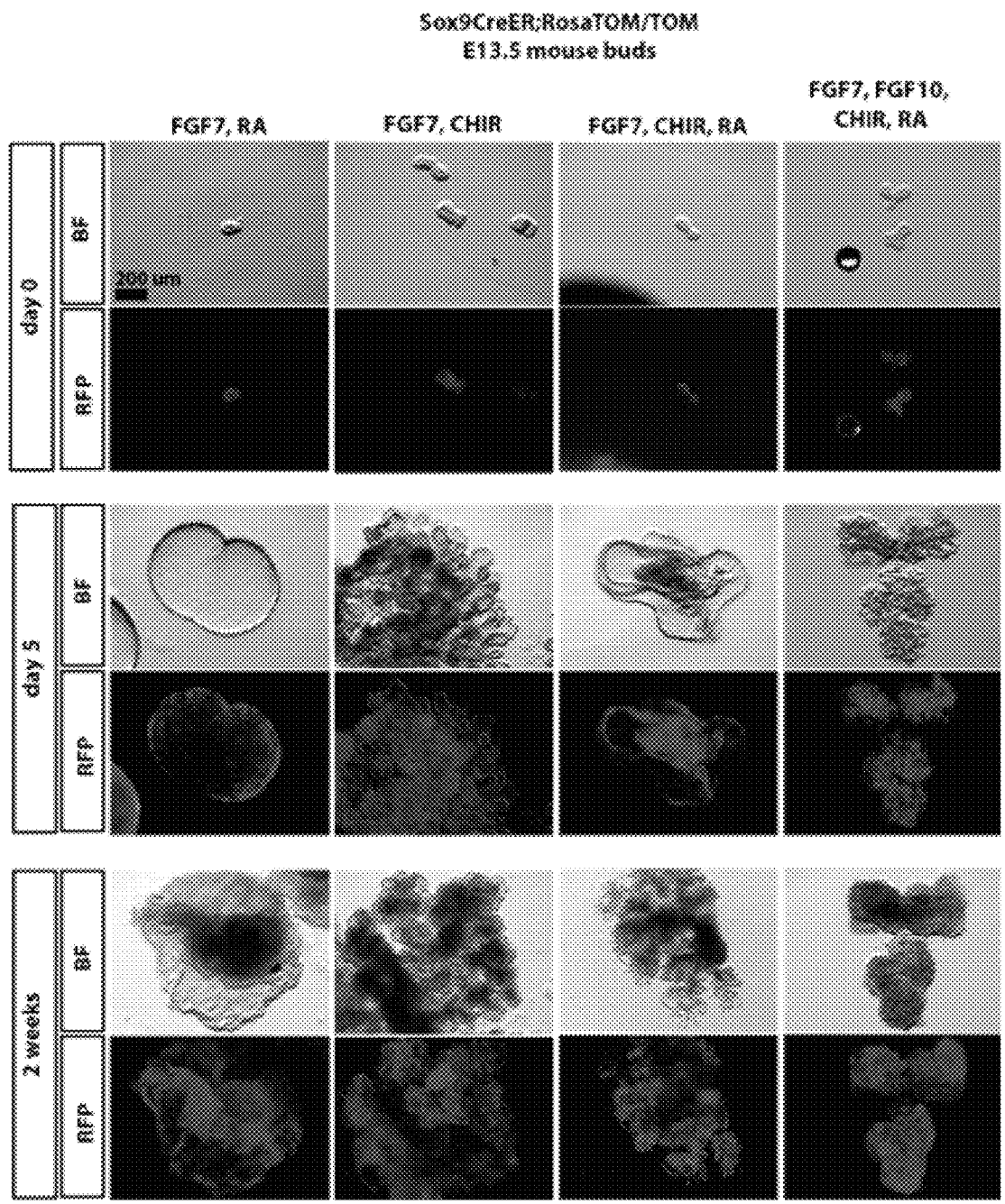
FIG. 4E: Sox9-Cre$^{ER}$; Rosa26$^{Tomato}$ lungs were induced with Tamoxifen 24 hours prior to isolation of the buds, which were isolated and cultured at E13.5. Lineage labeled buds demonstrated that labeled cells expanded in culture over the course of two weeks in all conditions tested. Scale bar represents 200 um.
Figure 4F:
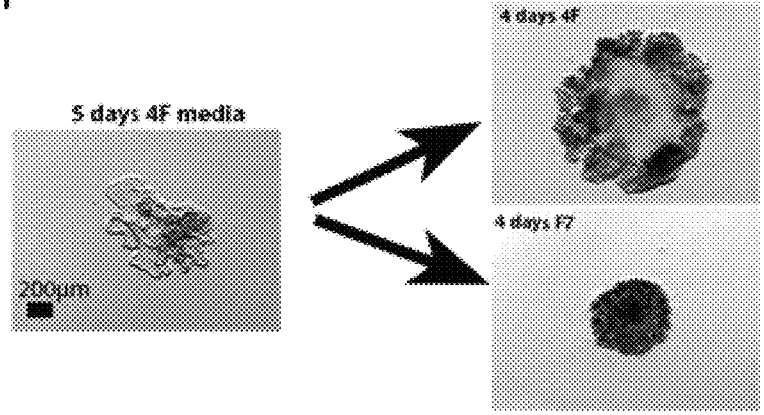
FIG. 4F: To identify whether cultured lung buds were able to undergo phenotypic maturation, buds were grown for 5 days in 4F media and then either maintained for an additional 4 days in 4F media or switched to FGF7 alone. Scale bar represents 200 um.

Experiments next screened combinations of the remaining factors to determine a minimal set that promoted tissue expansion while maintaining the identity of distal epithelial progenitor cells. All conditions included FGF7 (10 ng/mL) due to its ability to potently support proliferation and tissue expansion (FIG. 1, and FIG. 2). FGF10 (10 ng/mL), CHIR-99021 (3 uM) and RA (50 nM) were added in combination with FGF7 and the effect on growth, gene and protein expression was observed after two weeks in culture (FIG. 3C-E). It was found that all conditions supported robust growth (FIG. 3C) and expression of Sox9, Id2 and Nmyc, while maintaining low levels of Sox2 (FIG. 3D). In support of this observation, lineage tracing experiments utilizing Sox9-Cre$^{ER}$; Rosa26$^{Tomato}$ mice, in which Tamoxifen was administered to timed pregnant dams at E12.5 and epithelial lung buds were isolated at E13.5, showed an expansion of labeled progenitors over the 2 week period in culture (FIG. 4E). It was noted that explanted buds treated with 4F or 3-Factor conditions (1F'; FGF7, CHIR-99021, RA) maintained Sox9 mRNA expression at the highest levels, similar to those expressed in freshly isolated epithelial buds at E13.5 (FIG. 3D). Additional QRT-PCR analysis of differentiation markers further suggested that 3F and 4F conditions promoted optimal expression of distal progenitor identity markers while keeping proximal airway marker gene expression low (FIG. 4C-D). Immunofluorescence and whole mount immunostaining of buds after 2 weeks in culture supported QRT-PCR data and showed that 3F and 4F conditions supported robust SOX9 protein expression (FIG. 3E-F).

Figure 4G:
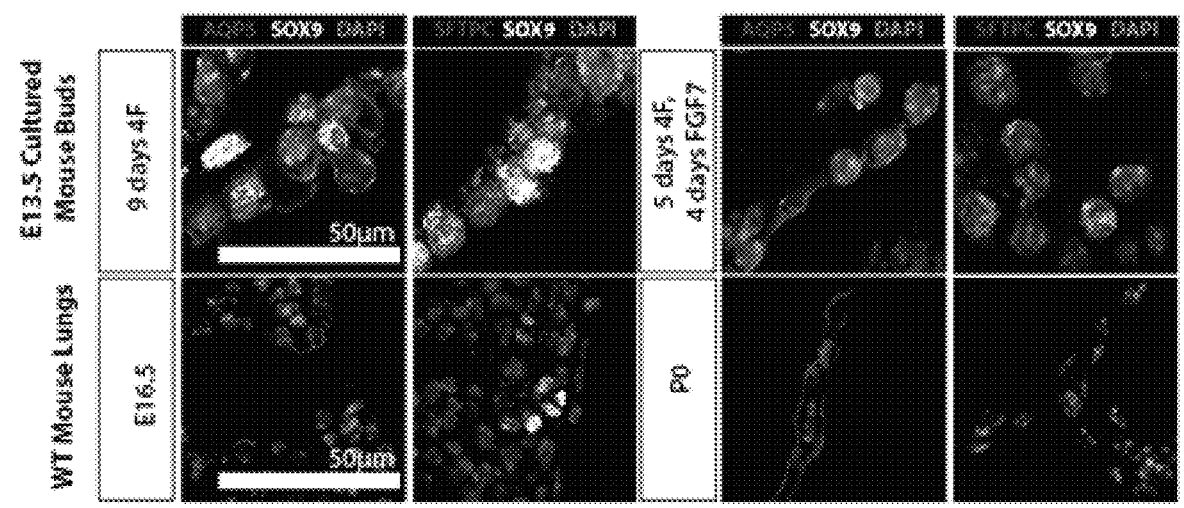
FIG. 4G: After 9 days in culture (as shown in (F)), protein staining for SOX9, SFTPC and AQP5 was carried out (top row), and staining was compared to in vivo developing lungs at E16.5 and P0 (bottom row). Buds grown for 9 days in 4F media possessed many cells that co-expressed SOX9/SFTPC or SOX9/AQP5 whereas those grown in FGF7 media alone contain cells that are positive for AQP5 or SFTPC, but do not express SOX9. Phenotypically, in vitro grown buds that are exposed to FGF7 alone are similar to AQP5+ AECI and SFTPC+ AECII cells in the P0 mouse lung in vivo. Scale bar represents 50 um
Figure 4H:
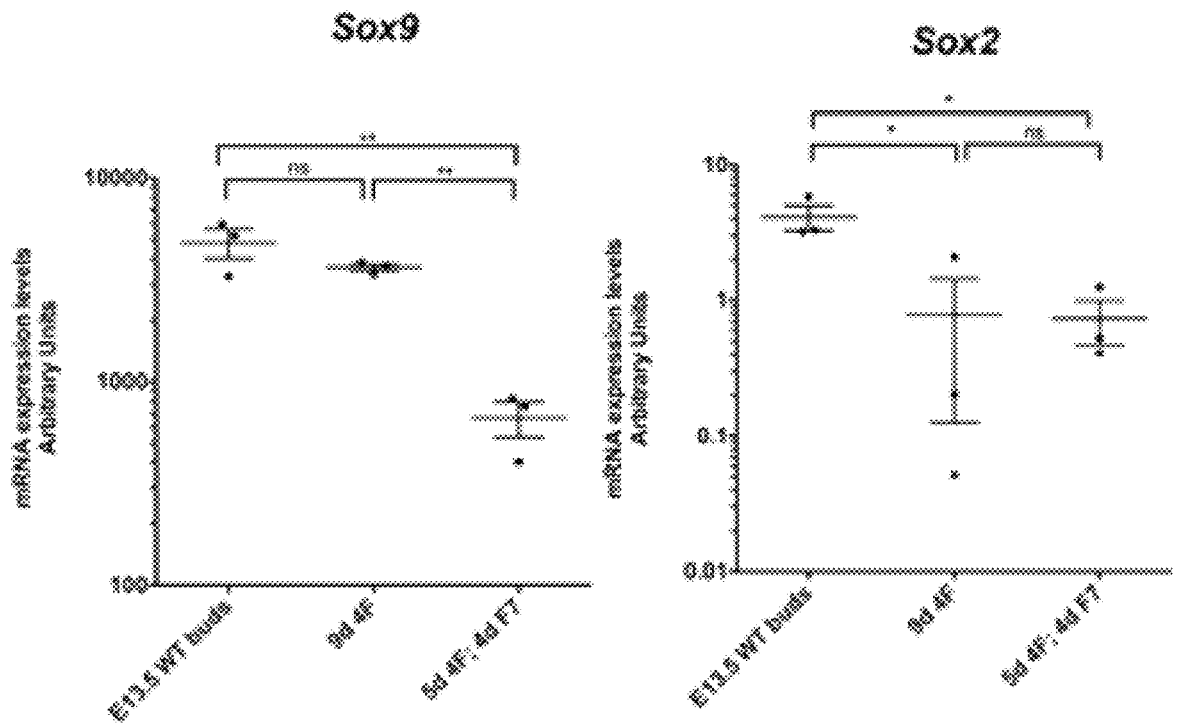
FIG. 4H-J: QRT-PCR analysis after 9 days in culture (as shown in (F)) confirms that Sox9 expression is reduced in buds that are switched to FGF7 media compared to 4F media (H), while the club cell marker Scgb1a1 was increased (J) in buds switched to FGF7 media. Significant changes in other markers were not observed (I-J). Each data point in (H-J) represents an independent biological replicate and graphs indicate the mean+/−the standard error of the mean for each experimental group.
Figure 4I:
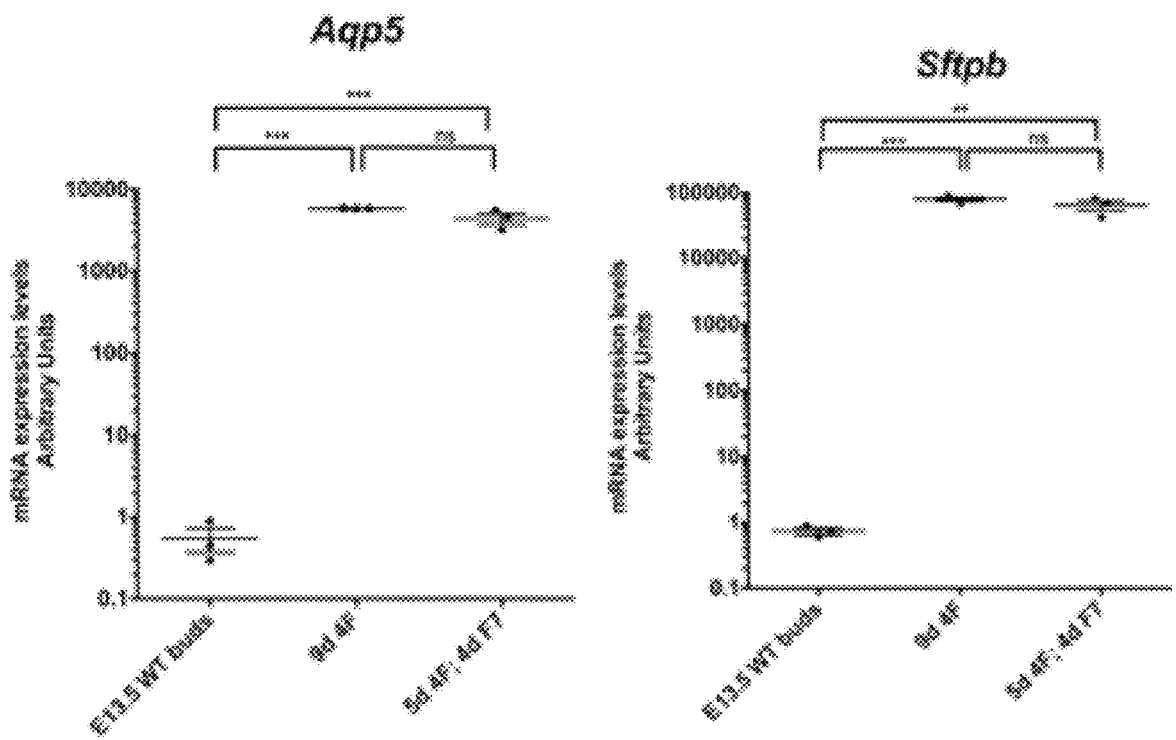
Figure 4J:
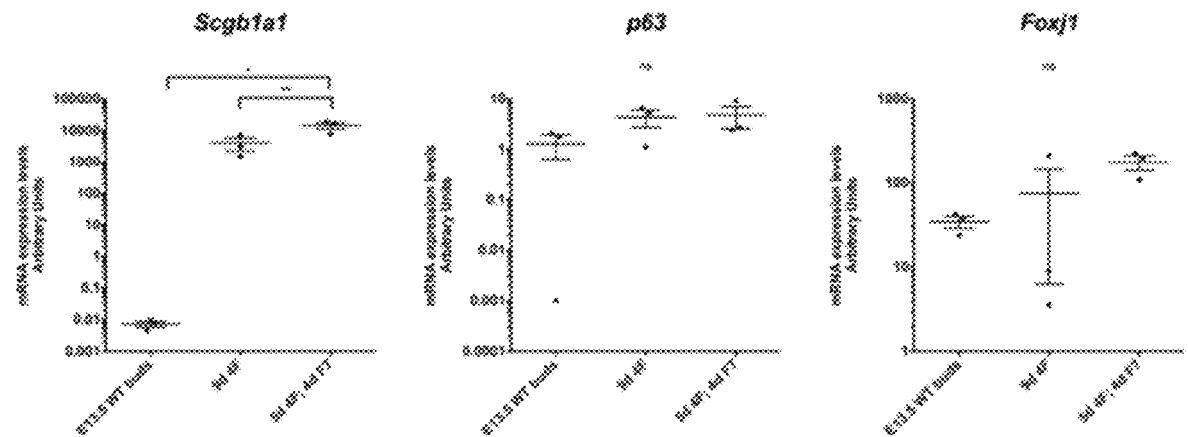

To determine if SOX9+ cells maintained in culture were multipotent and retained the ability to differentiate, experiments were conducted that expanded isolated buds in 4F media for 5 days and then removed FGF10, CHIR-99021 and RA (retaining FGF7 only) for 4 days to determine if SOX9 protein/mRNA expression was reduced and if cells could differentiate (FIG. 4F-J). Compared to controls, which received 4F media for the entire experiment, buds grown in FGF7 exhibited a reduction of SOX9 protein and mRNA expression (FIG. 4G-H). It was noted that many AQP5+ and SFTPC+ cells co-expressed SOX9 in 4F media, whereas tissue grown in FGF7 did not co-express SOX9, suggesting differentiation towards a more mature AECI or AECII-like cell (FIG. 4H). These results Indicated that SOX9+ cells maintained in culture retain the ability to down-regulate distal progenitor gene expression and undergo multi-lineage differentiation.

Example V

This example demonstrates In vitro growth, expansion and maintenance of human fetal distal epithelial lung progenitors.

Given that almost nothing is known about the functional regulation of human fetal distal lung epithelial progenitor cells, experiments were conducted to determine if conditions that maintained mouse distal epithelial progenitors also supported human fetal distal lung progenitor growth and expansion in vitro. Distal epithelial lung buds were enzymatically and mechanically isolated from the lungs of 3 different biological samples at 12 weeks of gestation (84-87 days; n=3) and cultured in a Matrigel droplet (FIG. 5A-B). Surprisingly, while characterizing the isolated buds, whole mount immunostaining revealed that human bud-tip epithelial progenitors express both SOX9 and SOX2 at 12 weeks (FIG. 5C). This is in stark contrast to mice, where SOX9 is exclusively expressed in the distal lung-bud epithelium and SOX2 is exclusively expressed in the proximal airway epithelium (Perl et al., 2005; Rockich et al., 2013). Further investigation of paraffin embedded fetal lungs ranging from 10-19 weeks of gestation revealed that SOX2/SOX9 double-positive cells are present in distal epithelial cells until about 14 weeks gestation (FIG. 5D and FIG. 6C). By 16 weeks, SOX9 and SOX2 became localized to the distal and proximal epithelium, respectively, and were separated by a SOX9/SOX2-negative transition zone, which continued to lengthen throughout development (FIG. 6C). Similar to isolated mouse lung bud cultures, it was observed that FGF7 promoted robust growth in vitro after 2 and 4 weeks, but resulted in reduced growth after 6 weeks in culture (FIG. 5E). However, all other groups tested permitted expansion and survival of buds in culture for 6 weeks or longer (FIG. 5E). Human fetal buds exposed to 3F or 4F supported robust protein and mRNA expression of the distal progenitor markers SOX9, ID2 and NMYC (FIG. 5F-H). In contrast, culture in only 2 factors (FGF7+CHIR-99021, or FGF7+RA) did not support robust distal progenitor marker expression (FIG. 5F-H). Buds cultured in 3F or 4F media also had lower expression of the proximal airway markers P63 and SCGB1A1 (FIG. 6A-B). In stark contrast to results in distal progenitors from mice, SOX2 was also robustly expressed in the 3F and 4F conditions in human fetal buds (FIG. 5H). Whole mount protein staining of SOX2 and SOX9 in buds treated with 3F media confirmed that almost all cells co-express SOX2 and SOX9, similar to native human lung buds in fetal lungs younger than 16 weeks.

Such analysis demonstrated that 3F and 4F media functioned in a similar manner in human fetal buds, and suggested that the addition of FGF10 to the media did not have a significant effect on bud growth or differentiation. Experiments were conducted to further examine the effect of FGF10 on human fetal lung buds in culture by exposing them to high concentrations of FGF10 (500 ng/mL). It was observed that high concentrations of FGF10 induced only modest growth when compared to control conditions (basal media) (FIG. 6D). On the other hand, the addition of a Rho-kinase inhibitor (Y27632) in combination with FGF10, but not alone, promoted growth of buds into larger cyst-like structures (FIG. 6D). These results further support the notion that even at high concentrations, FGF10 alone does not have strong mitogenic effects on the human distal progenitor epithelium in vitro. Collectively, such data showed that a combination of FGF7, RA and activation of Wnt signaling (via CHIR-99021) is a minimal essential combination that promotes growth and maintain distal progenitor identity over time in culture.

Example VI

This example demonstrates that 3F media induces a distal lung bud progenitor-like population of cells in hPSC-derived lung organoids.

Given the robustness by which 3F media supported mouse and human lung bud progenitor growth and identity, experiments sought to determine whether these culture conditions could promote a distal epithelial lung progenitor-like population from hPSCs. NKX2.1+ ventral foregut spheroids were generated as previously described (Dye et al., 2016a; 2015), and were cultured in a droplet of Matrigel and overlaid with media containing 3F (FGF7, CHIR-99021, RA). Spheroids were considered to be "day 0" on the day they were placed in Matrigel. Organoids (called Human Lung Organoids; HLOs) grown in 3F media exhibited robust and stereotyped growth patterns and survived in culture for over 16 weeks (FIG. 7A-B, FIG. 8A-B). Epithelial structures grew first as cystic structures over the course of 2 weeks, followed by a period of epithelial folding that occurred between weeks 3-4 (FIG. 7A; FIG. 8C-D). Around 5-6 weeks in culture, the epithelial structures began forming bud-like structures that resembled human fetal epithelial distal bud tips that underwent bifurcations (FIG. 7A-B; FIG. 8D—bottom row). HLOs were passaged by gently removing Matrigel and replating in a fresh droplet while preserving structural integrity. In this way, HLOs were able to grow for over 16 weeks in culture while retaining their original shape. HLOs could also be passaged using mechanical shear through a 27-gauge needle, followed by embedding in fresh Matrigel and 3F media (FIG. 8E). Following passage, HLOs robustly re-established many small cysts that were expanded and serially passaged every 7-10 days many times (FIG. 8F). The majority of HLO cysts formed from needle passaging were composed of cells with SOX2 and SOX9 nuclear co-staining (FIG. 8G), suggesting that a population of SOX2/SOX9 double positive cells can be expanded easily in culture.

HLOs cultured in 3F media exhibited robust Nkx2.1 protein expression, a lung epithelial marker, in all cells (FIG. 7C); however, it is worth noting that mRNA expression levels of Nkx2.1 were significantly lower than expression levels in the native human fetal lung (FIG. 9E).

In addition to the cystic epithelial phenotype noted above, it was also observed organoids that possessed a dense phenotype (FIG. 9A-D). Dense organoids made up the majority of structures in FGF7-only growth conditions, whereas they made up about ~20% of cultures in 3F media. Approximately 35% of organoids in 3F media were made up of mixed structures (dense+epithelial) (FIG. 9B). Dense structures consisted of cells expressing AECI cell markers HOPX and PDPN that were negative for ECAD (FIG. 9C-D), consistent with adult human AECI cells (Kaarteenaho et al., 2010). No staining for the mature AECII marker SFTPB was observed in dense structures (FIG. 9C). Because of interest in studying the regulation of distal tip progenitor-like cells, experiments focused on epithelial organoids for the remainder of the analysis.

Example VII

This example demonstrates 3F HLOs maintain regions of SOX9+/SOX2+ distal progenitor-like cells for over 115 days in culture and exhibit proximal-distal patterning.

After 40 days in culture, 3F HLOs display clear proximal-distal patterning that mimics what is seen in the developing human lung. Small buds at the periphery of the HLOs stain positive for SOX2 and SOX9 (FIG. 7D), similar to what is seen in the native human fetal lung during early branching (FIG. 5D; FIG. 6C), whereas interior regions of the HLOs are positive only for SOX2 staining (FIG. 7D). SOX9+/SOX2+ peripheral regions persist until at least 115 days in culture (FIG. 7E), although the bud regions become more cystic as the HLOs age past 8 weeks. QRT-PCR analysis confirmed that SOX2, NMYC, and ID2 expression levels are not significantly different between the embryonic human lung and 54 day HLOs (FIG. 7F) while the expression of mature markers are reduced in HLOs compared to human fetal lungs (FIG. 9G-H). Similarly, QRT-PCR analysis of isolated human buds versus isolated bud regions from HLOs confirmed that HLO buds have a similar transcriptional profile to isolated 12-week human buds (FIG. 7G).

Example VIII

This example demonstrates interior regions of 3F HLOs contain secretory cells.

Interior regions of the HLOs showed protein staining for SCGB1A1, a marker of club cells, and MUCSAC, a marker of goblet cells, two prominent secretory cell types of the human proximal airway (FIG. 7H-I). It was also observed Acetylated-Tubulin (AcTub) accumulation on the apical surface of many cells, a marker of multiciliated cells (FIG. 7H); however, these cells did not have bona fide cilia. It was also observed the build-up of a dark, sticky substance within HLOs beginning around 6-7 weeks of culture (FIG. 7A), and Periodic Acid Shift, Alcian Blue (PAS/AB) staining suggested that this was secreted mucous. Staining clearly shows cells within the HLOs that are positive for mucin, as well as secreted mucus in the lumen of HLOs, similar to what is seen in the adult human lung (FIG. 7J).

Example IX

This example demonstrates that removal of CHIR-99021 and RA promotes differentiation within HLOs.

Based on results in the mouse showing that FGF7 was permissive for differentiation (FIG. 1), experiments were conducted that hypothesized that removing CHIR-99021 and RA from HLOs grown in 3F media would reduce the number of progenitor cells and increase differentiation of mature cell types within HLO cultures. Foregut spheroids were collected and grown in 3F media for 42 days and were cultured for an additional 26 days in 3F media (control) or media containing FGF7 only (FIG. 10A). Morphologically, HLOs cultured in FGF7 lost the peripheral bud-like regions compared to 3F HLOs (FIG. 10B). At the end of the experiment, cultures were collected and assessed for gene and protein expression. While 3F HLOs maintained budded peripheral regions containing cells with nuclear SOX9 and SOX2, HLOs grown in FGF7-only did not exhibit any SOX9/SOX2 double positive cells and instead contained regions with cells containing cytoplasmic SOX9 and separate regions where cells expressed nuclear SOX2 (FIG. 10C). QRT-PCR analysis of SOX9 showed no change in the amount of SOX9 transcript, but a significant increase in SOX2 transcript in the FGF7 treated HLOs was observed (FIG. 10D).

HLOs treated with FGF7 also exhibited an increase in many mature cell types as observed both by protein staining and QRT-PCR analysis. Most strikingly, FGF7-only HLOs exhibited a large increase in the number of MUC5AC positive cells, a dramatic increase the amount of mucous within the HLO lumens (FIG. 10E), as well as a significant increase in gene expression of MUC5AC (FIG. 10F). Interestingly, there was not an obvious increase in the number of SCGB1A1+ cells observed by protein staining (FIG. 10I). Although expression levels of SCGB1A1 were increased almost 100-fold in FGF7-only HLOs over the 3F controls, this difference was not statistically significant (FIG. 10F). FGF7 treated HLOs also contained cells that stained positive for P63, a marker of basal stem cells (FIG. 10G), and exhibited a significant increase in mRNA expression of P63 (FIG. 10H). In contrast, P63+ cells were conspicuously absent from 3F epithelial HLOs. (FIG. 10G-H, see also FIG. 7H). Although mRNA expression of the proximal ciliated cell marker FOXJ1 increased significantly in HLOs treated with FGF7-only (FIG. 10O), obvious FOXJ1 protein expression was not detected by immunofluorescence (negative data not shown).

In addition to an increase expression of multiple proximal airway cell markers, HLOs grown in FGF7-only exhibited an increase in both protein and mRNA expression of the AECII marker SFTPC (FIG. 10K-L) and possessed cells that stained positive for the AECI marker PDPN, and had increased gene expression of the AECI marker HOPX (FIG. 10M-N). Together, these results demonstrate that HLOs grown in 3F media have the ability to generate multiple mature lung cell lineages when CHIR-99021 and RA is removed from the media.

Example X

This example describes the materials and methods for Examples I-IX.

Mouse Models:

All animal research was approved by the University of Michigan Committee on Use and Care of Animals. Lungs from Sox9-eGFP (MGI ID:3844824), Sox9CreER; Rosa$^{Tomato/Tomato}$ (MGI ID:5009223 and 3809523)(Kopp et al., 2011), or wild type lungs from CD1 embryos (Charles River) were dissected at embryonic day (E) 13.5, and buds were isolated as described below and as previously described (del Moral and Warburton, 2010).

Human Fetal Lung Tissue:

All research utilizing human fetal tissue was approved by the University of Michigan institutional review board. Normal human fetal lungs were obtained from the University of Washington Laboratory of Developmental Biology, and epithelial lung buds were dissected as described below. All experiments were repeated using tissues from 3 individual lungs; 84 day post fertilization of unknown gender, 87 day post fertilization male, and 87 day post fertilization of unknown gender. All tissues were shipped in Belzer's solution at 4 degrees Celsius and were processed and in culture within 24 hours of isolation.

Cell Lines and Culture Conditions:

Mouse and Human Primary Cultures:

Isolated mouse buds were cultured in 4-6 µl droplets of matrigel, covered with media, and kept at 37 degrees Celsius with 5% Carbon Dioxide. Isolated human fetal lung buds were cultured in 25-50 µl droplets of matrigel, covered with media, and kept at 37 degrees Celsius with 5% Carbon Dioxide.

Generation and Culture of hPSC-Derived Lung Organoids:

The University of Michigan Human Pluripotent Stem Cell Research Oversight (hPSCRO) Committee approved all experiments using human embryonic stem cell (hESC) lines. hESC line UM63-1 (NIH registry #0277) was obtained from the University of Michigan and hESC line H9 (NIH registry #0062) was obtained from the WiCell Research Institute. ES cell lines were routinely karyotyped to ensure normal karyotype and ensure the sex of each line (H9-XX, UM63-1-XX). Cells are monitored for *mycoplasma* infection monthly using the MycoAlert *Mycoplasma* Detection Kit (Lonza). Stem cells were maintained on hESC-qualified Matrigel (Corning Cat#354277) using mTesR1 medium (Stem Cell Technologies). hESCs were maintained and passaged as previously described (Spence et al., 2011) and ventral foregut spheroids were generated as previously described (Dye et al., 2016a; 2015). Following differentiation, free-floating foregut spheroids were collected from differentiated stem cell cultures and plated in a matrigel droplet on a 24-well tissue culture grade plate.

Isolation and Culture of Mouse Lung Epithelial Buds

Mouse buds were dissected from E13.5 embryos. For experiments using Sox9CreER; Rosa$^{Tomato/Tomato}$ mice, 50 ug/g of tamoxifen was dissolved in corn oil and given by oral gavage on E12.5, 24 hours prior to dissection. Briefly, in sterile environment, whole lungs were placed in 100% dispase (Corning Cat#354235) on ice for 30 minutes. Lungs were then transferred using a 25 uL wiretrol tool (Drummond Scientific Cat#S5-000-2050) to 100% FBS (Corning Cat#35-010-CV) on ice for 15 minutes, and then transferred to a solution of Dulbecco's Modified Eagle Medium: Nutrient Mixture F12 (DMEM/F12, ThermoFisher SKU#12634-010) with 10% FBS and 1× Pennicillin-Streptomycin (ThermoFisher Cat#15140122) on ice. To dissect buds, a single lung or lung lobe was transferred by wiretrol within a droplet of media to a 100 mm sterile petri dish. Under a dissecting microscope, the mesenchyme was carefully removed and epithelial bud tips were torn away from the bronchial tree using tungsten needles (Point Technologies, Inc.). Care was taken to remove the trachea and any connective tissue from dissected lungs. Isolated bud tips were picked up using a p20 pipette and added to an eppendorf tube with cold Matrigel (Corning Ref#354248) on ice. The buds were picked up in a p20 pipette with 4-6 uL of Matrigel and plated on a 24-well tissue culture well (ThermoFisher Cat#142475). The plate was moved to a tissue culture incubator and incubated for 5 minutes at 37 degrees Celsius and 5% CO2 to allow the Matrigel droplet to solidify. 500 uL of media was then added to the dish in a laminar flow hood. Media was changed every 2-3 days.

Isolation and Culture of Human Fetal Lung Epithelial Buds

Distal regions of 12 week fetal lungs were cut into ~2 mm sections and incubated with dispase, 100% FBS and then 10% FBS as described above, and moved to a sterile petri dish. Mesenchyme was removed by repeated pipetting of distal lung pieces after dispase treatment. Buds were washed with DMEM until mesenchymal cells were no longer visible in the media. Buds were then moved to a 1.5 mL eppendorf tube containing 200 uL of Matrigel, mixed using a p200 pipette, and plated in ~20 uL droplets in a 24 well tissue culture plate. Plates were placed at 37 degrees Celsius with 5% CO2 for 20 minutes while droplets solidified. 500 uL of media was added to each well containing a droplet. Media was changed every 2-3 days.

EdU Quantification by Flow Cytometry

Epithelial lung buds were dissected from e13.5 CD1 mice and plated in a matrigel droplet as described above. 3-4 individual buds from one mouse were placed in each droplet and were pooled to serve as a single biological replicate. Three droplets (corresponding to 3 independent biological samples) were assigned to each experimental group, receiving either 1, 10, 50 or 100 ng/mL of FGF7 for 7 days. Media was changed every 2-3 days. Cells were incubated with EdU for 1 hour and stained with the Click-It EdU Alexa Fluor 488 system (ThermoFisher Cat# C10337) according to the manufacturer's instructions. As a control, wells that received 10 ng/mL of FGF7 for 7 days were taken through the EdU steps but were not stained were used to set the gates. For analysis, lung buds were broken into a single cell suspension. 1 mL of accutase (Sigma Cat# A6964) was added to a 15 mL conical tube containing pooled epithelial buds and cells were incubated at 37 degrees Celsius with frequent visual inspection until clumps of cells were no longer visible. 3 mL of basal media (see below) was added to each tube, and cells were centrifuged at 300 g for 5 minutes at 4 degrees Celsius. The supernatant was then withdrawn, and cells were resuspended with 1 mL sterile PBS, filtered through a 70 uM strainer to remove any cell clumps and transferred to a cell sorting tube. Flow cytometric analysis was performed on a BD FACSARIA III cell sorter (BD biosciences).

Culture Media, Growth Factors and Small Molecules

Low-Serum Basal Media

All mouse bud, human fetal bud, and hPSC-derived human lung organoids were grown in low-serum basal media (basal media) with added growth factors. Basal media consisted of Dulbecco's Modified Eagle Medium: Nutrient Mixture F12 (DMEM/F12, ThermoFisher SKU#12634-010) supplemented with 1× N2 supplement (ThermoFisher Catalog#17502048) and 1λ B27 supplement (ThermoFisher Catalog#17504044), along with 2 mM Glutamax (ThermoFisher Catalog#35050061), 1× Pennicillin-Streptomycin (ThermoFisher Cat#15140122) and 0.05% Bovine Serum Albumin (BSA; Sigma product# A9647). BSA was weighed and dissolved in DMEM F/12 media before being passed through a SteriFlip 0.22 uM filter (Millipore Item# EW-29969-24) and being added to basal media. Media was stored at 4 degrees Celsius for up to 1 month. On the day of use, basal media was aliquoted and 50 ug/mL Ascorbic acid and 0.4 uM Monothioglycerol was added. Once ascorbic acid and monothioglycerol had been added, media was used within one week.

Growth Factors and Small Molecules

Recombinant Human Fibroblast Growth Factor 7 (FGF7) was obtained from R&D systems (R&D #251-KG/CF) and used at a concentration of 10 ng/mL unless otherwise noted. Recombinant Human Fibroblast Growth Factor 10 (FGF10) was obtained either from R&D systems (R&D #345-FG) or generated in house (see below), and used at a concentration of 10 ng/mL (low) or 500 ng/mL (high) unless otherwise noted. Recombinant Human Bone Morphogenic Protein 4 (BMP4) was purchased from R&D systems (R&D Catalog #314-BP) and used at a concentration of 10 ng/mL. All-trans Retinoic Acid (RA) was obtained from Stemgent (Stemgent Catalog#04-0021) and used at a concentration of 50 nM. CHIR-99021, a GSK3β inhibitor that stabilizes β-CATENIN, was obtained from STEM CELL technologies (STEM CELL Technologies Catalog#72054) and used at a concentration of 3 uM. Y27632, a ROCK inhibitor (APExBIO Cat# A3008) was used at a concentration of 10 uM.

Generation and Isolation of Human Recombinant FGF10

Recombinant human FGF10 was produced in-house. The recombinant human FGF10 (rhFGF10) expression plasmid pET21d-FGF10 in *E. coli* strain BL21trxB(DE3) was a gift from James A. Bassuk at the University of Washington School of Medicine (Bagai et al., 2002). *E. coli* strain was grown in standard LB media with peptone derived from meat, carbenicillin and glucose. rhFGF10 expression was induced by addition of isopropyl-1-thio-β-D-galactopyranoside (IPTG). rhFGF10 was purified by using a HiTrap-Heparin HP column (GE Healthcare, 17040601) with step gradients of 0.5M to 2M LiCl. From a 200 ml culture, 3 mg of at least 98% pure rFGF-10 (evaluated by SDS-PAGE stained with Coomassie Blue R-250) was purified. rFGF10 was compared to commercially purchased human FGF10 (R&D Systems) to test/validate activity based on the ability to phosphorylate ERK1/2 in an A549 alveolar epithelial cell line (ATCC Cat#CCL-185) as assessed by western blot analysis.

RNA Extraction and Quantitative RT-PCR Analysis

RNA was extracted using the MagMAX-96 Total RNA Isolation System (Life Technologies). RNA quality and concentration was determined on a Nanodrop 2000 spectrophotometer (Thermo Scientific). 100 ng of RNA was used to generate a cDNA library using the SuperScript VILO cDNA master mix kit (Invitrogen) according to manufacturer's instructions. qRT-PCR analysis was conducted using Quantitect SYBR Green Master Mix (Qiagen) on a Step One Plus Real-Time PCR system (Life Technologies). Expression was calculated as a change relative to GAPDH expression using arbitrary units, which were calculated by the following equation: [2^(GAPDH Ct−Gene Ct)]×10,000. A Ct value of 40 or greater was considered not detectable. A list of primer sequences used can be found in Table 1.

TABLE 1 qRT-PCR primer sequences

| Species | Gene Target | Forward Primer Sequence | SEQ ID NO: | Reverse Primer Sequence | SEQ ID NO: |
|---|---|---|---|---|---|
| Mouse | aqp5 | TAGAAGATGGCTCGGAGCAG | 1 | CTGGGACCTGTGAGTGGTG | 2 |
| Mouse | foxj1 | TGTTCAAGGACAGGTTGTGG | 3 | GATCACTCTGTCGGCCATCT | 4 |
| Mouse | gapdh | TGTCAGCAATGCATCCTGCA | 5 | CCGTTCAGCTCTGGGATGAC | 6 |
| Mouse | id2 | AGAAAAGAAAAAGTCCCCAAATG | 7 | GTCCTTGCAGGCATCTGAAT | 8 |
| Mouse | nmyc | AGCACCTCCGGAGAGGATA | 9 | TCTCTACGGTGACCACATCG | 10 |
| Mouse | p63 | AGCTTCTTCAGTTCGGTGGA | 11 | CCTCCAACACAGATTACCCG | 12 |
| Mouse | Scgb1a1 | ACTTGAAGAAATCCTGGGCA | 13 | CAAAGCCTCCAACCTCTACC | 14 |
| Mouse | sftp-b | ACAGCCAGCACACCCTTG | 15 | TTCTCTGAGCAACAGCTCCC | 16 |
| Mouse | sox2 | AAAGCGTTAATTTGGATGGG | 17 | ACAAGAGAATTGGGAGGGGT | 18 |
| Mouse | sox9 | TCCACGAAGGGTCTCTTCTC | 19 | AGGAAGCTGGCAGACCAGTA | 20 |
| Human | Foxj1 | CAACTTCTGCTACTTCCGCC | 21 | CGAGGCACTTTGATGAAGC | 22 |
| Human | gapdh | AATGAAGGGGTCATTGATGG | 23 | AAGGTGAAGGTCGGAGTCAA | 24 |
| Human | hopx | GCCTTTCCGAGGAGGAGAC | 25 | TCTGTGACGGATCTGCACTC | 26 |
| Human | id2 | GACAGCAAAGCACTGTGTGG | 27 | TCAGCACTTAAAAGATTCCGTG | 28 |
| Human | muc5ac* | GCACCAACGACAGGAAGGATGAG | 29 | CACGTTCCAGAGCCGGACAT | 30 |
| Human | nkx2.1 | CTCATGTTCATGCCGCTC | 31 | GACACCATGAGGAACAGCG | 32 |
| Human | nmyc | CACAGTGACCACGTCGATTT | 33 | CACAAGGCCCTCAGTACCTC | 34 |
| Human | p63 | CCACAGTACACGAACCTGGG | 35 | CCGTTCTGAATCTGCTGGTCC | 36 |
| Human | scgb1a1 | ATGAAACTCGCTGTCACCCT | 37 | GTTTCGATGACACGCTGAAA | 38 |
| Human | sftp-b | CAGCACTTTAAAGGACGGTGT | 39 | GGGTGTGTGGGACCATGT | 40 |
| Human | sox2 | GCTTAGCCTCGTCGATGAAC | 41 | AACCCCAAGATGCACAACTC | 42 |

TABLE 1-continued qRT-PCR primer sequences

| Species | Gene Target | Forward Primer Sequence | SEQ ID NO: | Reverse Primer Sequence | SEQ ID NO: |
|---|---|---|---|---|---|
| Human | sox9 | GTACCCGCACTTGCACAAC | 43 | ATTCCACTTTGCGTTCAAGG | 44 |
| Human | sp-c | AGCAAAGAGGTCCTGATGGA | 45 | CGATAAGAAGGCGTTTCAGG | 46 |

Note:
All primer sequences were obtained from primerdepot.nci.nih.gov (human) or mouseprimerdepot.nci.nih.gov (mouse) unless otherwise noted. All annealing temperatures are near 60° C.
*MUC5AC Huang, SX et al. Efficient generation of lung and airway epithelial cells from human pluripotent stem cells. Nature Biotechnol. 1-11 (2013). doi: 10.1038/nbt.2754

Tissue Preparation, Immunohistochemistry and Imaging Paraffin Sectioning and Staining Mouse bud, human bud, and HLO tissue was fixed in 4% Paraformaldehyde (Sigma) for 2 hours and rinsed in PBS overnight. Tissue was dehydrated in an alcohol series, with 30 minutes each in 25%, 50%, 75% Methanol:PBS/0.05% Tween-20, followed by 100% Methanol, and then 100% Ethanol. Tissue was processed into paraffin using an automated tissue processor (Leica ASP300). Paraffin blocks were sectioned 5-7 uM thick, and immunohistochemical staining was performed as previously described (Spence et al., 2009). A list of antibodies, antibody information and concentrations used can be found in Table 2. PAS Alcian blue staining was performed using the Newcomer supply Alcian Blue/PAS Stain kit (Newcomer Supply, Inc.) according to manufacturer's instructions.

TABLE 2

Antibody information

| Primary Antibody | Source | Catalog # | Used for Species | Dilution (Sections) | Dilution (Whole mount) | Clone |
|---|---|---|---|---|---|---|
| Goat anti-CC10 (SCGB1A1) | Santa Cruz Biotechnology | sc-9770 | Mouse, Human | 1:200 | | C-20 |
| Goat anti-SOX2 | Santa Cruz Biotechnology | Sc-17320 | Mouse, Human | 1:200 | 1:100 | polyclonal |
| Mouse anti-Acetylated Tubulin (ACTTUB) | Sigma-Aldrich | T7451 | Mouse, Human | 1:1000 | | 6-11B-1 |
| Mouse anti-E-Cadherin (ECAD) | BD Transduction Labratories | 610181 | Mouse, Human | 1:500 | | 36/E-Cadherin |
| Mouse anti-Surfactant Protein B (SP-B) | Seven Hills Bioreagents | Wmab-1B9 | Mouse, Human | 1:250 | | monoclonal |
| Rabbit anti-Aquaporin 5 (Aqp5) | Abcam | Ab78486 | Mouse | 1:500 | | polyclonal |
| Rabbit anti-Clara Cell Secretory Protein (CCSP; SCGB1A1) | Seven Hills Bioreagents | Wrab-3950 | Mouse, Human | 1:250 | | polyclonal |
| Rabbit anti-HOPX | Santa Cruz Biotechnology | Sc-30216 | Human | 1:250 | | polyclonal |
| Rabbit anti-NKX2.1 | Abcam | ab76013 | Human | 1:200 | | EP1584Y |
| Rabbit anti-PDPN | Santa Cruz Biotechnology | Sc-134482 | Human | 1:500 | | polyclonal |
| Rabbit anti-Pro-Surfactant protein C (Pro-SPC) | Seven Hills Bioreagents | Wrab-9337 | Human, Mouse | 1:500 | | polyclonal |
| Rabbit anti-P63 | Santa Cruz Biotechnology | sc-8344 | Mouse, Human | 1:200 | | H-129 |
| Rabbit anti-SOX9 | Millipore | AB5535 | Mouse, Human | 1:500 | 1:250 | polyclonal |
| Rat anti-Ki67 | Biolegend | 652402 | Mouse | 1:100 | | 16A8 |
| *Biotin-Mouse anti MUC5AC | Abcam | ab79082 | Human | 1:500 | | Monoclonal |

| Secondary Antibody | Source | Catalog # | Dilution |
|---|---|---|---|
| Donkey anti-goat 488 | Jackson Immuno | 705-545-147 | 1:500 |
| Donkey anti-goat 647 | Jackson Immuno | 705-605-147 | 1:500 |
| Donkey anti-goat Cy3 | Jackson Immuno | 705-165-147 | 1:500 |
| Donkey anti-mouse 488 | Jackson Immuno | 715-545-150 | 1:500 |
| Donkey anti-mouse 647 | Jackson Immuno | 415-605-350 | 1:500 |
| Donkey anti-mouse Cy3 | Jackson Immuno | 715-165-150 | 1:500 |
| Donkey anti-rabbit 488 | Jackson Immuno | 711-545-152 | 1:500 |
| Donkey anti-rabbit 647 | Jackson Immuno | 711-605-152 | 1:500 |
| Donkey anti-rabbit Cy3 | Jackson Immuno | 711-165-102 | 1:500 |
| Donkey anti-goat 488 | Jackson Immuno | 705-545-147 | 1:500 |
| Donkey anti-goat 647 | Jackson Immuno | 705-605-147 | 1:500 |
| Donkey anti-goat Cy3 | Jackson Immuno | 705-165-147 | 1:500 |
| Donkey anti-mouse 488 | Jackson Immuno | 715-545-150 | 1:500 |

TABLE 2-continued

| Antibody information | | | |
|---|---|---|---|
| Donkey anti-mouse 647 | Jackson Immuno | 415-605-350 | 1:500 |
| Donkey anti-mouse Cy3 | Jackson Immuno | 715-165-150 | 1:500 |
| Donkey anti-rabbit 488 | Jackson Immuno | 711-545-152 | 1:500 |
| Donkey anti-rabbit 647 | Jackson Immuno | 711-605-152 | 1:500 |
| Donkey anti-rabbit Cy3 | Jackson Immuno | 711-165-102 | 1:500 |
| Streptavidin 488 | Jackson Immuno | 016-540-084 | 1:500 |

Whole Mount Staining

For whole mount staining tissue was placed in a 1.5 mL eppendorf tube and fixed in 4% paraformaldehyde (Sigma) for 30 minutes. Tissue was then washed with PBS/0.05% Tween-20 (Sigma) for 5 hours, followed by a 2.5-hour incubation with blocking serum (PBS-Tween-20 plus 5% normal donkey serum). Primary antibodies were added to blocking serum and tissue was incubated for at least 24 hours at 4 degrees Celcius. Tissue was then washed for 5 hours with several changes of fresh PBS-Tween-20. Secondary antibodies were added to fresh blocking solution and tissue was incubated for 12-24 hours, followed by 5 hours of PBS-Tween-20 washes. Tissue was then dehydrated to 100% methanol and carefully moved to the center of a single-well EISCO concave microscope slide (ThermoFisher Cat#S99368) using a glass transfer pipette. 5-7 drops of Murray's clear (2 parts Benzyl alcohol, 1 part Benzyl benzoate [Sigma]) were added to the center of the slide, and slides were coverslipped and sealed with clear nail polish.

Imaging and Image Processing

Images of fluorescently stained slides were taken on a Nikon A-1 confocal microscope. When comparing groups within a single experiment, exposure times and laser power were kept consistent across all images. All Z-stack imaging was done on a Nikon A-1 confocal microscope and Z-stacks were 3-D rendered using Imaris software. Brightness and contrast adjustments were carried out using Adobe Photoshop Creative Suite 6 and adjustments were made uniformly among all images.

Brightfield images of live cultures were taken using an Olympus S2×16 dissecting microscope. Image brightness and contrast was enhanced equally for all images within a single experiment using Adobe Photoshop. Images were cropped where noted in figure legends to remove blank space surrounding buds or cultures. Brightfield images of Alcian Blue stains were taken using an Olympus DP72 inverted microscope.

Quantification and Statistical Analysis

All plots and statistical analysis were done using Prism 6 Software (GraphPad Software, Inc.). For statistical analysis of qRT-PCR results, at least 3 biological replicates for each experimental group were analyzed and plotted with the standard error of the mean. If only two groups were being compared, a two-sided student's T-test was performed. In assessing the effect of length of culture with FGF7 on gene expression in mouse buds (FIG. 1G), a one-way, unpaired Analysis of Variance (ANOVA) was performed for each individual gene over time. The mean of each time point was compared to the mean of the expression level for that gene at day 0 of culture. If more than two groups were being compared within a single experiment, an unpaired one-way analysis of variance was performed followed by Tukey's multiple comparison test to compare the mean of each group to the mean of every other group within the experiment. For all statistical tests, a significance value of 0.05 was used. For every analysis, the strength of p values is reported in the figures according the following: $P>0.05$ ns, $P\leq0.05$*, $P\leq0.01$, $P\leq0.001$*, $P\leq0.0001$****. Details of statistical tests can be found in the figure legends.

Example XI

This example demonstrates that iPSC-derived lung organoids can engraft into a mouse lung (see, FIG. 11).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

Complete citations for the references cited within the application are provided within the following reference list. Indeed, each of the following references are herein incorporated by reference in their entireties:

Abler, L. L., Mansour, S. L., Sun, X., 2009. Conditional gene inactivation reveals roles for Fgf10 and Fgfr2 in establishing a normal pattern of epithelial branching in the mouse lung. Dev. Dyn. 238, 1999-2013. doi:10.1002/dvdy.22032

Bagai, S., Rubio, E., Cheng, J.-F., Sweet, R., Thomas, R., Fuchs, E., Grady, R., Mitchell, M., Bassuk, J. A., 2002. Fibroblast growth factor-10 is a mitogen for urothelial cells. J. Biol. Chem. 277, 23828-23837. doi:10.1074/jbc.M201658200

Bellusci, S., Furuta, Y., Rush, M. G., Henderson, R., Winnier, G., Hogan, B. L., 1997a. Involvement of Sonic hedgehog (Shh) in mouse embryonic lung growth and morphogenesis. Development 124, 53-63.

Bellusci, S., Grindley, J., Emoto, H., Itoh, N., Hogan, B. L., 1997b. Fibroblast growth factor 10 (FGF10) and branching morphogenesis in the embryonic mouse lung. Development 124, 4867-4878.

Bellusci, S., Henderson, R., Winnier, G., Oikawa, T., Hogan, B. L., 1996. Evidence from normal expression and targeted misexpression that bone morphogenetic protein (Bmp-4) plays a role in mouse embryonic lung morphogenesis. Development 122, 1693-1702.

Branchfield, K., Li, R., Lungova, V., Verheyden, J. M., McCulley, D., Sun, X., 2015. A three-dimensional study of alveologenesis in mouse lung. Developmental Biology. doi:10.1016/j.ydbio.2015.11.017

Cardoso, W. V., Itoh, A., Nogawa, H., Mason, I., Brody, J. S., 1997. FGF-1 and FGF-7 induce distinct patterns of growth and differentiation in embryonic lung epithelium.

Dev. Dyn. 208, 398-405. doi:10.1002/(SICI)1097-0177(199703)208:3<398::AID-AJA10>3.0.CO; 2-X Chang, D. R., Martinez Alanis, D., Miller, R. K., Ji, H., Akiyama, H., McCrea, P. D., Chen, J., 2013. Lung epithelial branching program antagonizes alveolar differentiation. Proceedings of the National Academy of Sciences. doi:10.1073/pnas.1311760110

Chen, F., Cao, Y., Qian, J., Shao, F., Niederreither, K., Cardoso, W. V., 2010. A retinoic acid-dependent network in the foregut controls formation of the mouse lung primordium. J. Clin. Invest. 120, 2040-2048. doi:10.1172/JCI40253

Cornett, B., Snowball, J., Varisco, B. M., Lang, R., Whitsett, J., Sinner, D., 2013. Wntless is required for peripheral lung differentiation and pulmonary vascular development. Developmental Biology 379, 38-52. doi:10.1016/j.ydbio.2013.03.010

D'Amour, K. A., Agulnick, A. D., Eliazer, S., Kelly, O. G., Kroon, E., Baetge, E. E., 2005. Efficient differentiation of human embryonic stem cells to definitive endoderm. Nat Biotechnol 23, 1534-1541. doi:10.1038/nbt1163 del Moral, P.-M., Warburton, D., 2010. Explant culture of mouse embryonic whole lung, isolated epithelium, or mesenchyme under chemically defined conditions as a system to evaluate the molecular mechanism of branching morphogenesis and cellular differentiation. Methods Mol. Biol. 633, 71-79. doi:10.1007/978-1-59745-019-5_5

Desai, T. J., Chen, F., Lu, J., Qian, J., Niederreither, K., Done, P., Chambon, P., Cardoso, W. V., 2006. Distinct roles for retinoic acid receptors alpha and beta in early lung morphogenesis. Developmental Biology 291, 12-24. doi:10.1016/j.ydbio.2005.10.045

Desai, T. J., Malpel, S., Flentke, G. R., Smith, S. M., Cardoso, W. V., 2004. Retinoic acid selectively regulates Fgf10 expression and maintains cell identity in the prospective lung field of the developing foregut. Developmental Biology 273, 402-415. doi:10.1016/j.ydbio.2004.04.039

Domyan, E. T., Ferretti, E., Throckmorton, K., Mishina, Y., Nicolis, S. K., Sun, X., 2011. Signaling through BMP receptors promotes respiratory identity in the foregut via repression of Sox2. Development 138, 971-981. doi:10.1242/dev.053694

Domyan, E. T., Sun, X., 2010. Patterning and plasticity in development of the respiratory lineage. Dev. Dyn. 240, 477-485. doi:10.1002/dvdy.22504

Dye, B. R., Dedhia, P. H., Miller, A. J., Nagy, M. S., White, E. S., Shea, L. D., Spence, J. R., Rossant, J., 2016a. A bioengineered niche promotes in vivo engraftment and maturation of pluripotent stem cell derived human lung organoids. Elife 5, e19732. doi:10.7554/eLife.19732

Dye, B. R., Hill, D. R., Ferguson, M. A., Tsai, Y.-H., Nagy, M. S., Dyal, R., Wells, J. M., Mayhew, C. N., Nattiv, R., Klein, O. D., White, E. S., Deutsch, G. H., Spence, J. R., 2015. In vitro generation of human pluripotent stem cell derived lung organoids. Elife 4. doi:10.7554/eLife.05098

Dye, B. R., Miller, A. J., Spence, J. R., 2016b. How to Grow a Lung: Applying Principles of Developmental Biology to Generate Lung Lineages from Human Pluripotent Stem Cells. Curr Pathobiol Rep 1-11. doi:10.1007/s40139-016-0102-x Elluru, R. G., Whitsett, J. A., 2004. Potential role of Sox9 in patterning tracheal cartilage ring formation in an embryonic mouse model. Arch. Otolaryngol. Head Neck Surg. 130, 732-736. doi:10.1001/archotol.130.6.732

Firth, A. L., Dargitz, C. T., Qualls, S. J., Menon, T., Wright, R., Singer, O., Gage, F. H., Khanna, A., Verma, I. M., 2014. Generation of multiciliated cells in functional airway epithelia from human induced pluripotent stem cells. Proceedings of the National Academy of Sciences 111, E1723-30. doi:10.1073/pnas.1403470111

Ghaedi, M., Calle, E. A., Mendez, J. J., Gard, A. L., Balestrini, J., Booth, A., Bove, P. F., Gui, L., White, E. S., Niklason, L. E., 2013. Human iPS cell-derived alveolar epithelium repopulates lung extracellular matrix. J. Clin. Invest. 123, 4950-4962. doi:10.1172/JCI68793

Gilpin, S. E., Ren, X., Okamoto, T., Guyette, J. P., Mou, H., Rajagopal, J., Mathisen, D. J., Vacanti, J. P., Ott, H. C., 2014a. Enhanced lung epithelial specification of human induced pluripotent stem cells on decellularized lung matrix. Ann. Thorac. Surg. 98, 1721-9-discussion 1729. doi:10.1016/j.athoracsur.2014.05.080

Gilpin, S. E., Ren, X., Okamoto, T., Guyette, J. P., Mou, H., Rajagopal, J., Mathisen, D. J., Vacanti, J. P., Ott, H. C., 2014b. Enhanced Lung Epithelial Specification of Human Induced Pluripotent Stem Cells on Decellularized Lung Matrix. Ann. Thorac. Surg. 98, 1721-1729.

Goss, A. M., Tian, Y., Tsukiyama, T., Cohen, E. D., Zhou, D., Lu, M. M., Yamaguchi, T. P., Morrisey, E. E., 2009. Wnt2/2b and β-Catenin Signaling Are Necessary and Sufficient to Specify Lung Progenitors in the Foregut. Developmental Cell 17, 290-298. doi:10.1016/j.devcel.2009.06.005

Gotoh, S., Ito, I., Nagasaki, T., Yamamoto, Y., Konishi, S., Korogi, Y., Matsumoto, H., Muro, S., Hirai, T., Funato, M., Mae, S.-I., Toyoda, T., Sato-Otsubo, A., Ogawa, S., Osafune, K., Mishima, M., 2014. Generation of alveolar epithelial spheroids via isolated progenitor cells from human pluripotent stem cells. Stem Cell Reports 3, 394-403. doi:10.1016/j.stemcr.2014.07.005

Green, M. D., Chen, A., Nostro, M.-C., d'Souza, S. L., Schaniel, C., Lemischka, I. R., Gouon-Evans, V., Keller, G., Snoeck, H.-W., 2011. Generation of anterior foregut endoderm from human embryonic and induced pluripotent stem cells. Nat Biotechnol 1-7. doi:10.1038/nbt.1788

Harris-Johnson, K. S., Domyan, E. T., Vezina, C. M., Sun, X., 2009. beta-Catenin promotes respiratory progenitor identity in mouse foregut. Proceedings of the National Academy of Sciences 106, 16287-16292. doi:10.1073/pnas.0902274106

Hashimoto, S., Chen, H., Que, J., Brockway, B. L., Drake, J. A., Snyder, J. C., Randell, S. H., Stripp, B. R., 2012. β-Catenin-SOX2 signaling regulates the fate of developing airway epithelium. Journal of Cell Science 125, 932-942. doi:10.1242/jcs.092734

Herriges, J. C., Verheyden, J. M., Zhang, Z., Sui, P., Zhang, Y., Anderson, M. J., Swing, D. A., Zhang, Y., Lewandoski, M., Sun, X., 2015. FGF-Regulated ETV Transcription Factors Control FGF-SHH Feedback Loop in Lung Branching. Developmental Cell 35, 322-332. doi:10.1016/j.devcel.2015.10.006

Hines, E. A., Sun, X., 2014. Tissue crosstalk in lung development. J Cell Biochem 115, 1469-1477. doi:10.1002/jcb.24811

Huang, S. X. L., Islam, M. N., O'Neill, J., Hu, Z., Yang, Y.-G., Chen, Y.-W., Mumau, M., Green, M. D., Vunjak-Novakovic, G., Bhattacharya, J., Snoeck, H.-W., 2013. efficient generation of lung and airway epithelial cells from human pluripotent stem cells. Nat Biotechnol 1-11. doi:10.1038/nbt.2754

Kaarteenaho, R., Lappi-Blanco, E., Lehtonen, S., 2010. Epithelial N-cadherin and nuclear β-catenin are up-regulated during early development of human lung. BMC Dev Biol 10, 113. doi:10.1186/1471-213X-10-113

Kadzik, R. S., Cohen, E. D., Morley, M. P., Stewart, K. M., Lu, M. M., Morrisey, E. E., 2014. Wnt ligand/Frizzled 2 receptor signaling regulates tube shape and branch-point formation in the lung through control of epithelial cell shape. Proceedings of the National Academy of Sciences 111, 12444-12449. doi:10.1073/pnas.1406639111

Kim, C. F. B., Jackson, E. L., Woolfenden, A. E., Lawrence, S., Babar, I., Vogel, S., Crowley, D., Bronson, R. T., Jacks, T., 2005. Identification of bronchioalveolar stem cells in normal lung and lung cancer. Cell 121, 823-835. doi: 10.1016/j.cell.2005.03.032

Kim, H. Y., Nelson, C. M., 2012. Extracellular matrix and cytoskeletal dynamics during branching morphogenesis. Organogenesis 8, 56-64. doi:10.4161/org.19813

Konishi, S., Gotoh, S., Tateishi, K., Yamamoto, Y., Korogi, Y., Nagasaki, T., Matsumoto, H., Muro, S., Hirai, T., Ito, I., Tsukita, S., Mishima, M., 2015. Directed Induction of Functional Multi-ciliated Cells in Proximal Airway Epithelial Spheroids from Human Pluripotent Stem Cells. Stem Cell Reports 0. doi:10.1016/j.stemcr.2015.11.010

Kopp, J. L., Dubois, C. L., Schaffer, A. E., Hao, E., Shih, H. P., Seymour, P. A., Ma, J., Sander, M., 2011. Sox9+ ductal cells are multipotent progenitors throughout development but do not produce new endocrine cells in the normal or injured adult pancreas. Development 138, 653-665. doi: 10.1242/dev.056499

Lange, A. W., Sridharan, A., Xu, Y., Stripp, B. R., Perl, A.-K., Whitsett, J. A., 2015. Hippo/Yap signaling controls epithelial progenitor cell proliferation and differentiation in the embryonic and adult lung. Journal of Molecular Cell Biology 7, 35-47. doi:10.1093/jmcb/mju046

Lee, J.-H., Bhang, D. H., Beede, A., Huang, T. L., Stripp, B. R., Bloch, K. D., Wagers, A. J., Tseng, Y.-H., Ryeom, S., Kim, C. F., 2014. Lung Stem Cell Differentiation in Mice Directed by Endothelial Cells via a BMP4-NFATc1-Thrombospondin-1 Axis. Cell 156, 440-455. doi:10.1016/j.cell.2013.12.039

Longmire, T. A., Ikonomou, L., Hawkins, F., Christodoulou, C., Cao, Y., Jean, J. C., Kwok, L. W., Mou, H., Rajagopal, J., Shen, S. S., Dowton, A. A., Serra, M., Weiss, D. J., Green, M. D., Snoeck, H.-W., Ramirez, M. I., Kotton, D. N., 2012. Efficient derivation of purified lung and thyroid progenitors from embryonic stem cells. Cell Stem Cell 10, 398-411. doi:10.1016/j.stem.2012.01.019

Lu, B. C., Cebrian, C., Chi, X., Kuure, S., Kuo, R., Bates, C. M., Arber, S., Hassell, J., MacNeil, L., Hoshi, M., Jain, S., Asai, N., Takahashi, M., Schmidt-Ott, K. M., Barasch, J., D'Agati, V., Costantini, F., 2009. Etv4 and Etv5 are required downstream of GDNF and Ret for kidney branching morphogenesis. Nat Genet 41, 1295-1302. doi: 10.1038/ng.476

Mahoney, J. E., Mori, M., Szymaniak, A. D., Varelas, X., Cardoso, W. V., 2014. The Hippo Pathway Effector Yap Controls Patterning and Differentiation of Airway Epithelial Progenitors. Dev. Cell 1-14. doi:10.1016/j.devcel.2014.06.003

Makarenkova, H. P., Hoffman, M. P., Beenken, A., Eliseenkova, A. V., Meech, R., Tsau, C., Patel, V. N., Lang, R. A., Mohammadi, M., 2009. Differential interactions of FGFs with heparan sulfate control gradient formation and branching morphogenesis. Sci Signal 2, ra55-ra55. doi: 10.1126/scisignal.2000304

Malpel, S., Mendelsohn, C., Cardoso, W. V., 2000. Regulation of retinoic acid signaling during lung morphogenesis. Development 127, 3057-3067. Metzger, R. J., Klein, O. D., Martin, G. R., Krasnow, M. A., 2008. The branching programme of mouse lung development. Nature 453, 745-750. doi:10.1038/nature07005

Min, H., Danilenko, D. M., Scully, S. A., Bolon, B., Ring, B. D., Tarpley, J. E., DeRose, M., Simonet, W. S., 1998. Fgf-10 is required for both limb and lung development and exhibits striking functional similarity to *Drosophila* branchless. Genes & Development 12, 3156-3161.

Moens, C. B., Auerbach, A. B., Conlon, R. A., Joyner, A. L., Rossant, J., 1992. A targeted mutation reveals a role for N-myc in branching morphogenesis in the embryonic mouse lung. Genes Dev. 6, 691-704. doi:10.1101/gad.6.5.691

Morrisey, E. E., Cardoso, W. V., Lane, R. H., Rabinovitch, M., Abman, S. H., Ai, X., Albertine, K. H., Bland, R. D., Chapman, H. A., Checkley, W., Epstein, J. A., Kintner, C. R., Kumar, M., Minoo, P., Mariani, T. J., McDonald, D. M., Mukouyama, Y.-S., Prince, L. S., Reese, J., Rossant, J., Shi, W., Sun, X., Werb, Z., Whitsett, J. A., Gail, D., Blaisdell, C. J., Lin, Q. S., 2013. Molecular determinants of lung development. Ann Am Thorac Soc 10, S12-6. doi:10.1513/AnnalsATS.201207-036OT Morrisey, E. E., Hogan, B. L. M., 2010. Preparing for the First Breath: Genetic and Cellular Mechanisms in Lung Development. Developmental Cell 18, 8-23. doi:10.1016/j.devcel.2009.12.010

Motoyama, J., Liu, J., Mo, R., Ding, Q., Post, M., Hui, C. C., 1998. Essential function of Gli2 and Gli3 in the formation of lung, trachea and oesophagus. Nat Genet 20, 54-57. doi:10.1038/1711

Mou, H., Zhao, R., Sherwood, R., Ahfeldt, T., Lapey, A., Wain, J., Sicilian, L., Izvolsky, K., Musunuru, K., Cowan, C., Rajagopal, J., 2012. Generation of Multipotent Lung and Airway Progenitors from Mouse ESCs and Patient-Specific Cystic Fibrosis iPSCs. Cell Stem Cell 10, 385-397. doi:10.1016/j.stem.2012.01.018

Mucenski, M. L., Nation, J. M., Thitoff, A. R., Besnard, V., Xu, Y., Wert, S. E., Harada, N., Taketo, M. M., Stahlman, M. T., Whitsett, J. A., 2005. β-Catenin regulates differentiation of respiratory epithelial cells in vivo.

Mucenski, M. L., Wert, S. E., Nation, J. M., Loudy, D. E., Huelsken, J., Birchmeier, W., Morrisey, E. E., Whitsett, J. A., 2003. beta-Catenin is required for specification of proximal/distal cell fate during lung morphogenesis. J. Biol. Chem. 278, 40231-40238. doi:10.1074/jbc.M305892200

Nyeng, P., Norgaard, G. A., Kobberup, S., Jensen, J., 2008. FGF10 maintains distal lung bud epithelium and excessive signaling leads to progenitor state arrest, distalization, and goblet cell metaplasia. BMC Dev Biol 8, 2. doi:10.1186/1471-213X-8-2

Okubo, T., Knoepfler, P. S., Eisenman, R. N., Hogan, B. L. M., 2005. Nmyc plays an essential role during lung development as a dosage-sensitive regulator of progenitor cell proliferation and differentiation. Development 132, 1363-1374. doi:10.1242/dev.01678

Ornitz, D. M., Xu, J., Colvin, J. S., McEwen, D. G., MacArthur, C. A., Coulier, F., Gao, G., Goldfarb, M., 1996. Receptor specificity of the fibroblast growth factor family. J. Biol. Chem. 271, 15292-15297. doi:10.1074/jbc.271.25.15292

Ornitz, D. M., Yin, Y., 2012. Signaling Networks Regulating Development of the Lower Respiratory Tract. Cold Spring Harb Perspect Biol 4, a008318-a008318. doi: 10.1101/cshperspect.a008318

Perl, A.-K. T., Kist, R., Shan, Z., Scherer, G., Whitsett, J. A., 2005. Normal lung development and function after Sox9 inactivation in the respiratory epithelium. genesis 41, 23-32. doi:10.1002/gene.20093

Que, J., Okubo, T., Goldenring, J. R., Nam, K. T., Kurotani, R., Morrisey, E. E., Taranova, O., Pevny, L. H., Hogan, B. L. M., 2007. Multiple dose-dependent roles for Sox2 in the patterning and differentiation of anterior foregut endoderm. Development 134, 2521-2531. doi:10.1242/dev.003855

Rawlins, E. L., 2010. The building blocks of mammalian lung development. Dev. Dyn. 240, 463-476. doi:10.1002/dvdy.22482

Rawlins, E. L., Clark, C. P., Xue, Y., Hogan, B. L. M., 2009. The Id2+ distal tip lung epithelium contains individual multipotent embryonic progenitor cells. Development 136, 3741-3745. doi:10.1242/dev.037317

Rock, J. R., Hogan, B. L. M., 2011. Epithelial Progenitor Cells in Lung Development, Maintenance, Repair, and Disease. Annu. Rev. Cell Dev. Biol. 27, 493-512. doi:10.1146/annurev-cellbio-100109-104040

Rockich, B. E., Hrycaj, S. M., Shih, H.-P., Nagy, M. S., Ferguson, M. A. H., Kopp, J. L., Sander, M., Wellik, D. M., Spence, J. R., 2013. Sox9 plays multiple roles in the lung epithelium during branching morphogenesis. Proceedings of the National Academy of Sciences. doi:10.1073/pnas.1311847110

Sekine, K., Ohuchi, H., Fujiwara, M., Yamasaki, M., Yoshizawa, T., Sato, T., Yagishita, N., Matsui, D., Koga, Y., Itoh, N., Kato, S., 1999. Fgf10 is essential for limb and lung formation. Nat Genet 21, 138-141. doi:10.1038/5096

Shu, W., Guttentag, S., Wang, Z., Andl, T., Ballard, P., Lu, M. M., Piccolo, S., Birchmeier, W., Whitsett, J. A., Millar, S. E., Morrisey, E. E., 2005. Wnt/beta-catenin signaling acts upstream of N-myc, BMP4, and FGF signaling to regulate proximal-distal patterning in the lung. Dev Biol 283, 226-239.

Spence, J. R., Lange, A. W., Lin, S.-C. J., Kaestner, K. H., Lowy, A. M., Kim, I., Whitsett, J. A., Wells, J. M., 2009. Sox17 Regulates Organ Lineage Segregation of Ventral Foregut Progenitor Cells. Developmental Cell 17, 62-74. doi:10.1016/j.devcel.2009.05.012

Spence, J. R., Mayhew, C. N., Rankin, S. A., Kuhar, M. F., Vallance, J. E., Tolle, K., Hoskins, E. E., Kalinichenko, V. V., Wells, S. I., Zorn, A. M., Shroyer, N. F., Wells, J. M., 2011. Directed differentiation of human pluripotent stem cells into intestinal tissue in vitro. Nature 470, 105-109. doi:10.1038/nature09691

Tichelaar, J. W., Lu, W., Whitsett, J. A., 2000. Conditional expression of fibroblast growth factor-7 in the developing and mature lung. Journal of Biological Chemistry. doi:10.1074/jbc.275.16.11858

Varner, V. D., Nelson, C. M., 2014. Cellular and physical mechanisms of branching morphogenesis. Development 141, 2750-2759. doi:10.1242/dev.104794

Volckaert, T., Campbell, A., Dill, E., Li, C., Minoo, P., De Langhe, S., 2013. Localized Fgf10 expression is not required for lung branching morphogenesis but prevents differentiation of epithelial progenitors. Development 140, 3731-3742. doi:10.1242/dev.096560

Weaver, M., Dunn, N. R., Hogan, B. L., 2000. Bmp4 and Fgf10 play opposing roles during lung bud morphogenesis. Development 127, 2695-2704. Weaver, M., Yingling, J. M., Dunn, N. R., Bellusci, S., Hogan, B. L., 1999. Bmp signaling regulates proximal-distal differentiation of endoderm in mouse lung development. Development 126, 4005-4015.

White, A. C., Xu, J., Yin, Y., Smith, C., Schmid, G., Ornitz, D. M., 2006. FGF9 and SHH signaling coordinate lung growth and development through regulation of distinct mesenchymal domains. Development 133, 1507-1517. doi:10.1242/dev.02313

Wong, A. P., Bear, C. E., Chin, S., Pasceri, P., Thompson, T. O., Huan, L.-J., Ratjen, F., Ellis, J., Rossant, J., 2012. Directed differentiation of human pluripotent stem cells into mature airway epithelia expressing functional CFTR protein. Nat Biotechnol. doi:10.1038/nbt.2328

Yin, Y., Wang, F., Ornitz, D. M., 2011. Mesothelial- and epithelial-derived FGF9 have distinct functions in the regulation of lung development. Development 138, 3169-3177. doi:10.1242/dev.065110

Yin, Y., White, A. C., Huh, S.-H., Hilton, M. J., Kanazawa, H., Long, F., Ornitz, D. M., 2008. An FGF-WNT gene regulatory network controls lung mesenchyme development. Developmental Biology 319, 426-436. doi:10.1016/j.ydbio.2008.04.009

Zhang, M., Wang, H., Teng, H., Shi, J., Zhang, Y., 2010. Expression of SHH signaling pathway components in the developing human lung. Histochem. Cell Biol. 134, 327-335. doi:10.1007/s00418-010-0738-2

Zhang, X., Ibrahimi, O. A., Olsen, S. K., Umemori, H., Mohammadi, M., Ornitz, D. M., 2006. Receptor specificity of the fibroblast growth factor family. The complete mammalian FGF family. J. Biol. Chem. 281, 15694-15700. doi:10.1074/jbc.M601252200

Zhang, Y., Yokoyama, S., Herriges, J. C., Zhang, Z., Young, R. E., Verheyden, J. M., Sun, X., 2016. E3 ubiquitin ligase RFWD2 controls lung branching through protein-level regulation of ETV transcription factors. Proceedings of the National Academy of Sciences 201603310. doi:10.1073/pnas.1603310113

Zhao, R., Fallon, T. R., Saladi, S. V., Pardo-Saganta, A., Villoria, J., Mou, H., Vinarsky, V., Gonzalez-Celeiro, M., Nunna, N., Hariri, L. P., Camargo, F., Ellisen, L. W., Rajagopal, J., 2014. Yap tunes airway epithelial size and architecture by regulating the identity, maintenance, and self-renewal of stem cells. Developmental Cell 30, 151-165. doi:10.1016/j.devcel.2014.06.004.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method, comprising:
   culturing in vitro for approximately forty days cells from NKX2.1+ ventral-anterior foregut spheroid tissue derived from pluripotent stem cells, wherein the culturing results in differentiation of the cells from the NKX2.1+ ventral-anterior foregut spheroid tissue derived from pluripotent stem cells into tissue comprising 3-dimensional lung-like epithelium, wherein the culturing comprises activating the FGF signaling pathway, the retinoic acid signaling pathway, and the Wnt signaling pathway; and
   obtaining 3-dimensional lung tissue from the cultured tissue comprising 3-dimensional lung-like epithelium, wherein the obtained 3-dimensional lung tissue comprises a 3-dimensional lung tissue peripheral region and a 3-dimenstional lung tissue internal region,
   wherein the 3-dimensional lung tissue peripheral region comprises cells expressing SOX9 protein and SOX2 protein,
   wherein the 3-dimensional lung tissue internal region comprises cells expressing SOX2 protein, SCGB1A1 protein, and MUC5AC, wherein the 3-dimensional lung tissue internal region does not comprise cells expressing SOX9 protein.

2. The method of claim 1,
   wherein activating the Wnt signaling pathway comprises culturing the with a small molecule or agonist that activates the Wnt signaling pathway,
   wherein activating the FGF signaling pathway comprises culturing the cells with a small molecule or agonist that activates the FGF signaling pathway,
   wherein activating the RA signaling pathway comprises culturing the cells with a small molecule or agonist that activates the RA signaling pathway.

3. The method of claim 2,
   wherein the small molecule or agonist that activates the Wnt signaling pathway is CHIR99021,
   wherein the small molecule or agonist that activates the FGF signaling pathway is selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23,
   wherein the small molecule or agonist that activates the RA signaling pathway is selected from the group consisting of all-trans retinoic acid, AC 261066, AC 55649, adapalene, AM 580, AM 80, BMS 753, BMS 961, CD 1530, CD 2314, CD 437, Ch 55, isotretinoin, tazarotene, and TTNPB.

4. The method of claim 1, wherein the NKX2.1+ ventral-anterior foregut spheroid tissue is derived from definitive endoderm cells, wherein the definitive endoderm cells are derived from pluripotent stem cells, wherein the pluripotent stem cells are embryonic stem cells and/or induced pluripotent stem cells and/or or cells obtained through somatic cell nuclear transfer.

5. A method of treating a mammalian subject having a damaged lung tissue with reduced function, comprising:
   a) culturing in vitro for approximately forty days cells from NKX2.1+ ventral-anterior foregut spheroid tissue derived from pluripotent stem cells, wherein the culturing results in differentiation of the obtained NKX2.1+ ventral-anterior foregut spheroid tissue into tissue comprising 3-dimensional lung-like epithelium, wherein the culturing comprises activating the FGF signaling pathway, the retinoic acid signaling pathway, and the Wnt signaling pathway;
   b) obtaining 3-dimensional lung tissue from the cultured tissue comprising 3-dimensional lung-like epithelium, wherein the obtained 3-dimensional lung tissue comprises a 3-dimensional lung tissue peripheral region and a 3-dimensional lung tissue internal region,
      wherein the 3-dimensional lung tissue peripheral region comprises cells expressing SOX9 protein and SOX2 protein,
      wherein the 3-dimensional lung tissue internal region comprises cells expressing SOX2 protein, SCGB1A1 protein, and MUC5AC, wherein the 3-dimensional lung tissue internal region does not have cells expressing SOX9 protein;
   c) engrafting the obtained 3-dimensional lung tissue at the site of injury, wherein engrafted 3-dimensional lung tissue engraft at the site of injury and repopulate at least a portion of the site with the engrafted cells, wherein the repopulated cells supplement the function, thereby treating the subject.

6. The method of claim 5, wherein the damaged lung tissue is associated with a condition caused by one or more of
   an injury that results in a loss of epithelial function,
   a post-lung transplant complication, and/or
   a genetic disorder.

7. The method of claim 6,
   wherein the injury that results in loss of epithelial function is bronchiolitis obliterans;
   wherein the post-lung transplant complication is bronchiolitis obliterans;
   wherein the genetic disorder is cystic fibrosis.

8. The method of claim 5,
   wherein activating the Wnt signaling pathway comprises culturing the NKX2.1+ ventral-anterior foregut spheroid tissue with a small molecule or agonist that activates the Wnt signaling pathway,
   wherein activating the FGF signaling pathway comprises culturing the NKX2.1+ ventral-anterior foregut spheroid tissue with a small molecule or agonist that activates the FGF signaling pathway, wherein activating the RA signaling pathway comprises culturing the NKX2.1+ ventral-anterior foregut spheroid tissue with a small molecule or agonist that activates the RA signaling pathway.

9. The method of claim 8,
wherein the small molecule or agonist that activates the Wnt signaling pathway is CHIR99021,
wherein the small molecule or agonist that activates the FGF signaling pathway is selected from FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23,
wherein the small molecule or agonist that activates the RA signaling pathway is selected from the group consisting of all-trans retinoic acid, AC 261066, AC 55649, adapalene, AM 580, AM 80, BMS 753, BMS 961, CD 1530, CD 2314, CD 437, Ch 55, isotretinoin, tazarotene, and TTNPB.

10. The method of claim 5, comprising at least one of the following:
wherein the activating one or more signaling pathways within the NKX2.1+ ventral-anterior foregut spheroid tissue occurs over a specified temporal period,
wherein the activating one or more signaling pathways within the NKX2.1+ ventral-anterior foregut spheroid tissue occurs comprises activating two or more signaling pathways.

11. The method of claim 5, wherein the NKX2.1+ ventral-anterior foregut spheroid tissue is derived from definitive endoderm cells, wherein the definitive endoderm cells are derived from pluripotent stem cells, wherein the pluripotent stem cells are embryonic stem cells and/or induced pluripotent stem cells and/or or cells obtained through somatic cell nuclear transfer.

* * * * *